(12) United States Patent
Svendsen et al.

(10) Patent No.: US 7,326,554 B2
(45) Date of Patent: Feb. 5, 2008

(54) PHYTASE VARIANTS

(75) Inventors: Allan Svendsen, Birkerod (DK); Soren Flensted Lassen, Kobenhavn O (DK); Dirk Kostrewa, Freiburg (DE); Luis Pasamontes, Montclair, NJ (US); Martin Lehman, Princeton, NJ (US); Andrea Tomschy, Grenzach-Wyhlen (DE); Adolphus Van Loon, Rheinfelden (CH); Kurt Vogel, Basel (CH); Markus Wyss, Liestal (CH)

(73) Assignee: Novozymes Als, Bagsvaerd (DK)

( * ) Notice: Subject to any disclaimer, the term of this patent is extended or adjusted under 35 U.S.C. 154(b) by 272 days.

(21) Appl. No.: 10/734,510

(22) Filed: Dec. 12, 2003

(65) Prior Publication Data

US 2004/0175376 A1    Sep. 9, 2004

Related U.S. Application Data

(60) Division of application No. 10/083,452, filed on Feb. 26, 2002, now Pat. No. 6,689,358, which is a continuation of application No. 09/273,871, filed on Mar. 22, 1999, now Pat. No. 6,514,495.

(60) Provisional application No. 60/117,677, filed on Jan. 28, 1999, provisional application No. 60/101,642, filed on Sep. 24, 1998, provisional application No. 60/090,675, filed on Jun. 25, 1998, provisional application No. 60/080,129, filed on Mar. 31, 1998.

(30) Foreign Application Priority Data

| Mar. 23, 1998 | (DK) | PA 1998 00407 |
| Jun. 19, 1998 | (DK) | PA 1998 00806 |
| Sep. 18, 1998 | (DK) | PA 1998 01176 |
| Jan. 22, 1999 | (DK) | PA 1999 00091 |

(51) Int. Cl.
C12N 9/16 (2006.01)

(52) U.S. Cl. ............ 435/196; 536/23.2; 435/252.3; 435/320.1

(58) Field of Classification Search ........ 435/196, 435/254.1, 320.1, 471, 911, 916; 424/94.6; 536/23.2, 23.7

See application file for complete search history.

(56) References Cited

U.S. PATENT DOCUMENTS

| 6,039,942 A | 3/2000 | Lassen et al. ........ 424/94.6 |
| 6,060,298 A * | 5/2000 | Lassen et al. ........ 435/196 |
| 6,153,418 A | 11/2000 | Lehmann ........ 435/195 |
| 6,391,605 B1 | 5/2002 | Kostrewa et al. ........ 435/196 |
| 6,514,495 B1 | 2/2003 | Svendsen et al. ........ 424/94.6 |

FOREIGN PATENT DOCUMENTS

| EP | 0420358 A1 | 4/1991 |
| EP | 0 684 313 | 11/1995 |
| EP | 0897010 A2 | 2/1999 |
| EP | 0897985 A2 | 2/1999 |
| WO | WO 91/14782 | 10/1991 |
| WO | WO 97/35016 | 9/1997 |
| WO | WO 97/35017 | 9/1997 |
| WO | WO 97/48812 | 12/1997 |

OTHER PUBLICATIONS

Piddington, C.S. et al.,Gene, vol. 133, pp. 55-62 (1993).
Yamada et al., 1986, Agric.Biol. Chem. vol. 32, Part 10: pp. 1275-1282 (1968).
Bowie et al., Science, vol. 247, pp. 1306-1310 (1990).

* cited by examiner

*Primary Examiner*—Tekchand Saidha
(74) *Attorney, Agent, or Firm*—Elias Lambiris

(57) ABSTRACT

The present invention relates to phytase variants, their preparation and uses, which phytase variants, when aligned according to FIG. 1, are amended as compared to a model phytase in at least one of a number of positions. Preferred model phytases are basidiomycete and ascomycete phytases, such as *Peniophora* phytase and *Aspergillus* phytases. Preferred phytase variants exhibits amended activity characteristics, such as improved specific activity and/or improved thermostability.

31 Claims, 10 Drawing Sheets

Fig. 1A

```
Peniophora numbers          1                                                     37
Alignment numbers    1                                                            50
      P_involtus_A1  ........ML FGFVALACLL SLSEVLATSV P......KNT APTFPIPESE
      P_involtus_A2  ........MH LGFVTLACLI HLSEVFAASV P......RNI APKFSIPESE
         T_pubescens ..........  MAFSILASLL FVCYAYARAV PRAHIPLRDT SACLDVTRDV
          A_pediades ..........  MSLFIGGCLL VFLQASAYGG VVQATFVQPF .....FPPQI
              P_lycii ........MV SSAFAPSILL SLMSSLALST QFSF.....V AAQLPIPAQN
          A_fumigatus ......MVTL TFLLSAAYLL .SGRVSAAPS SAGSKSCDTV DLGYQCSPAT
             conspnyA ......MGVF VVLLSIATLF GSTSGTALGP RGNSHSCDTV DGGYQCFPEI
           A_nidulans ......MAFF TVALSLYYLL ..SRVSAQAP VVQNHSCNTA DGGYQCFPNV
    A_ficuum_NRRL3135 ......MGVS AVLLPLYLLS GVTSGLAVPA SRNQSSCDTV DQGYQCFSET
             A_terreus ......MGFL AIVLSVALLF RSTSGTPLGP RGKHSDCNSV DHGYQCFPEL
               T_thermo ......MSLL LLVLSGGLVA LYVS...RNP HVDSHSCNTV EGGYQCRPEI
           T_lanuginosa MAGIGLGSFL VLLLQFSALL TASPAIPPFW RKKHPNVD.. ..........I
           M_thermophila ......MTGL GVMVVMVGFL AIASL..... QSESRPCDTP DLGFQCGTAI 38                                               83
                                 51                                              100
      P_involtus_A1  QRNWSPYSPY FPLAEYKA.. ..PPAGCQIN QVNIIQRHGA RFPTSGATTR
      P_involtus_A2  QRNWSPYSPY FPLAEYKA.. ..PPAGCEIN QVNIIQRHGA RFPTSGAATR
         T_pubescens QQSWSMYSPY FPAATYVA.. ..PPASCQIN QVHIIQRHGA RFPTSGAAKR
          A_pediades QDSWAAYTPY YPVQAYTP.. ..PPKDCKIT QVNIIQRHGA RFPTSGAGTR
              P_lycii TSNWGPYDPF FPVEPYAA.. ..PPEGCTVT QVNLIQRHGA RWPTSGARSR
          A_fumigatus SHLWGQYSPF FSLEDELSVS SKLPKDCRIT LVQVLSRHGA RYPTSSKSKK
             conspnyA SHLWGQYSPY FSLEDESAIS PDVPDDCRVT FVQVLSRHGA RYPTSSKSKA
           A_nidulans SHVWGQYSPY FSIEQESAIS EDVPHGCEVT FVQVLSRHGA RYPTESKSKA
    A_ficuum_NRRL3135 SHLWGQYAPF FSLANESVIS PEVPAGCRVT FAQVLSRHGA RYPTDSKGKK
             A_terreus SHKWGLYAPY FSLQDESPFP LDVPEDCHIT FVQVLARHGA RSPTHSKTKA
               T_thermo SHSWGQYSPF FSLADQSEIS PDVPQNCKIT FVQLLSRHGA RYPTSSKTEL
           T_lanuginosa ARHWGQYSPF FSLAEVSEIS PAVPKGCRVE FVQVLSRHGA RYPTAHKSEV
           M_thermophila SHFWGQYSPY FSVP..SELD ASIPDDCEVT FAQVLSRHGA RAPTLKRAAS 84                                              133
                                101                                              150
      P_involtus_A1  IKAGLTKLQG VQNFTDAKFN FIKSFKYDLG NSDLVPFGAA QSFDAGQEAF
      P_involtus_A2  IKAGLSKLQS VQNFTDPKFD FIKSFTYDLG TSDLVPFGAA QSFDAGLEVF
         T_pubescens IQTAVAKLKA ASNYTDPLLA FVTNYTYSLG QDSLVELGAT QSSEAGQEAF
          A_pediades IQAAVKKLQS AKTYTDPRLD FLTNYTYTLG HDDLVPFGAL QSSQAGEETF
              P_lycii QVAAVAKIQM ARPFTDPKYE FLNDFVYKFG VADLLPFGAN QSHQTGTDMY
          A_fumigatus YKKLVTAIQA NATDFKGKFA FLKTYNYTLG ADDLTPFGEQ QLVNSGIKFY
             conspnyA YSALIEAIQK NATAFGKYA FLKTYNYTLG ADDLTPFGEN QMVNSGIKFY
           A_nidulans YSGLIEAIQK NATSFWGQYA FLESYNYTLG ADDLTIFGEN QMVDSGAKFY
    A_ficuum_NRRL3135 YSALIEEIQQ NATTFDGKYA FLKTYNYSLG ADDLTPFGEQ ELVNSGIKFY
             A_terreus YAATIAAIQK SATAFPGKYA FLQSYNYSLD SEELTPFGRN QLRDLGAQFY
               T_thermo YSQLISRIQK TATAYKGYYA FLKDYRYQLG ANDLTPFGEN QMIQLGIKFY
           T_lanuginosa YAELLQRIQD TATEFKGDFA FLRDYAYHLG ADNLTRFGEE QMMESGRQFY
           M_thermophila YVDLIDRIHH GAISYGPGYE FLRTYDYTLG ADELTRTGQQ QMVNSGIKFY
```

Fig. 1B

```
                        134                                                 176
                        151                                                 200
     P_involtus_A1  ARYSKLVSKN  NLPFIRADGS  DRVVDSATNW  TAGFASA...  ....SHNTVQ
     P_involtus_A2  ARYSKLVSSD  NLPFIRSDGS  DRVVDTATNW  TAGFASA...  ....SRNAIQ
       T_pubescens  TRYSSLVSAD  ELPFVRASGS  DRVVATANNW  TAGFALA...  ....SSNSIT
        A_pediades  QRYSFLVSKE  NLPFVRASSS  NRVVDSATNW  TEGFSAA...  ....SHHVLN
           P_lycii  TRYSTLFEGG  DVPFVRAAGD  QRVVDSSTNW  TAGFGDA...  ....SGETVL
        A_fumigatus QRYKAL.ARS  VVPFIRASGS  DRVIASGEKF  IEGFQQAKLA  DPGA.TNRAA
          consphyA  RRYKAL.ARK  IVPFIRASGS  DRVIASAEKF  IEGFQSAKLA  DPGSQPHQAS
        A_nidulans  RRYKNL.ARK  NTPFIRASGS  DRVVASAEKF  INGFRKAQLH  DHGS..KRAT
  A_ficuum_NRRL3135 QRYESL.TRN  IVPFIRSSGS  SRVIASGKKF  IEGFQSTKLK  DPRAQPGQSS
          A_terreus ERYNAL.TRH  INPFVRATDA  SRVHESAEKF  VEGFQTARQD  DHHANPHQPS
           T_thermo NHYKSL.ARN  AVPFVRCSGS  DRVIASGRLF  IEGFQSAKVL  DPHSDKHDAP
        T_lanuginosa HRYREQ.ARE IVPFVRAAGS  ARVIASAEFF  NRGFQDAKDR  DPRSNKDQAE
       M_thermophila RRYRAL.ARK SIPFVRTAGQ  DRVVHSAENF  TQGFHSALLA  DRGSTVRPTL 177                                                 217
                        201                                                 250
     P_involtus_A1  PKLNLILPQT  G..NDTLEDN  MCPAAGD...  ...SDPQVNA  WLAVAFPSIT
     P_involtus_A2  PKLDLILPQT  G..NDTLEDN  MCPAAGE...  ...SDPQVDA  WLASAFPSVT
       T_pubescens  PVLSVIISEA  G..NDTLDDN  MCPAAGD...  ...SDPQVNQ  WLAQFAPPMT
        A_pediades  PILFVILSES  L..NDTLDDA  MCPNAGS...  ...SDPQTGI  WTSIYGTPIA
           P_lycii  PTLQVVLQEE  G..NCTLCNN  MCPNEVD...  ...GD.ESTT  WLGVFAPNIT
        A_fumigatus PAISVIIPES  ETFNNTLDHG  VCTKFEA...  SQLGDEVAAN  FTALFAPDIR
          consphyA  PVIDVIIPEG  SGYNNTLDHG  TCTAFED...  SELGDDVEAN  FTALFAPAIR
        A_nidulans  PVVNVIIPEI  DGFNNTLDHS  TCVSFEN...  DERADEIEAN  FTAIMGPPIR
  A_ficuum_NRRL3135 PKIDVVISEA  SSSNNTLDPG  TCTVFED...  SELADTVEAN  FTATFVPSIR
          A_terreus PRVDVAIPEG  SAYNNTLEHS  LCTAFES...  STVGDDAVAN  FTAVFAPAIA
           T_thermo PTINVIIEEG  PSYNNTLDTG  SCPVFED...  SSGGHDAQEK  FAKQFAPAIL
        T_lanuginosa PVINVIISEE TGSNNTLDGL  TCPAAEE...  AP.DPTQPAE  FLQVFGPRVL
       M_thermophila PYDMVVIPET AGANNTLHND  LCTAFEEGPY  STIGDDAQDT  YLSTFAGPIT 218                                                 252
                        251                                                 300
     P_involtus_A1  ARLNAAAPSV  NLTDTDAFNL  VSLCAFLTVS  KEKK......  .........S
     P_involtus_A2  AQLNAAAPGA  NLTDADAFNL  VSLCPFMTVS  KEQK......  .........S
       T_pubescens  ARLNAGAPGA  NLTDTDTYNL  LTLCPFETVA  TERR......  .........S
        A_pediades  NRLNQQAPGA  NITAADVSNL  IPLCAFETIV  KETP......  .........S
           P_lycii  ARLNAAAPSA  NLSDSDALTL  MDMCPFDTLS  SGNA......  .........S
        A_fumigatus ARAEKHLPGV  TLTDEDVVSL  MDMCSFDTVA  RTSD..ASQ.  ........LS
          consphyA  ARLEADLPGV  TLTDEDVVYL  MDMCPFETVA  RTSD..ATE.  ........LS
        A_nidulans  KRLENDLPGI  KLTNENVIYL  MDMCSFDTMA  RTAH..GTE.  ........LS
  A_ficuum_NRRL3135 QRLENDLSGV  TLTDTEVTYL  MDMCSFDTIS  TSTV..DTK.  ........LS
          A_terreus QRLEADLPGV  QLSTDDVVNL  MAMCPFETVS  LTDD..AHT.  ........LS
           T_thermo EKIKDHLPGV  DLAVSDPYL   MDLCPFETLA  RNHT..DT..  ........LS
        T_lanuginosa KKITKHMPGV NLTLEDVPLF  MDLCPFDTVG  SDPVLFPRQ.  ........LS
       M_thermophila ARVNANLPGA NLTDADTVAL  MDLCPFETVA  SSSSDPATAD  AGGGNGRPLS
```

Fig. 1C

```
                       253                                                         300
                       301                                                         350
     P_involtus_A1     DFCTLFEGIP  GSFEAFAYGG  DLDKFYGTGY  GQELGPVQGV  GYVNELIARL
     P_involtus_A2     DFCTLFEGIP  GSFEAFAYAG  DLDKFYGTGY  GQALGPVQGV  GYINELLARL
        T_pubescens    EFCDIYEELQ  AE.DAFAYNA  DLDKFYGTGY  GQPLGPVQGV  GYINELIARL
        A_pediades     PFCNLFT..P  EEFAQFEYFG  DLDKFYGTGY  GQPLGPVQGV  GYINELLARL
            P_lycii    PFCDLFT..A  EEYVSYEYYY  DLDKYYGTGP  GNALGPVQGV  GYVNELLARL
        A_fumigatus    PFCQLFT..H  NEWKKYNYLQ  SLGKYYGYGA  GNPLGPAQGI  GFTNELIARL
            consphyA   PFCALFT..H  DEWRQYDYLQ  SLGKYYGYGA  GNPLGPAQGV  GFANELIARL
          A_nidulans   PFCAIFT..E  KEWLQYDYLQ  SLSKYYGYGA  GSPLGPAQGI  GFTNELIARL
    A_ficuum_NRRL3135  PFCDLFT..H  DEWINYDYLQ  SLKKYYGHGA  GNPLGPTQGV  GYANELIARL
           A_terreus   PFCDLFT..A  TEWTQYNYLL  SLDKYYGYGG  GNPLGPVQGV  GWANELMARL
             T_thermo  PFCALST..Q  EEWQAYDYYQ  SLGKYYGNGG  GNPLGPAQGV  GFVNELIARM
         T_lanuginosa  PFCHLFT..A  DDWMAYDYYY  TLDKYYSHGG  GSAFGPSRGV  GFVNELIARM
        M_thermophila  PFCRLFS..E  SEWRAYDYLQ  SVGKWYGYGP  GNPLGPTQGV  GFVNELLARL 301                                               349
                       351                                               400
     P_involtus_A1     TNS.AVRDNT  QTNRTLDASP  VTFPLNKTFY  ADFSHDNLMV  AVFSAMGLFR
     P_involtus_A2     TNS.AVNDNT  QTNRTLDAAP  DTFPLNKTMY  ADFSHDNLMV  AVFSAMGLFR
        T_pubescens    TAQ.NVSDHT  QTNSTLDSSP  ETFPLNRTLY  ADFSHDNQMV  AIFSAMGLFN
        A_pediades     TEM.PVRDNT  QTNRTLDSSP  LTFPLDRSIY  ADLSHDNQMI  AIFSAMGLFN
            P_lycii    TGQ.AVRDET  QTNRTLDSDP  ATFPLNRTFY  ADFSHDNTMV  PIFAALGLFN
        A_fumigatus    TRS.PVQDHT  STNSTLVSNP  ATFPLNATMY  VDFSHDNSMV  SIFFALGLYN
            consphyA   TRS.PVQDHT  STNHTLDSNP  ATFPLNATLY  ADFSHDNSMI  SIFFALGLYN
          A_nidulans   TQS.PVQDNT  STNHTLDSNP  ATFPLDRKLY  ADFSHDNSMI  SIFFAMGLYN
    A_ficuum_NRRL3135  THS.PVHDDT  SSNHTLDSSP  ATFPLKSTLY  ADFSHDNGII  SILFALGLYN
           A_terreus   TRA.PVHDHT  CVNNTLDASP  ATFPLNATLY  ADFSHDSNLV  SIFWALGLYN
             T_thermo  THS.PVQDYT  TVNHTLDSNP  ATFPLNATLY  ADFSHDNTMT  SIFAALGLYN
         T_lanuginosa  TGNLPVKDHT  TVNHTLDDNP  ETFPLDAVLY  ADFSHDNTMT  GIFSAMGLYN
        M_thermophila  A.GVPVRDGT  STNRTLDGDP  RTFPLGRPLY  ADFSHDNDMM  GVLGALGAYD 350                                               383
                       401                                               450
     P_involtus_A1     QPAPLSTSVP  NPWR.....T  WRTSSLVPFS  GRMVVERLSC  ..........
     P_involtus_A2     QSAPLSTSTP  DPNR.....T  WLTSSVVPFS  ARMAVERLSC  ..........
        T_pubescens    QSAPLDPTTP  DPAR.....T  FLVKKIVPFS  ARMVVERLDC  ..........
        A_pediades     QSSPLDPSFP  NPKR.....T  WVTSRLTPFS  ARMVTERLLC  QRDGTGSGGP
            P_lycii    ATA.LDPLKP  DENR.....L  WVDSKLVPFS  GHMTVEKLAC  ..........
        A_fumigatus    GTEPLSRTSV  ESAKE..LDG  YSASWVVPFG  ARAYFETMQC  ..........
            consphyA   GTAPLSTTSV  ESIEE..TDG  YSASWTVPFG  ARAYVEMMQC  ..........
          A_nidulans   GTQPLSMDSV  ESIQE..MDG  YAASWTVPFG  ARAYFELMQC  ..........
    A_ficuum_NRRL3135  GTKPLSTTTV  ENITQ..TDG  FSSAWTVPFA  SRLYVEMMQC  ..........
           A_terreus   GTAPLSQTSV  ESVSQ..TDG  YAAAWTVPFA  ARAYVEMMQC  ..........
             T_thermo  GTAKLSTTEI  KSIEE..TDG  YSAAWTVPFG  GRAYIEMMQC  ..........
         T_lanuginosa  GTKPLSTSKI  QPPTGAAADG  YAASWTVPFA  ARAYVELLRC  ETETSSEEEE
        M_thermophila  GVPPLDKTAR  RDPEE..LGG  YAASWAVPFA  ARIYVEKMRC  SGGGGGGGGG
```

Fig. 1D

```
                            384                                                 425
                       451                                                 500
    P_involtus_A1      .......FGT  TKVRVLVQDQ  VQPLEFCGGD  RNGLCTLAKF  VESQTFARSD
    P_involtus_A2      .......AGT  TKVRVLVQDQ  VQPLEFCGGD  QDGLCALDKF  VESQAYARSG
       T_pubescens     .......GGA  QSVRLLVNDA  VQPLAFCGAD  TSGVCTLDAF  VESQAYARND
        A_pediades     SRIMRNGNVQ  TFVRILVNDA  LQPLKFCGGD  MDSLCTLEAF  VESQKYARED
            P_lycii    .......SGK  EAVRVLVNDA  VQPLEFCGG.  VDGVCELSAF  VESQTYAREN
        A_fumigatus    K..S...EKE  PLVRALINDR  VVPLHGCDVD  KLGRCKLNDF  VKGLSWARSG
          consphyA     Q..A...EKE  PLVRVLVNDR  VVPLHGCAVD  KLGRCKRDDF  VEGLSFARSG
         A_nidulans    E......KKE  PLVRVLVNDR  VVPLHGCAVD  KFGRCTLDDW  VEGLNFARSG
  A_ficuum_NRRL3135    Q..A...EQA  PLVRVLVNDR  VVPLHGCPVD  ALGRCTRDSF  VRGLSFARSG
          A_terreus    R..A...EKE  PLVRVLVNDR  VMPLHGCPTD  KLGRCKRDAF  VAGLSFAQAG
           T_thermo    D..D...SDE  PVVRVLVNDR  VVPLHGCEVD  SLGRCKRDDF  VRGLSFARQG
       T_lanuginosa    E..G...EDE  PFVRVLVNDR  VVPLHGCRVD  RWGRCRRDEW  IKGLTFARQG
      M_thermophila    E..GRQEKDE  EMVRVLVNDR  VMTLKGCGAD  ERGMCTLERF  IESMAFARGN 426         439
                       501         514
    P_involtus_A1      GAGDFEKCFA  TSA.
    P_involtus_A2      GAGDFEKCLA  TTV.
       T_pubescens     GEGDFEKCFA  T...
        A_pediades     GQGDFEKCFD  ....
            P_lycii    GQGDFAKCGF  VPSE
        A_fumigatus    ..GNWGECFS  ....
          consphyA     ..GNWAECFA  *...
         A_nidulans    ..GNWKTCFT  L...
  A_ficuum_NRRL3135    ..GDWAECFA  ....
          A_terreus    ..GNWADCF.  ....
           T_thermo    ..GNWEGCYA  ASE.
       T_lanuginosa    ..GHWDRCF.  ....
      M_thermophila    ..GKWDLCFA  ....
```

Fig. 2

```
AAGCTTGGGCAAACTCATCATGCTCATCTTGATGATTCCACTGTTCAGCTACCTGGCTGCTGCTTCTCTGTGGGTTCATC    80
HindIII            M  L  I  L  M  I  P  L  F  S  Y  L  A  A  A  S  L CTTTGCCCCTGTCTCGATGTTAAAATACTAAACATATTTCACCAGACGTGTACTCTCCCCTCAGCCAGTGTCCTGTGACA   160
                                              R  V  L  S  P  Q  P  V  S  C  D GCCCGGAGCTTGGTTACCAATGCGACCAGCAGACAACGCACACCTGGGGTCAATACTCACCCTTCTTCTCTGTCCCGTCA   240
 S  P  E  L  G  Y  Q  C  D  Q  Q  T  T  H  T  W  G  Q  Y  S  P  F  F  S  V  P  S GAGATCTCCCCTTCCGTTCCTGATGGCTGCCGCCTCACCTTCGCCCAAGTTCTCTCCCGCCACGGCGCCCGCTTCCCAAC   320
 E  I  S  P  S  V  P  D  G  C  R  L  T  F  A  Q  V  L  S  R  H  G  A  R  F  P  T CCCGGGTAAAGCCGCCGCCATCTCCGCTGTCCTCACCAAAATCAAAACCTCTGCCACCTGGTACGGTTCCGACTTTCAGT   400
  P  G  K  A  A  A  I  S  A  V  L  T  K  I  K  T  S  A  T  W  Y  G  S  D  F  Q TCATCAAGAACTACGACTATGTACTTGGCGTAGACCACCTGACCGCGTTCGGCGAGCAAGAAATGGTCAACTCCGGCATC   480
 F  I  K  N  Y  D  Y  V  L  G  V  D  H  L  T  A  F  G  E  Q  E  M  V  N  S  G  I AAGTTCTACCAGCGCTACTCCTCCCTCATCCAGACAGAAGACTCGGATACGCTCCCCTTCGTCCGCGCCTCTGGCCAGGA   560
  K  F  Y  Q  R  Y  S  S  L  I  Q  T  E  D  S  D  T  L  P  F  V  R  A  S  G  Q  E ACGCGTCATCGCCTCCGCCGAGAACTTCACCACCGGCTTCTACTCGGCCCTCTCAGCCGACAAGAACCCTCCTTCCTCCT   640
  R  V  I  A  S  A  E  N  F  T  T  G  F  Y  S  A  L  S  A  D  K  N  P  P  S  S TACCAAGACCAGAAATGGTCATCATTTCTGAGGAGCCAACAGCCAACAACACCATGCACCACGGCCTCTGCCGCTCCTTT   720
 L  P  R  P  E  M  V  I  I  S  E  E  P  T  A  N  N  T  M  H  H  G  L  C  R  S  F GAAGATTCCACCACCGGCGACCAAGCCCAAGCGGAATTCATCGCCGCCACCTTCCCACCCATCACCGCCCGTCTCAACGC   800
 E  D  S  T  T  G  D  Q  A  Q  A  E  F  I  A  A  T  F  P  P  I  T  A  R  L  N  A CCAAGGTTTCAAAGGCGTCACCCTCTCCAACACCGACGTCCTATCACTAATGGACCTCTGCCCCTTTGACACCGTCGCCT   880
  Q  G  F  K  G  V  T  L  S  N  T  D  V  L  S  L  M  D  L  C  P  F  D  T  V  A ACCCCCTTTCCTCCCTCACCACCACCTCTTCCGTTTCTGGAGGCGGCAAGTTATCCCCCTTCTGCTCTCTTTTCACTGCC   960
 Y  P  L  S  S  L  T  T  T  S  S  V  S  G  G  G  K  L  S  P  F  C  S  L  F  T  A AGCGACTGGACAATCTACGATTACCTCCAGTCCCTAGGGAAATACTACGGTTTCGGCCCCGGTAATTCCCTAGCTGCCAC   1040
 S  D  W  T  I  Y  D  Y  L  Q  S  L  G  K  Y  Y  G  F  G  P  G  N  S  L  A  A  T CCAGGGGGTAGGGTACGTCAACGAGCTTATCGCCCGCTTGATCCGTGCTCCCGTCGTAGATCACACGACGACCAACTCTA   1120
  Q  G  V  G  Y  V  N  E  L  I  A  R  L  I  R  A  P  V  V  D  H  T  T  T  N  S CTCTTGATGGCGACGAAAAAACGTTTCCGTTGAACAGAACGGTGTATGCGGATTTTTCCCATGATAATGATATGATGAAT   1200
 T  L  D  G  D  E  K  T  F  P  L  N  R  T  V  Y  A  D  F  S  H  D  N  D  M  M  N ATCCTGACTGCTTTGCGGATATTCGAGCATATCAGTCCGATGGATAACACCACTATCCCGACCAACTATGGCCAGACAGG   1280
  I  L  T  A  L  R  I  F  E  H  I  S  P  M  D  N  T  T  I  P  T  N  Y  G  Q  T  G AGATGACGGGGTGAAGGAAAGGGATTTGTTCAAGGTTAGTTGGGCGGTGCCCTTTGCTGGGAGGGTGTACTTTGAGAAAA   1360
  D  D  G  V  K  E  R  D  L  F  K  V  S  W  A  V  P  F  A  G  R  V  Y  F  E  K TGGTTTGTGATGCGGATGGGGATGGCAAGATTGATAGTGATGAGGCTCAGAAAGAGTTGGTGAGGATTTTGGTTAATGAT   1400
 M  V  C  D  A  D  G  D  G  K  I  D  S  D  E  A  Q  K  E  L  V  R  I  L  V  N  D CGGGTGATGAGATTGAATGGGTGTGATGCTGATGAACAGGGTAGGTGTGGATTGGAGAAGTTTGTGGAGAGTATGGAGTT   1520
 R  V  M  R  L  N  G  C  D  A  D  E  Q  G  R  C  G  L  E  K  F  V  E  S  M  E  F TGCGAGGAGAGGGGGGGAGTGGGAGGAGAGGTGTTTTGTTTAGCTCTAGA
  A  R  R  G  G  E  W  E  E  R  C  F  V       XbaI
```

Fig. 3

```
  1 ..MLILMIPLFSYLAAASLRVLSPQPVSCDSPELGYQCDQQTTHTWGQYS  48
       :|:..:.::||  |||.  |.    .||.|:||:||:  ...| |||||
  1 MTGLGVMVVMVGFLAIASLQSESR...PCDTPDLGFQCGTAISHFWGQYS  47

49 PFFSVPSEISPSVPDGCRLTFAQVLSRHGARFPTPGKAAAISAVLTKIKT  98
    |:||||||:..:|:||:| :||||||||||||| ||  :||.. .::.:|.
 48 PYFSVPSELDASIPDDCEVTFAQVLSRHGARAPTLKRAASYVDLIDRIHH  97

99 SATWYGSDFQFIKNYDYVLGVDHLTAFGEQEMVNSGIKFYQRYSSLIQTE 148
    :|..||.:::|::.|||.||.|.|| |:|:|||||||||.||..|
 98 GAISYGPGYEFLRTYDYTLGADELTRTGQQQMVNSGIKFYRRYRAL.... 143

149 DSDTLPFVRASGQERVIASAENFTTGFYSALSADKNPPSSLRP.EMVII  197
    ....:||||..||:||: ||||||  ||.|||  ||:...  . |  :||:|
144 ARKSIPFVRTAGQDRVVHSAENFTQGFHSALLADRGSTVRPTLPYDMVVI 193

198 SEEPTANNTMHHGLCRSFED...STTGDQAQAEFIAATFPPITARLNAQG 244
    .|.:.||||:|::|| .||:   ||.||:||..:..  .|||||:|| .
194 PETAGANNTLHNDLCTAFEEGPYSTIGDDAQDTYLSTFAGPITARVNA.N 242

245 FKGVTLSNTDVLSLMDLCPFDTVAYPLSSLTTTSSVSGGGK.LSPFCSLF 293
    :.|..|.:.|.:.|||||||:|||  . |-  .|.....:|.|: |||||.||
243 LPGANLTDADTVALMDLCPFETVASSSSDPATADAGGGNGRPLSPFCRLF 292

294 TASDWTIYDYLQSLGKYYGFGPGNSLAATQGVGYVNELIARLIRAPVVDH 343
    ..|:|  |||||||:||:|||||.|::|||||:||||:|||  .|| |
293 SESEWRAYDYLQSVGKWYGYGPGNPLGPTQGVGFVNELLARLAGVPVRDG 342

344 TTTNSTLDGDEKTFPLNRTVYADFSHDNDMMNILTALRIFEHISPMDNTT 393
    |.||.||||.:||||.|..:|||||||||||..:|.||  ::  :.|:|
343 TSTNRTLDGDPRTFPLGRPLYADFSHDNDMMGVLGALGAYDGVPPLD... 389

394 IPTNYGQTGDDGVKERDLFKVSWAVPFAGRVYFEKMVCDADGDGKIDSD. 442
    .|:   :..|  : :   .||||||:|:|.|||  |.::|:|  :::
390 ......KTARRDPEELGGYAASWAVPFAARIYVEKMRCSGGGGGGGGGEG 433

443 ..EAQKELVRILVNDRVMRLNGCDADEQGRCGLEKFVESMEFARRGGEWE 490
    | :.|:||:||||||||.|.||:|||.|.|.||:|||:|||.|||  .|.|:
434 RQEKDEEMVRVLVNDRVMTLKGCGADERGMCTLERFIESMAFARGNGKWD 483

491 ERCFV 495
    ||.
484 L.CFA 487
```

Fig. 4A

```
Peniophora numbers        1                                              37
Alignment numbers     1                                                  50
      P_involtus_A1   ........ML FGFVALACLL SLSEVLATSV P......KNT APTFPIPESE
      P_involtus_A2   ........MH LGFVTLACLI HLSEVFAASV P......RNI APKFSIPESE
         T_pubescens  .......... MAFSILASLL FVCYAYARAV PRAHIPLRDT SACLDVTRDV
          A_pediades  .......... MSLFIGGCLL VFLQASAYGG VVQATFVQPF .....FPPQI
              P_lycii ........MV SSAFAPSILL SLMSSLALST QFSF.....V AAQLPIPAQN
          A_fumigatus ......MVTL TFLLSAAYLL .SGRVSAAPS SAGSKSCDTV DLGYQCSPAT
             conspyA  ......MGVF VVLLSIATLF GSTSGTALGP RGNSHSCDTV DGGYQCFPEI
          A_nidulans  ......MAFF TVALSLYYLL ..SRVSAQAP VVQNHSCNTA DGGYQCFPNV
    A_ficuum_NRRL3135 ......MGVS AVLLPLYLLS GVTSGLAVPA SRNQSSCDTV DQGYQCFSET
            A_terreus ......MGFL AIVLSVALLF RSTSGTPLGP RGKHSDCNSV DHGYQCFPEL
             T_thermo ......MSLL LLVLSGGLVA LYVS...RNP HVDSHSCNTV EGGYQCRPEI
         T_lanuginosa MAGIGLGSFL VLLLQFSALL TASPAIPPFW RKKHPNVD.. .........I
        M_thermophila ......MTGL GVMVVMVGFL AIASL..... QSESRPCDTP DLGFQCGTAI
       C_foecundissimum ........ML ILMIPLFSYL AAASL      RVLSPSCDSP ELGYQCDQQT
                                                                    QPV 38                                                 83
                  51                                                    100
      P_involtus_A1   QRNWSPYSPY FPLAEYKA.. ..PPAGCQIN QVNIIQRHGA RFPTSGATTR
      P_involtus_A2   QRNWSPYSPY FPLAEYKA.. ..PPAGCEIN QVNIIQRHGA RFPTSGAATR
         T_pubescens  QQSWSMYSPY FPAATYVA.. ..PPASCQIN QVHIIQRHGA RFPTSGAAKR
          A_pediades  QDSWAAYTPY YPVQAYTP.. ..PPKDCKIT QVNIIQRHGA RFPTSGAGTR
              P_lycii TSNWGPYDPF FPVEPYAA.. ..PPEGCTVT QVNLIQRHGA RWPTSGARSR
          A_fumigatus SHLWGQYSPF FSLEDELSVS SKLPKDCRIT LVQVLSRHGA RYPTSSKSKK
             conspyA  SHLWGQYSPY FSLEDESAIS PDVPDDCRVT FVQVLSRHGA RYPTSSKSKA
          A_nidulans  SHVWGQYSPY FSIEQESAIS EDVPHGCEVT FVQVLSRHGA RYPTESKSKA
    A_ficuum_NRRL3135 SHLWGQYAPF FSLANESVIS PEVPAGCRVT FAQVLSRHGA RYPTDSKGKK
            A_terreus SHKWGLYAPY FSLQDESPFP LDVPEDCHIT FVQVLARHGA RSPTHSKTKA
             T_thermo SHSWGQYSPF FSLADQSEIS PDVPQNCKIT FVQLLSRHGA RYPTSSKTEL
         T_lanuginosa ARHWGQYSPF FSLAEVSEIS PAVPKGCRVE FVQVLSRHGA RYPTAHKSEV
        M_thermophila SHFWGQYSPY FSVP..SELD ASIPDDCEVT FAQVLSRHGA RAPTLKRAAS
                       THTWGQYSPF FSVP  SEIS PSVPDGCRLT FAQVLSRHGA RFPTPGKAAA 84                                                133
                 101                                                    150
      P_involtus_A1   IKAGLTKLQG VQNFTDAKFN FIKSFKYDLG NSDLVPFGAA QSFDAGQEAF
      P_involtus_A2   IKAGLSKLQS VQNFTDPKFD FIKSFTYDLG TSDLVPFGAA QSFDAGLEVF
         T_pubescens  IQTAVAKLKA ASNYTDPLLA FVTNYTYSLG QDSLVELGAT QSSEAGQEAF
          A_pediades  IQAAVKKLQS AKTYTDPRLD FLTNYTYTLG HDDLVPFGAL QSSQAGEETF
              P_lycii QVAAVAKIQM ARPFTDPKYE FLNDFVYKFG VADLLPFGAN QSHQTGTDMY
          A_fumigatus YKKLVTAIQA NATDFKGKFA FLKTYNYTLG ADDLTPFGEQ QLVNSGIKFY
             conspyA  YSALIEAIQK NATAFKGKYA FLKTYNYTLG ADDLTPFGEN QMVNSGIKFY
          A_nidulans  YSGLIEAIQK NATSFWGQYA FLESYNYTLG ADDLTIFGEN QMVDSGAKFY
    A_ficuum_NRRL3135 YSALIEEIQQ NATTFDGKYA FLKTYNYSLG ADDLTPFGEQ ELVNSGIKFY
            A_terreus YAATIAAIQK SATAFPGKYA FLQSYNYSLD SEELTPFGRN QLRDLGAQFY
             T_thermo YSQLISRIQK TATAYKGYYA FLKDYRYQLG ANDLTPFGEN QMIQLGIKFY
         T_lanuginosa YAELLQRIQD TATEFKGDFA FLRDYAYHLG ADNLTRFGEE QMMESGRQFY
        M_thermophila YVDLIDRIHH GAISYGPGYE FLRTYDYTLG ADELTRTGQQ QMVNSGIKFY
                       ISAVLTKIKT SATWYGSDFQ FIKNYDYVLG VDHLTAFGEQ EMVNSGIKFY
```

Fig. 4B

```
                                134                                              176
                                151                                              200
    P_involtus_A1   ARYSKLVSKN NLPFIRADGS DRVVDSATNW TAGFASA...  ....SHNTVQ
    P_involtus_A2   ARYSKLVSSD NLPFIRSDGS DRVVDTATNW TAGFASA...  ....SRNAIQ
       T_pubescens  TRYSSLVSAD ELPFVRASGS DRVVATANNW TAGFALA...  ....SSNSIT
        A_pediades  QRYSFLVSKE NLPFVRASSS NRVVDSATNW TEGFSAA...  ....SHHVLN
            P_lycii TRYSTLFEGG DVPFVRAAGD QRVVDSSTNW TAGFGDA...  ....SGETVL
        A_fumigatus QRYKAL.ARS VVPFIRASGS DRVIASGEKF IEGFQQAKLA DPGA.TNRAA
          consphyA  RRYKAL.ARK IVPFIRASGS DRVIASAEKF IEGFQSAKLA DPGSQPHQAS
         A_nidulans RRYKNL.ARK NTPFIRASGS DRVVASAEKF INGFRKAQLH DHGS..KRAT
 A_ficuum_NRRL3135  QRYESL.TRN IVPFIRSSGS SRVIASGKKF IEGFQSTKLK DPRAQPGQSS
         A_terreus ERYNAL.TRH INPFVRATDA SRVHESAEKF VEGFQTARQD DHHANPHQPS
          T_thermo  NHYKSL.ARN AVPFVRCSGS DRVIASGRLF IEGFQSAKVL DPHSDKHDAP
       T_lanuginosa HRYREQ.ARE IVPFVRAAGS ARVIASAEFF NRGFQDAKDR DPRSNKDQAE
       M_thermophila RRYRAL.ARK SIPFVRTAGQ DRVVHSAENF TQGFHSALLA DRGSTVRPTL
                    QRYSSLIDSD TLPFVRASGQ ERVIASAENF TTGFYSALSA DKNPPSSLPR
                    QTE 177                                            217
                                201                                            250
    P_involtus_A1   PKLNLILPQT G..NDTLEDN MCPAAGD...  ...SDPQVNA WLAVAFPSIT
    P_involtus_A2   PKLDLILPQT G..NDTLEDN MCPAAGE...  ...SDPQVDA WLASAFPSVT
       T_pubescens  PVLSVIISEA G..NDTLDDN MCPAAGD...  ...SDPQVNQ WLAQFAPPMT
        A_pediades  PILFVILSES L..NDTLDDA MCPNAGS...  ...SDPQTGI WTSIYGTPIA
            P_lycii PTLQVVLQEE G..NCTLCNN MCPNEVD...  ...GD.ESTT WLGVFAPNIT
        A_fumigatus PAISVIIPES ETFNNTLDHG VCTKFEA...  SQLGDEVAAN FTALFAPDIR
          consphyA  PVIDVIIPEG SGYNNTLDHG TCTAFED...  SELGDDVEAN FTALFAPAIR
         A_nidulans PVVNVIIPEI DGFNNTLDHS TCVSFEN...  DERADEIEAN FTAIMGPPIR
 A_ficuum_NRRL3135  PKIDVVISEA SSSNNTLDPG TCTVFED...  SELADTVEAN FTATFVPSIR
         A_terreus PRVDVAIPEG SAYNNTLEHS LCTAFES...  STVGDDAVAN FTAVFAPAIA
          T_thermo  PTINVIIEEG PSYNNTLDTG SCPVFED...  SSGGHDAQEK FAKQFAPAIL
       T_lanuginosa PVINVIISEE TGSNNTLDGL TCPAAEE... AP.DPTQPAE FLQVFGPRVL
       M_thermophila PYDMVVIPET AGANNTLHND LCTAFEEGPY STIGDDAQDT YLSTFAGPIT
                    P.EMVIISEE PTANNTMHHG LCRSFED     STTGDQAQAE FIAATFPPIT 218                                          252
                                251                                          300
    P_involtus_A1   ARLNAAAPSV NLTDTDAFNL VSLCAFLTVS KEKK......  ..........S
    P_involtus_A2   AQLNAAAPGA NLTDADAFNL VSLCPFMTVS KEQK......  ..........S
       T_pubescens  ARLNAGAPGA NLTDTDTYNL LTLCPFETVA TERR......  ..........S
        A_pediades  NRLNQQAPGA NITAADVSNL IPLCAFETIV KETP......  ..........S
            P_lycii ARLNAAAPSA NLSDSDALTL MDMCPFDTLS SGNA......  ..........S
        A_fumigatus ARAEKHLPGV TLTDEDVVSL MDMCSFDTVA RTSD..ASQ.  ........LS
          consphyA  ARLEADLPGV TLTDEDVVYL MDMCPFETVA RTSD..ATE.  ........LS
         A_nidulans KRLENDLPGI KLTNENVIYL MDMCSFDTMA RTAH..GTE.  ........LS
 A_ficuum_NRRL3135  QRLENDLSGV TLTDTEVTYL MDMCSFDTIS TSTV..DTK.  ........LS
         A_terreus QRLEADLPGV QLSTDDVVNL MAMCPFETVS LTDD..AHT.  ........LS
          T_thermo  EKIKDHLPGV DLAVSDVPYL MDLCPFETLA RNHT..DT..  ........LS
       T_lanuginosa KKITKHMPGV NLTLEDVPLF MDLCPFDTVG SDPVLFPRQ.  ........LS
       M_thermophila ARVNANLPGA NLTDADTVAL MDLCPFETVA SSSSDPATAD AGGGNGRPLS
                    ARLNAGFKGV TLSNTDVLSL MDLCPFDTVA YPLSSLTTTS SVSGGGK LS
                    Q
```

Fig. 4C

```
                            253                                                        300
                            301                                                        350
  P_involtus_A1   DFCTLFEGIP GSFEAFAYGG DLDKFYGTGY GQELGPVQGV GYVNELIARL
  P_involtus_A2   DFCTLFEGIP GSFEAFAYAG DLDKFYGTGY GQALGPVQGV GYINELLARL
     T_pubescens  EFCDIYEELQ AE.DAFAYNA DLDKFYGTGY GQPLGPVQGV GYINELIARL
      A_pediades  PFCNLFT..P EEFAQFEYFG DLDKFYGTGY GQPLGPVQGV GYINELIARL
          P_lycii PFCDLFT..A EEYVSYEYYY DLDKYYGTGP GNALGPVQGV GYVNELLARL
     A_fumigatus  PFCQLFT..H NEWKKYNYLQ SLGKYYGYGA GNPLGPAQGI GFTNELIARL
        consphyA  PFCALFT..H DEWRQYDYLQ SLGKYYGYGA GNPLGPAQGV GFANELIARL
      A_nidulans  PFCAIFT..E KEWLQYDYLQ SLSKYYGYGA GSPLGPAQGI GFTNELIARL
A_ficuum_NRRL3135 PFCDLFT..H DEWINYDYLQ SLKKYYGHGA GNPLGPTQGV GYANELIARL
        A_terreus PFCDLFT..A TEWTQYNYLL SLDKYYGYGG GNPLGPVQGV GWANELMARL
         T_thermo PFCALST..Q EEWQAYDYYQ SLGKYYGNGG GNPLGPAQGV GFVNELIARM
      T_lanuginosa PFCHLFT..A DDWMAYDYYY TLDKYYSHGG GSAFGPSRGV GFVNELIARM
     M_thermophila PFCRLFS..E SEWRAYDYLQ SVGKWYGYGP GNPLGPTQGV GFVNELLARL
                   PFCSLFT  A SDWTIYDYLQ SLGKYYGFGP GNSLAATQGV GYVNELIARL 301                                                        349
                            351                                                        400
  P_involtus_A1   TNS.AVRDNT QTNRTLDASP VTFPLNKTFY ADFSHDNLMV AVFSAMGLFR
  P_involtus_A2   TNS.AVNDNT QTNRTLDAAP DTFPLNKTMY ADFSHDNLMV AVFSAMGLFR
     T_pubescens  TAQ.NVSDHT QTNSTLDSSP ETFPLNRTLY ADFSHDNQMV AIFSAMGLFN
      A_pediades  TEM.PVRDNT QTNRTLDSSP LTFPLDRSIY ADLSHDNQMI AIFSAMGLFN
          P_lycii TGQ.AVRDET QTNRTLDSDP ATFPLNRTFY ADFSHDNTMV PIFAALGLFN
     A_fumigatus  TRS.PVQDHT STNSTLVSNP ATFPLNATMY VDFSHDNSMV SIFFALGLYN
        consphyA  TRS.PVQDHT STNHTLDSNP ATFPLNATLY ADFSHDNSMI SIFFALGLYN
      A_nidulans  TQS.PVQDNT STNHTLDSNP ATFPLDRKLY ADFSHDNSMI SIFFAMGLYN
A_ficuum_NRRL3135 THS.PVHDDT SSNHTLDSSP ATFPLKSTLY ADFSHDNGII SILFALGLYN
        A_terreus TRA.PVHDHT CVNNTLDASP ATFPLNATLY ADFSHDSNLV SIFWALGLYN
         T_thermo THS.PVQDYT TVNHTLDSNP ATFPLNATLY ADFSHDNTMT SIFAALGLYN
     T_lanuginosa TGNLPVKDHT TVNHTLDDNP ETFPLDAVLY ADFSHDNTMT GIFSAMGLYN
    M_thermophila A.GVPVRDGT STNRTLDGDP RTFPLGRPLY ADFSHDNDMM GVLGALGAYD
                  I  RAPVVDHT TTNSTLDGDE KTFPLNRTVY ADFSHDNDMM NILTALRIFE 350                                 383
                            401                                                        450
  P_involtus_A1   QPAPLSTSVP NPWR.....T WRTSSLVPFS GRMVVERLSC ..........
  P_involtus_A2   QSAPLSTSTP DPNR.....T WLTSSVVPFS ARMAVERLSC ..........
     T_pubescens  QSAPLDPTTP DPAR.....T FLVKKIVPFS ARMVVERLDC ..........
      A_pediades  QSSPLDPSFP NPKR.....T WVTSRLTPFS ARMVTERLLC QRDGTGSGGP
          P_lycii ATA.LDPLKP DENR.....L WVDSKLVPFS GHMTVEKLAC ..........
     A_fumigatus  GTEPLSRTSV ESAKE..LDG YSASWVVPFG ARAYFETMQC ..........
        consphyA  GTAPLSTTSV ESIEE..TDG YSASWTVPFG ARAYVEMMQC ..........
      A_nidulans  GTQPLSMDSV ESIQE..MDG YAASWTVPFG ARAYFELMQC ..........
A_ficuum_NRRL3135 GTKPLSTTTV ENITQ..TDG FSSAWTVPFA SRLYVEMMQC ..........
        A_terreus GTAPLSQTSV ESVSQ..TDG YAAAWTVPFA ARAYVEMMQC ..........
         T_thermo GTAKLSTTEI KSIEE..TDG YSAAWTVPFG GRAYIEMMQC ..........
     T_lanuginosa GTKPLSTSKI QPPTGAAADG YAASWTVPFA ARAYVELLRC ETETSSEEEE
    M_thermophila GVPPLDKTAR RDPEE..LGG YAASWAVPFA ARIYVEKMRC SGGGGGGGGG
                  HISPMDQTGD DGVKE   RDL FKVSWAVPFA GRVYFEKMVC DADGDGKIDS
                           NTTIPTNYG
```

Fig. 4D

```
                           384                                                                425
                  451                                                                                   500
 P_involtus_A1    .......FGT TKVRVLVQDQ VQPLEFCGGD RNGLCTLAKF VESQTFARSD
 P_involtus_A2    .......AGT TKVRVLVQDQ VQPLEFCGGD QDGLCALDKF VESQAYARSG
     T_pubescens  .......GGA QSVRLLVNDA VQPLAFCGAD TSGVCTLDAF VESQAYARND
      A_pediades  SRIMRNGNVQ TFVRILVNDA LQPLKFCGGD MDSLCTLEAF VESQKYARED
         P_lycii  .......SGK EAVRVLVNDA VQPLEFCGG. VDGVCELSAF VESQTYAREN
     A_fumigatus  K..S...EKE PLVRALINDR VVPLHGCDVD KLGRCKLNDF VKGLSWARSG
        conSphyA  Q..A...EKE PLVRVLVNDR VVPLHGCAVD KLGRCKRDDF VEGLSFARSG
      A_nidulans  E......KKE PLVRVLVNDR VVPLHGCAVD KFGRCTLDDW VEGLNFARSG
A_ficuum_NRRL3135 Q..A...EQA PLVRVLVNDR VVPLHGCPVD ALGRCTRDSF VRGLSFARSG
       A_terreus  R..A...EKE PLVRVLVNDR VMPLHGCPTD KLGRCKRDAF VAGLSFAQAG
         T_thermo D..D...SDE PVVRVLVNDR VVPLHGCEVD SLGRCKRDDF VRGLSFARQG
     T_lanuginosa E..G...EDE PFVRVLVNDR VVPLHGCRVD RWGRCRRDEW IKGLTFARQG
    M_thermophila E..GRQEKDE EMVRVLVNDR VMTLKGCGAD ERGMCTLERF IESMAFARGN
                  D       EAQK ELVRILVNDR VMRLNGCDAD EQGRCGLEKF VESMEFARRG 426       439
                  501       514
 P_involtus_A1    GAGDFEKCFA TSA.
 P_involtus_A2    GAGDFEKCLA TTV.
     T_pubescens  GEGDFEKCFA T...
      A_pediades  GQGDFEKCFD ....
         P_lycii  GQGDFAKCGF VPSE
     A_fumigatus  ..GNWGECFS ....
        conSphyA  ..GNWAECFA *...
      A_nidulans  ..GNWKTCFT L...
A_ficuum_NRRL3135 ..GDWAECFA ....
       A_terreus  ..GNWADCF. ....
         T_thermo ..GNWEGCYA ASE.
     T_lanuginosa ..GHWDRCF. ....
    M_thermophila ..GKWDLCFA ....
                  GEWEECFV
                  R
```

SEQUENCE LISTING

```
<160> NUMBER OF SEQ ID NOS: 15

<210> SEQ ID NO 1
<211> LENGTH: 1570
<212> TYPE: DNA
<213> ORGANISM: Cladorrhinum foecundissimum
<220> FEATURE:
<221> NAME/KEY: intron
<222> LOCATION: (71)...(126)
<220> FEATURE:
<221> NAME/KEY: CDS
<222> LOCATION: (20)...(70)
<220> FEATURE:
<221> NAME/KEY: CDS
<222> LOCATION: (127)...(1563)
<220> FEATURE:
<221> NAME/KEY: sig_peptide
<222> LOCATION: (20)...(64)

<400> SEQUENCE: 1
aagcttgggc aaactcatc atg ctc atc ttg atg att cca ctg ttc agc tac      52
                     Met Leu Ile Leu Met Ile Pro Leu Phe Ser Tyr
                     -15                 -10                 -5 ctg gct gct gct tct ctg tgggttcatc ctttgcccct gtctcgatgt             100
Leu Ala Ala Ala Ser Leu
                1 taaaatacta aacatatttc accaga cgt gta ctc tcc cct cag cca gtg tcc     153
                             Arg Val Leu Ser Pro Gln Pro Val Ser
                                          5                  10 tgt gac agc ccg gag ctt ggt tac caa tgc gac cag cag aca acg cac      201
Cys Asp Ser Pro Glu Leu Gly Tyr Gln Cys Asp Gln Gln Thr Thr His
             15                  20                  25 acc tgg ggt caa tac tca ccc ttc ttc tct gtc ccg tca gag atc tcc      249
Thr Trp Gly Gln Tyr Ser Pro Phe Phe Ser Val Pro Ser Glu Ile Ser
         30                  35                  40 cct tcc gtt cct gat ggc tgc cgc ctc acc ttc gcc caa gtt ctc tcc      297
Pro Ser Val Pro Asp Gly Cys Arg Leu Thr Phe Ala Gln Val Leu Ser
     45                  50                  55 cgc cac ggc gcc cgc ttc cca acc ccg ggt aaa gcc gcc gcc atc tcc      345
Arg His Gly Ala Arg Phe Pro Thr Pro Gly Lys Ala Ala Ala Ile Ser
 60                  65                  70                  75 gct gtc ctc acc aaa atc aaa acc tct gcc acc tgg tac ggt tcc gac      393
Ala Val Leu Thr Lys Ile Lys Thr Ser Ala Thr Trp Tyr Gly Ser Asp
                 80                  85                  90 ttt cag ttc atc aag aac tac gac tat gta ctt ggc gta gac cac ctg      441
Phe Gln Phe Ile Lys Asn Tyr Asp Tyr Val Leu Gly Val Asp His Leu
             95                 100                 105 acc gcg ttc ggc gag caa gaa atg gtc aac tcc ggc atc aag ttc tac      489
Thr Ala Phe Gly Glu Gln Glu Met Val Asn Ser Gly Ile Lys Phe Tyr
```

|     |     |     |     |     |     |     |     |     |     |     |     |     |     |     |     |      |
|---|---|---|---|---|---|---|---|---|---|---|---|---|---|---|---|---|
|     |     |     | 110 |     |     |     | 115 |     |     |     |     | 120 |     |     |     |      |
| cag | cgc | tac | tcc | tcc | ctc | atc | cag | aca | gaa | gac | tcg | gat | acg | ctc | ccc | 537  |
| Gln | Arg | Tyr | Ser | Ser | Leu | Ile | Gln | Thr | Glu | Asp | Ser | Asp | Thr | Leu | Pro |      |
|     | 125 |     |     |     | 130 |     |     |     |     | 135 |     |     |     |     |     |      |
| ttc | gtc | cgc | gcc | tct | ggc | cag | gaa | cgt | gtc | atc | gcc | tcc | gcc | gag | aac | 585  |
| Phe | Val | Arg | Ala | Ser | Gly | Gln | Glu | Arg | Val | Ile | Ala | Ser | Ala | Glu | Asn |      |
| 140 |     |     |     |     | 145 |     |     |     |     | 150 |     |     |     |     | 155 |      |
| ttc | acc | acc | ggc | ttc | tac | tcg | gcc | ctc | tca | gcc | gac | aag | aac | cct | cct | 633  |
| Phe | Thr | Thr | Gly | Phe | Tyr | Ser | Ala | Leu | Ser | Ala | Asp | Lys | Asn | Pro | Pro |      |
|     |     |     | 160 |     |     |     |     | 165 |     |     |     |     | 170 |     |     |      |
| tcc | tcc | tta | cca | aga | cca | gaa | atg | gtc | atc | att | tct | gag | gag | cca | aca | 681  |
| Ser | Ser | Leu | Pro | Arg | Pro | Glu | Met | Val | Ile | Ile | Ser | Glu | Glu | Pro | Thr |      |
|     |     | 175 |     |     |     |     | 180 |     |     |     |     | 185 |     |     |     |      |
| gcc | aac | aac | acc | atg | cac | cac | ggc | ctc | tgc | cgc | tcc | ttt | gaa | gat | tcc | 729  |
| Ala | Asn | Asn | Thr | Met | His | His | Gly | Leu | Cys | Arg | Ser | Phe | Glu | Asp | Ser |      |
|     |     | 190 |     |     |     |     | 195 |     |     |     |     | 200 |     |     |     |      |
| acc | acc | ggc | gac | caa | gcc | caa | gcg | gaa | ttc | atc | gcc | gcc | acc | ttc | cca | 777  |
| Thr | Thr | Gly | Asp | Gln | Ala | Gln | Ala | Glu | Phe | Ile | Ala | Ala | Thr | Phe | Pro |      |
|     | 205 |     |     |     |     | 210 |     |     |     |     | 215 |     |     |     |     |      |
| ccc | atc | acc | gcc | cgt | ctc | aac | gcc | caa | ggt | ttc | aaa | ggc | gtc | acc | ctc | 825  |
| Pro | Ile | Thr | Ala | Arg | Leu | Asn | Ala | Gln | Gly | Phe | Lys | Gly | Val | Thr | Leu |      |
| 220 |     |     |     |     | 225 |     |     |     |     | 230 |     |     |     |     | 235 |      |
| tcc | aac | acc | gac | gtc | cta | tca | cta | atg | gac | ctc | tgc | ccc | ttt | gac | acc | 873  |
| Ser | Asn | Thr | Asp | Val | Leu | Ser | Leu | Met | Asp | Leu | Cys | Pro | Phe | Asp | Thr |      |
|     |     |     | 240 |     |     |     |     | 245 |     |     |     |     | 250 |     |     |      |
| gtc | gcc | tac | ccc | ctt | tcc | tcc | ctc | acc | acc | acc | tct | tcc | gtt | tct | gga | 921  |
| Val | Ala | Tyr | Pro | Leu | Ser | Ser | Leu | Thr | Thr | Thr | Ser | Ser | Val | Ser | Gly |      |
|     |     |     |     | 255 |     |     |     |     | 260 |     |     |     |     | 265 |     |      |
| ggc | ggc | aag | tta | tcc | ccc | ttc | tgc | tct | ctt | ttc | act | gcc | agc | gac | tgg | 969  |
| Gly | Gly | Lys | Leu | Ser | Pro | Phe | Cys | Ser | Leu | Phe | Thr | Ala | Ser | Asp | Trp |      |
|     |     | 270 |     |     |     |     | 275 |     |     |     |     | 280 |     |     |     |      |
| aca | atc | tac | gat | tac | ctc | cag | tcc | cta | ggg | aaa | tac | tac | ggt | ttc | ggc | 1017 |
| Thr | Ile | Tyr | Asp | Tyr | Leu | Gln | Ser | Leu | Gly | Lys | Tyr | Tyr | Gly | Phe | Gly |      |
|     | 285 |     |     |     |     | 290 |     |     |     |     | 295 |     |     |     |     |      |
| ccc | ggt | aat | tcc | cta | gct | gcc | acc | cag | ggg | gta | ggg | tac | gtc | aac | gag | 1065 |
| Pro | Gly | Asn | Ser | Leu | Ala | Ala | Thr | Gln | Gly | Val | Gly | Tyr | Val | Asn | Glu |      |
| 300 |     |     |     |     | 305 |     |     |     |     | 310 |     |     |     |     | 315 |      |
| ctt | atc | gcc | cgc | ttg | atc | cgt | gct | ccc | gtc | gta | gat | cac | acg | acg | acc | 1113 |
| Leu | Ile | Ala | Arg | Leu | Ile | Arg | Ala | Pro | Val | Val | Asp | His | Thr | Thr | Thr |      |
|     |     |     | 320 |     |     |     |     | 325 |     |     |     |     | 330 |     |     |      |
| aac | tct | act | ctt | gat | ggc | gac | gaa | aaa | acg | ttt | ccg | ttg | aac | aga | acg | 1161 |
| Asn | Ser | Thr | Leu | Asp | Gly | Asp | Glu | Lys | Thr | Phe | Pro | Leu | Asn | Arg | Thr |      |
|     |     |     | 335 |     |     |     |     | 340 |     |     |     |     | 345 |     |     |      |
| gtg | tat | gcg | gat | ttt | tcc | cat | gat | aat | gat | atg | atg | aat | atc | ctg | act | 1209 |
| Val | Tyr | Ala | Asp | Phe | Ser | His | Asp | Asn | Asp | Met | Met | Asn | Ile | Leu | Thr |      |
|     |     | 350 |     |     |     |     | 355 |     |     |     |     | 360 |     |     |     |      |
| gct | ttg | cgg | ata | ttc | gag | cat | atc | agt | ccg | atg | gat | aac | acc | act | atc | 1257 |
| Ala | Leu | Arg | Ile | Phe | Glu | His | Ile | Ser | Pro | Met | Asp | Asn | Thr | Thr | Ile |      |
|     | 365 |     |     |     |     | 370 |     |     |     |     | 375 |     |     |     |     |      |
| ccg | acc | aac | tat | ggc | cag | aca | gga | gat | gac | ggg | gtg | aag | gaa | agg | gat | 1305 |
| Pro | Thr | Asn | Tyr | Gly | Gln | Thr | Gly | Asp | Asp | Gly | Val | Lys | Glu | Arg | Asp |      |
| 380 |     |     |     |     | 385 |     |     |     |     | 390 |     |     |     |     | 395 |      |
| ttg | ttc | aag | gtt | agt | tgg | gcg | gtg | ccc | ttt | gct | ggg | agg | gtg | tac | ttt | 1353 |
| Leu | Phe | Lys | Val | Ser | Trp | Ala | Val | Pro | Phe | Ala | Gly | Arg | Val | Tyr | Phe |      |
|     |     |     | 400 |     |     |     |     | 405 |     |     |     |     | 410 |     |     |      |
| gag | aaa | atg | gtt | tgt | gat | gcg | gat | ggg | gat | ggc | aag | att | gat | agt | gat | 1401 |
| Glu | Lys | Met | Val | Cys | Asp | Ala | Asp | Gly | Asp | Gly | Lys | Ile | Asp | Ser | Asp |      |
|     |     |     |     | 415 |     |     |     |     | 420 |     |     |     |     | 425 |     |      |
| gag | gct | cag | aaa | gag | ttg | gtg | agg | att | ttg | gtt | aat | gat | cgg | gtg | atg | 1449 |

```
Glu Ala Gln Lys Glu Leu Val Arg Ile Leu Val Asn Asp Arg Val Met
        430                 435                 440 aga ttg aat ggg tgt gat gct gat gaa cag ggt agg tgt gga ttg gag    1497
Arg Leu Asn Gly Cys Asp Ala Asp Glu Gln Gly Arg Cys Gly Leu Glu
        445                 450                 455 aag ttt gtg gag agt atg gag ttt gcg agg aga ggg ggg gag tgg gag    1545
Lys Phe Val Glu Ser Met Glu Phe Ala Arg Arg Gly Gly Glu Trp Glu
460                 465                 470                 475 gag agg tgt ttt gtt tag ctctaga                                    1570
Glu Arg Cys Phe Val *
                480

<210> SEQ ID NO 2
<211> LENGTH: 495
<212> TYPE: PRT
<213> ORGANISM: Cladorrhinum foecundissimum
<220> FEATURE:
<221> NAME/KEY: SIGNAL
<222> LOCATION: (1)...(15)

<400> SEQUENCE: 2

Met Leu Ile Leu Met Ile Pro Leu Phe Ser Tyr Leu Ala Ala Ser
1               5                   10                  15

Leu Arg Val Leu Ser Pro Gln Pro Val Ser Cys Asp Ser Pro Glu Leu
            20                  25                  30

Gly Tyr Gln Cys Asp Gln Gln Thr Thr His Thr Trp Gly Gln Tyr Ser
        35                  40                  45

Pro Phe Phe Ser Val Pro Ser Glu Ile Ser Pro Ser Val Pro Asp Gly
    50                  55                  60

Cys Arg Leu Thr Phe Ala Gln Val Leu Ser Arg His Gly Ala Arg Phe
65                  70                  75                  80

Pro Thr Pro Gly Lys Ala Ala Ile Ser Ala Val Leu Thr Lys Ile
                85                  90                  95

Lys Thr Ser Ala Thr Trp Tyr Gly Ser Asp Phe Gln Phe Ile Lys Asn
            100                 105                 110

Tyr Asp Tyr Val Leu Gly Val Asp His Leu Thr Ala Phe Gly Glu Gln
        115                 120                 125

Glu Met Val Asn Ser Gly Ile Lys Phe Tyr Gln Arg Tyr Ser Ser Leu
    130                 135                 140

Ile Gln Thr Glu Asp Ser Asp Thr Leu Pro Phe Val Arg Ala Ser Gly
145                 150                 155                 160

Gln Glu Arg Val Ile Ala Ser Ala Glu Asn Phe Thr Thr Gly Phe Tyr
                165                 170                 175

Ser Ala Leu Ser Ala Asp Lys Asn Pro Pro Ser Ser Leu Pro Arg Pro
            180                 185                 190

Glu Met Val Ile Ile Ser Glu Glu Pro Thr Ala Asn Asn Thr Met His
        195                 200                 205

His Gly Leu Cys Arg Ser Phe Glu Asp Ser Thr Thr Gly Asp Gln Ala
    210                 215                 220

Gln Ala Glu Phe Ile Ala Ala Thr Phe Pro Pro Ile Thr Ala Arg Leu
225                 230                 235                 240

Asn Ala Gln Gly Phe Lys Gly Val Thr Leu Ser Asn Thr Asp Val Leu
                245                 250                 255

Ser Leu Met Asp Leu Cys Pro Phe Asp Thr Val Ala Tyr Pro Leu Ser
            260                 265                 270

Ser Leu Thr Thr Thr Ser Ser Val Ser Gly Gly Gly Lys Leu Ser Pro
        275                 280                 285
```

```
Phe Cys Ser Leu Phe Thr Ala Ser Asp Trp Thr Ile Tyr Asp Tyr Leu
    290                 295                 300

Gln Ser Leu Gly Lys Tyr Tyr Gly Phe Gly Pro Gly Asn Ser Leu Ala
305                 310                 315                 320

Ala Thr Gln Gly Val Gly Tyr Val Asn Glu Leu Ile Ala Arg Leu Ile
                325                 330                 335

Arg Ala Pro Val Val Asp His Thr Thr Thr Asn Ser Thr Leu Asp Gly
                340                 345                 350

Asp Glu Lys Thr Phe Pro Leu Asn Arg Thr Val Tyr Ala Asp Phe Ser
                355                 360                 365

His Asp Asn Asp Met Met Asn Ile Leu Thr Ala Leu Arg Ile Phe Glu
    370                 375                 380

His Ile Ser Pro Met Asp Asn Thr Thr Ile Pro Thr Asn Tyr Gly Gln
385                 390                 395                 400

Thr Gly Asp Asp Gly Val Lys Glu Arg Asp Leu Phe Lys Val Ser Trp
                405                 410                 415

Ala Val Pro Phe Ala Gly Arg Val Tyr Phe Glu Lys Met Val Cys Asp
                420                 425                 430

Ala Asp Gly Asp Gly Lys Ile Asp Ser Asp Glu Ala Gln Lys Glu Leu
            435                 440                 445

Val Arg Ile Leu Val Asn Asp Arg Val Met Arg Leu Asn Gly Cys Asp
    450                 455                 460

Ala Asp Glu Gln Gly Arg Cys Gly Leu Glu Lys Phe Val Glu Ser Met
465                 470                 475                 480

Glu Phe Ala Arg Arg Gly Gly Glu Trp Glu Glu Arg Cys Phe Val
                485                 490                 495

<210> SEQ ID NO 3
<211> LENGTH: 478
<212> TYPE: PRT
<213> ORGANISM: Paxillus involtus

<400> SEQUENCE: 3

Arg Val Leu Ser Pro Gln Pro Val Ser Cys Asp Ser Pro Glu Leu Gly
1               5                   10                  15

Tyr Gln Cys Asp Gln Gln Thr Thr His Thr Trp Gly Gln Tyr Ser Pro
                20                  25                  30

Phe Phe Ser Val Pro Ser Glu Ile Ser Pro Ser Val Pro Asp Gly Cys
            35                  40                  45

Arg Leu Thr Phe Ala Gln Val Leu Ser Arg His Gly Ala Arg Phe Pro
    50                  55                  60

Thr Pro Gly Lys Ala Ala Ala Ile Ser Ala Val Leu Thr Lys Ile Lys
65                  70                  75                  80

Thr Ser Ala Thr Trp Tyr Gly Ser Asp Phe Gln Phe Ile Lys Asn Tyr
                85                  90                  95

Asp Tyr Val Leu Gly Val Asp His Leu Thr Ala Phe Gly Glu Gln Glu
                100                 105                 110

Met Val Asn Ser Gly Ile Lys Phe Tyr Gln Arg Tyr Ser Ser Leu Ile
            115                 120                 125

Gln Thr Glu Asp Ser Asp Thr Leu Pro Phe Val Arg Ala Ser Gly Gln
    130                 135                 140

Glu Arg Val Ile Ala Ser Ala Glu Asn Phe Thr Thr Gly Phe Tyr Ser
145                 150                 155                 160

Ala Leu Ser Ala Asp Lys Asn Pro Pro Ser Ser Leu Pro Arg Pro Glu
```

```
                165                 170                 175
Met Val Ile Ile Ser Glu Glu Pro Thr Ala Asn Asn Thr Met His His
                180                 185                 190

Gly Leu Cys Arg Ser Phe Glu Asp Ser Thr Thr Gly Asp Gln Ala Gln
                195                 200                 205

Ala Glu Phe Ile Ala Ala Thr Phe Pro Pro Ile Thr Ala Arg Leu Asn
        210                 215                 220

Ala Gln Gly Phe Lys Gly Val Thr Leu Ser Asn Thr Asp Val Leu Ser
225                 230                 235                 240

Leu Met Asp Leu Cys Pro Phe Asp Thr Val Ala Tyr Pro Leu Ser Ser
                245                 250                 255

Leu Thr Thr Thr Ser Ser Val Ser Gly Gly Lys Leu Ser Pro Phe
                260                 265                 270

Cys Ser Leu Phe Thr Ala Ser Asp Trp Thr Ile Tyr Asp Tyr Leu Gln
                275                 280                 285

Ser Leu Gly Lys Tyr Tyr Gly Phe Gly Pro Gly Asn Ser Leu Ala Ala
            290                 295                 300

Thr Gln Gly Val Gly Tyr Val Asn Glu Leu Ile Ala Arg Leu Ile Arg
305                 310                 315                 320

Ala Pro Val Val Asp His Thr Thr Asn Ser Thr Leu Asp Gly Asp
                325                 330                 335

Glu Lys Thr Phe Pro Leu Asn Arg Thr Val Tyr Ala Asp Phe Ser His
                340                 345                 350

Asp Asn Asp Met Met Asn Ile Leu Thr Ala Leu Arg Ile Phe Glu His
                355                 360                 365

Ile Ser Pro Met Asp Asn Thr Thr Ile Pro Thr Asn Tyr Gly Gln Thr
        370                 375                 380

Gly Asp Asp Gly Val Lys Glu Arg Asp Leu Phe Lys Val Ser Trp Ala
385                 390                 395                 400

Val Pro Phe Ala Gly Arg Val Tyr Phe Glu Lys Met Val Cys Asp Ala
                405                 410                 415

Asp Gly Asp Gly Lys Ile Asp Ser Asp Glu Ala Gln Lys Glu Leu Val
                420                 425                 430

Arg Ile Leu Val Asn Asp Arg Val Met Arg Leu Asn Gly Cys Asp Ala
                435                 440                 445

Asp Glu Gln Gly Arg Cys Gly Leu Glu Lys Phe Val Glu Ser Met Glu
                450                 455                 460

Phe Ala Arg Arg Gly Gly Glu Trp Glu Glu Arg Cys Phe Val
465                 470                 475

<210> SEQ ID NO 4
<211> LENGTH: 442
<212> TYPE: PRT
<213> ORGANISM: Paxillus involtus

<400> SEQUENCE: 4

Met His Leu Gly Phe Val Thr Leu Ala Cys Leu Ile His Leu Ser Glu
1               5                   10                  15

Val Phe Ala Ala Ser Val Pro Arg Asn Ile Ala Pro Lys Phe Ser Ile
                20                  25                  30

Pro Glu Ser Glu Gln Arg Asn Trp Ser Pro Tyr Ser Pro Tyr Phe Pro
            35                  40                  45

Leu Ala Glu Tyr Lys Ala Pro Pro Ala Gly Cys Glu Ile Asn Gln Val
        50                  55                  60
```

```
Asn Ile Ile Gln Arg His Gly Ala Arg Phe Pro Thr Ser Gly Ala Ala
 65                  70                  75                  80

Thr Arg Ile Lys Ala Gly Leu Ser Lys Leu Gln Ser Val Gln Asn Phe
             85                  90                  95

Thr Asp Pro Lys Phe Asp Phe Ile Lys Ser Phe Thr Tyr Asp Leu Gly
            100                 105                 110

Thr Ser Asp Leu Val Pro Phe Gly Ala Ala Gln Ser Phe Asp Ala Gly
            115                 120                 125

Leu Glu Val Phe Ala Arg Tyr Ser Lys Leu Val Ser Ser Asp Asn Leu
    130                 135                 140

Pro Phe Ile Arg Ser Asp Gly Ser Asp Arg Val Val Asp Thr Ala Thr
145                 150                 155                 160

Asn Trp Thr Ala Gly Phe Ala Ser Ala Ser Arg Asn Ala Ile Gln Pro
                165                 170                 175

Lys Leu Asp Leu Ile Leu Pro Gln Thr Gly Asn Asp Thr Leu Glu Asp
            180                 185                 190

Asn Met Cys Pro Ala Ala Gly Glu Ser Asp Pro Gln Val Asp Ala Trp
            195                 200                 205

Leu Ala Ser Ala Phe Pro Ser Val Thr Ala Gln Leu Asn Ala Ala Ala
    210                 215                 220

Pro Gly Ala Asn Leu Thr Asp Ala Asp Ala Phe Asn Leu Val Ser Leu
225                 230                 235                 240

Cys Pro Phe Met Thr Val Ser Lys Glu Gln Lys Ser Asp Phe Cys Thr
                245                 250                 255

Leu Phe Glu Gly Ile Pro Gly Ser Phe Glu Ala Phe Ala Tyr Ala Gly
            260                 265                 270

Asp Leu Asp Lys Phe Tyr Gly Thr Gly Tyr Gly Gln Ala Leu Gly Pro
            275                 280                 285

Val Gln Gly Val Gly Tyr Ile Asn Glu Leu Leu Ala Arg Leu Thr Asn
    290                 295                 300

Ser Ala Val Asn Asp Asn Thr Gln Thr Asn Arg Thr Leu Asp Ala Ala
305                 310                 315                 320

Pro Asp Thr Phe Pro Leu Asn Lys Thr Met Tyr Ala Asp Phe Ser His
                325                 330                 335

Asp Asn Leu Met Val Ala Val Phe Ser Ala Met Gly Leu Phe Arg Gln
            340                 345                 350

Ser Ala Pro Leu Ser Thr Ser Thr Pro Asp Pro Asn Arg Thr Trp Leu
            355                 360                 365

Thr Ser Ser Val Val Pro Phe Ser Ala Arg Met Ala Val Glu Arg Leu
    370                 375                 380

Ser Cys Ala Gly Thr Thr Lys Val Arg Val Leu Val Gln Asp Gln Val
385                 390                 395                 400

Gln Pro Leu Glu Phe Cys Gly Gly Asp Gln Asp Gly Leu Cys Ala Leu
                405                 410                 415

Asp Lys Phe Val Glu Ser Gln Ala Tyr Ala Arg Ser Gly Gly Ala Gly
            420                 425                 430

Asp Phe Glu Lys Cys Leu Ala Thr Thr Val
            435                 440

<210> SEQ ID NO 5
<211> LENGTH: 443
<212> TYPE: PRT
<213> ORGANISM: Tremetes pubescens

<400> SEQUENCE: 5
```

```
Met Ala Phe Ser Ile Leu Ala Ser Leu Leu Phe Val Cys Tyr Ala Tyr
  1               5                  10                  15

Ala Arg Ala Val Pro Arg Ala His Ile Pro Leu Arg Asp Thr Ser Ala
             20                  25                  30

Cys Leu Asp Val Thr Arg Asp Val Gln Gln Ser Trp Ser Met Tyr Ser
         35                  40                  45

Pro Tyr Phe Pro Ala Ala Thr Tyr Val Ala Pro Ala Ser Cys Gln
     50                  55                  60

Ile Asn Gln Val His Ile Ile Gln Arg His Gly Ala Arg Phe Pro Thr
 65              70                  75                  80

Ser Gly Ala Ala Lys Arg Ile Gln Thr Ala Val Ala Lys Leu Lys Ala
                 85                  90                  95

Ala Ser Asn Tyr Thr Asp Pro Leu Leu Ala Phe Val Thr Asn Tyr Thr
                100                 105                 110

Tyr Ser Leu Gly Gln Asp Ser Leu Val Glu Leu Gly Ala Thr Gln Ser
        115                 120                 125

Ser Glu Ala Gly Gln Glu Ala Phe Thr Arg Tyr Ser Ser Leu Val Ser
130                 135                 140

Ala Asp Glu Leu Pro Phe Val Arg Ala Ser Gly Ser Asp Arg Val Val
145                 150                 155                 160

Ala Thr Ala Asn Asn Trp Thr Ala Gly Phe Ala Leu Ala Ser Ser Asn
                165                 170                 175

Ser Ile Thr Pro Val Leu Ser Val Ile Ile Ser Glu Ala Gly Asn Asp
            180                 185                 190

Thr Leu Asp Asp Asn Met Cys Pro Ala Ala Gly Asp Ser Asp Pro Gln
        195                 200                 205

Val Asn Gln Trp Leu Ala Gln Phe Ala Pro Pro Met Thr Ala Arg Leu
    210                 215                 220

Asn Ala Gly Ala Pro Gly Ala Asn Leu Thr Asp Thr Asp Thr Tyr Asn
225                 230                 235                 240

Leu Leu Thr Leu Cys Pro Phe Glu Thr Val Ala Thr Glu Arg Arg Ser
                245                 250                 255

Glu Phe Cys Asp Ile Tyr Glu Glu Leu Gln Ala Glu Asp Ala Phe Ala
            260                 265                 270

Tyr Asn Ala Asp Leu Asp Lys Phe Tyr Gly Thr Gly Tyr Gly Gln Pro
        275                 280                 285

Leu Gly Pro Val Gln Gly Val Gly Tyr Ile Asn Glu Leu Ile Ala Arg
    290                 295                 300

Leu Thr Ala Gln Asn Val Ser Asp His Thr Gln Thr Asn Ser Thr Leu
305                 310                 315                 320

Asp Ser Ser Pro Glu Thr Phe Pro Leu Asn Arg Thr Leu Tyr Ala Asp
                325                 330                 335

Phe Ser His Asp Asn Gln Met Val Ala Ile Phe Ser Ala Met Gly Leu
            340                 345                 350

Phe Asn Gln Ser Ala Pro Leu Asp Pro Thr Thr Pro Asp Pro Ala Arg
        355                 360                 365

Thr Phe Leu Val Lys Lys Ile Val Pro Phe Ser Ala Arg Met Val Val
    370                 375                 380

Glu Arg Leu Asp Cys Gly Gly Ala Gln Ser Val Arg Leu Leu Val Asn
385                 390                 395                 400

Asp Ala Val Gln Pro Leu Ala Phe Cys Gly Ala Asp Thr Ser Gly Val
                405                 410                 415
```

```
Cys Thr Leu Asp Ala Phe Val Glu Ser Gln Ala Tyr Ala Arg Asn Asp
            420                 425                 430

Gly Glu Gly Asp Phe Glu Lys Cys Phe Ala Thr
            435                 440

<210> SEQ ID NO 6
<211> LENGTH: 453
<212> TYPE: PRT
<213> ORGANISM: A grocybe pediades

<400> SEQUENCE: 6

Met Ser Leu Phe Ile Gly Gly Cys Leu Leu Val Phe Leu Gln Ala Ser
 1               5                  10                  15

Ala Tyr Gly Gly Val Val Gln Ala Thr Phe Val Gln Pro Phe Phe Pro
            20                  25                  30

Pro Gln Ile Gln Asp Ser Trp Ala Ala Tyr Thr Pro Tyr Tyr Pro Val
            35                  40                  45

Gln Ala Tyr Thr Pro Pro Lys Asp Cys Lys Ile Thr Gln Val Asn
 50                  55                  60

Ile Ile Gln Arg His Gly Ala Arg Phe Pro Thr Ser Gly Ala Gly Thr
 65                  70                  75                  80

Arg Ile Gln Ala Ala Val Lys Lys Leu Gln Ser Ala Lys Thr Tyr Thr
                85                  90                  95

Asp Pro Arg Leu Asp Phe Leu Thr Asn Tyr Thr Tyr Thr Leu Gly His
            100                 105                 110

Asp Asp Leu Val Pro Phe Gly Ala Leu Gln Ser Gln Ala Gly Glu
            115                 120                 125

Glu Thr Phe Gln Arg Tyr Ser Phe Leu Val Ser Lys Glu Asn Leu Pro
130                 135                 140

Phe Val Arg Ala Ser Ser Ser Asn Arg Val Val Asp Ser Ala Thr Asn
145                 150                 155                 160

Trp Thr Glu Gly Phe Ser Ala Ala Ser His His Val Leu Asn Pro Ile
                165                 170                 175

Leu Phe Val Ile Leu Ser Glu Ser Leu Asn Asp Thr Leu Asp Asp Ala
            180                 185                 190

Met Cys Pro Asn Ala Gly Ser Ser Asp Pro Gln Thr Gly Ile Trp Thr
            195                 200                 205

Ser Ile Tyr Gly Thr Pro Ile Ala Asn Arg Leu Asn Gln Gln Ala Pro
210                 215                 220

Gly Ala Asn Ile Thr Ala Ala Asp Val Ser Asn Leu Ile Pro Leu Cys
225                 230                 235                 240

Ala Phe Glu Thr Ile Val Lys Glu Thr Pro Ser Pro Phe Cys Asn Leu
                245                 250                 255

Phe Thr Pro Glu Glu Phe Ala Gln Phe Glu Tyr Phe Gly Asp Leu Asp
            260                 265                 270

Lys Phe Tyr Gly Thr Gly Tyr Gly Gln Pro Leu Gly Pro Val Gln Gly
            275                 280                 285

Val Gly Tyr Ile Asn Glu Leu Leu Ala Arg Leu Thr Glu Met Pro Val
            290                 295                 300

Arg Asp Asn Thr Gln Thr Asn Arg Thr Leu Asp Ser Ser Pro Leu Thr
305                 310                 315                 320

Phe Pro Leu Asp Arg Ser Ile Tyr Ala Asp Leu Ser His Asp Asn Gln
                325                 330                 335

Met Ile Ala Ile Phe Ser Ala Met Gly Leu Phe Asn Gln Ser Ser Pro
            340                 345                 350
```

-continued

```
Leu Asp Pro Ser Phe Pro Asn Pro Lys Arg Thr Trp Val Thr Ser Arg
            355                 360                 365

Leu Thr Pro Phe Ser Ala Arg Met Val Thr Glu Arg Leu Leu Cys Gln
        370                 375                 380

Arg Asp Gly Thr Gly Ser Gly Gly Pro Ser Arg Ile Met Arg Asn Gly
385                 390                 395                 400

Asn Val Gln Thr Phe Val Arg Ile Leu Val Asn Asp Ala Leu Gln Pro
                405                 410                 415

Leu Lys Phe Cys Gly Asp Met Asp Ser Leu Cys Thr Leu Glu Ala
            420                 425                 430

Phe Val Glu Ser Gln Lys Tyr Ala Arg Glu Asp Gly Gln Gly Asp Phe
        435                 440                 445

Glu Lys Cys Phe Asp
    450
```

<210> SEQ ID NO 7
<211> LENGTH: 439
<212> TYPE: PRT
<213> ORGANISM: Peniophora ycii

<400> SEQUENCE: 7

```
Met Val Ser Ser Ala Phe Ala Pro Ser Ile Leu Leu Ser Leu Met Ser
  1               5                  10                  15

Ser Leu Ala Leu Ser Thr Gln Phe Ser Phe Val Ala Ala Gln Leu Pro
             20                  25                  30

Ile Pro Ala Gln Asn Thr Ser Asn Trp Gly Pro Tyr Asp Pro Phe Phe
         35                  40                  45

Pro Val Glu Pro Tyr Ala Ala Pro Pro Glu Gly Cys Thr Val Thr Gln
     50                  55                  60

Val Asn Leu Ile Gln Arg His Gly Ala Arg Trp Pro Thr Ser Gly Ala
 65                  70                  75                  80

Arg Ser Arg Gln Val Ala Ala Val Ala Lys Ile Gln Met Ala Arg Pro
                 85                  90                  95

Phe Thr Asp Pro Lys Tyr Glu Phe Leu Asn Asp Phe Val Tyr Lys Phe
            100                 105                 110

Gly Val Ala Asp Leu Leu Pro Phe Gly Ala Asn Gln Ser His Gln Thr
        115                 120                 125

Gly Thr Asp Met Tyr Thr Arg Tyr Ser Thr Leu Phe Glu Gly Gly Asp
    130                 135                 140

Val Pro Phe Val Arg Ala Ala Gly Asp Gln Arg Val Val Asp Ser Ser
145                 150                 155                 160

Thr Asn Trp Thr Ala Gly Phe Gly Asp Ala Ser Gly Glu Thr Val Leu
                165                 170                 175

Pro Thr Leu Gln Val Val Leu Gln Glu Glu Gly Asn Cys Thr Leu Cys
            180                 185                 190

Asn Asn Met Cys Pro Asn Glu Val Asp Gly Asp Glu Ser Thr Thr Trp
        195                 200                 205

Leu Gly Val Phe Ala Pro Asn Ile Thr Ala Arg Leu Asn Ala Ala Ala
    210                 215                 220

Pro Ser Ala Asn Leu Ser Asp Ser Asp Ala Leu Thr Leu Met Asp Met
225                 230                 235                 240

Cys Pro Phe Asp Thr Leu Ser Ser Gly Asn Ala Ser Pro Phe Cys Asp
                245                 250                 255

Leu Phe Thr Ala Glu Glu Tyr Val Ser Tyr Glu Tyr Tyr Tyr Asp Leu
```

```
                260                 265                 270
Asp Lys Tyr Tyr Gly Thr Gly Pro Gly Asn Ala Leu Gly Pro Val Gln
            275                 280                 285

Gly Val Gly Tyr Val Asn Glu Leu Leu Ala Arg Leu Thr Gly Gln Ala
        290                 295                 300

Val Arg Asp Glu Thr Gln Thr Asn Arg Thr Leu Asp Ser Asp Pro Ala
305                 310                 315                 320

Thr Phe Pro Leu Asn Arg Thr Phe Tyr Ala Asp Phe Ser His Asp Asn
                325                 330                 335

Thr Met Val Pro Ile Phe Ala Ala Leu Gly Leu Phe Asn Ala Thr Ala
            340                 345                 350

Leu Asp Pro Leu Lys Pro Asp Glu Asn Arg Leu Trp Val Asp Ser Lys
        355                 360                 365

Leu Val Pro Phe Ser Gly His Met Thr Val Glu Lys Leu Ala Cys Ser
370                 375                 380

Gly Lys Glu Ala Val Arg Val Leu Val Asn Asp Ala Val Gln Pro Leu
385                 390                 395                 400

Glu Phe Cys Gly Gly Val Asp Gly Val Cys Glu Leu Ser Ala Phe Val
                405                 410                 415

Glu Ser Gln Thr Tyr Ala Arg Glu Asn Gly Gln Gly Asp Phe Ala Lys
            420                 425                 430

Cys Gly Phe Val Pro Ser Glu
            435

<210> SEQ ID NO 8
<211> LENGTH: 465
<212> TYPE: PRT
<213> ORGANISM: Aspergillus fumigatus

<400> SEQUENCE: 8

Met Val Thr Leu Thr Phe Leu Leu Ser Ala Ala Tyr Leu Leu Ser Gly
1               5                   10                  15

Arg Val Ser Ala Ala Pro Ser Ser Ala Gly Ser Lys Ser Cys Asp Thr
            20                  25                  30

Val Asp Leu Gly Tyr Gln Cys Ser Pro Ala Thr Ser His Leu Trp Gly
        35                  40                  45

Gln Tyr Ser Pro Phe Phe Ser Leu Glu Asp Glu Leu Ser Val Ser Ser
    50                  55                  60

Lys Leu Pro Lys Asp Cys Arg Ile Thr Leu Val Gln Val Leu Ser Arg
65                  70                  75                  80

His Gly Ala Arg Tyr Pro Thr Ser Ser Lys Ser Lys Tyr Lys Lys
                85                  90                  95

Leu Val Thr Ala Ile Gln Ala Asn Ala Thr Asp Phe Lys Gly Lys Phe
            100                 105                 110

Ala Phe Leu Lys Thr Tyr Asn Tyr Thr Leu Gly Ala Asp Asp Leu Thr
        115                 120                 125

Pro Phe Gly Glu Gln Gln Leu Val Asn Ser Gly Ile Lys Phe Tyr Gln
    130                 135                 140

Arg Tyr Lys Ala Leu Ala Arg Ser Val Val Pro Phe Ile Arg Ala Ser
145                 150                 155                 160

Gly Ser Asp Arg Val Ile Ala Ser Gly Glu Lys Phe Ile Glu Gly Phe
                165                 170                 175

Gln Gln Ala Lys Leu Ala Asp Pro Gly Ala Thr Asn Arg Ala Ala Pro
            180                 185                 190
```

```
Ala Ile Ser Val Ile Ile Pro Glu Ser Glu Thr Phe Asn Asn Thr Leu
            195                 200                 205

Asp His Gly Val Cys Thr Lys Phe Glu Ala Ser Gln Leu Gly Asp Glu
        210                 215                 220

Val Ala Ala Asn Phe Thr Ala Leu Phe Ala Pro Asp Ile Arg Ala Arg
225                 230                 235                 240

Ala Glu Lys His Leu Pro Gly Val Thr Leu Thr Asp Glu Asp Val Val
            245                 250                 255

Ser Leu Met Asp Met Cys Ser Phe Asp Thr Val Ala Arg Thr Ser Asp
            260                 265                 270

Ala Ser Gln Leu Ser Pro Phe Cys Gln Leu Phe Thr His Asn Glu Trp
            275                 280                 285

Lys Lys Tyr Asn Tyr Leu Gln Ser Leu Gly Lys Tyr Tyr Gly Tyr Gly
            290                 295                 300

Ala Gly Asn Pro Leu Gly Pro Ala Gln Gly Ile Gly Phe Thr Asn Glu
305                 310                 315                 320

Leu Ile Ala Arg Leu Thr Arg Ser Pro Val Gln Asp His Thr Ser Thr
            325                 330                 335

Asn Ser Thr Leu Val Ser Asn Pro Ala Thr Phe Pro Leu Asn Ala Thr
            340                 345                 350

Met Tyr Val Asp Phe Ser His Asp Asn Ser Met Val Ser Ile Phe Phe
            355                 360                 365

Ala Leu Gly Leu Tyr Asn Gly Thr Glu Pro Leu Ser Arg Thr Ser Val
            370                 375                 380

Glu Ser Ala Lys Glu Leu Asp Gly Tyr Ser Ala Ser Trp Val Val Pro
385                 390                 395                 400

Phe Gly Ala Arg Ala Tyr Phe Glu Thr Met Gln Cys Lys Ser Glu Lys
            405                 410                 415

Glu Pro Leu Val Arg Ala Leu Ile Asn Asp Arg Val Val Pro Leu His
            420                 425                 430

Gly Cys Asp Val Asp Lys Leu Gly Arg Cys Lys Leu Asn Asp Phe Val
            435                 440                 445

Lys Gly Leu Ser Trp Ala Arg Ser Gly Gly Asn Trp Gly Glu Cys Phe
    450                 455                 460

Ser
465

<210> SEQ ID NO 9
<211> LENGTH: 467
<212> TYPE: PRT
<213> ORGANISM: Artificial Sequence
<220> FEATURE:
<223> OTHER INFORMATION: Variation

<400> SEQUENCE: 9

Met Gly Val Phe Val Leu Leu Ser Ile Ala Thr Leu Phe Gly Ser
  1               5                  10                  15

Thr Ser Gly Thr Ala Leu Gly Pro Arg Gly Asn Ser His Ser Cys Asp
            20                  25                  30

Thr Val Asp Gly Gly Tyr Gln Cys Phe Pro Glu Ile Ser His Leu Trp
        35                  40                  45

Gly Gln Tyr Ser Pro Tyr Phe Ser Leu Glu Asp Glu Ser Ala Ile Ser
    50                  55                  60

Pro Asp Val Pro Asp Asp Cys Arg Val Thr Phe Val Gln Val Leu Ser
65                  70                  75                  80
```

```
Arg His Gly Ala Arg Tyr Pro Thr Ser Ser Lys Ser Lys Ala Tyr Ser
                85                  90                  95

Ala Leu Ile Glu Ala Ile Gln Lys Asn Ala Thr Ala Phe Lys Gly Lys
            100                 105                 110

Tyr Ala Phe Leu Lys Thr Tyr Asn Tyr Thr Leu Gly Ala Asp Asp Leu
            115                 120                 125

Thr Pro Phe Gly Glu Asn Gln Met Val Asn Ser Gly Ile Lys Phe Tyr
        130                 135                 140

Arg Arg Tyr Lys Ala Leu Ala Arg Lys Ile Val Pro Phe Ile Arg Ala
145                 150                 155                 160

Ser Gly Ser Asp Arg Val Ile Ala Ser Glu Lys Phe Ile Glu Gly
                165                 170                 175

Phe Gln Ser Ala Lys Leu Ala Asp Pro Gly Ser Gln Pro His Gln Ala
            180                 185                 190

Ser Pro Val Ile Asp Val Ile Ile Pro Glu Gly Ser Gly Tyr Asn Asn
        195                 200                 205

Thr Leu Asp His Gly Thr Cys Thr Ala Phe Glu Asp Ser Glu Leu Gly
        210                 215                 220

Asp Asp Val Glu Ala Asn Phe Thr Ala Leu Phe Ala Pro Ala Ile Arg
225                 230                 235                 240

Ala Arg Leu Glu Ala Asp Leu Pro Gly Val Thr Leu Thr Asp Glu Asp
                245                 250                 255

Val Val Tyr Leu Met Asp Met Cys Pro Phe Glu Thr Val Ala Arg Thr
            260                 265                 270

Ser Asp Ala Thr Glu Leu Ser Pro Phe Cys Ala Leu Phe Thr His Asp
        275                 280                 285

Glu Trp Arg Gln Tyr Asp Tyr Leu Gln Ser Leu Gly Lys Tyr Tyr Gly
        290                 295                 300

Tyr Gly Ala Gly Asn Pro Leu Gly Pro Ala Gln Gly Val Gly Phe Ala
305                 310                 315                 320

Asn Glu Leu Ile Ala Arg Leu Thr Arg Ser Pro Val Gln Asp His Thr
                325                 330                 335

Ser Thr Asn His Thr Leu Asp Ser Asn Pro Ala Thr Phe Pro Leu Asn
            340                 345                 350

Ala Thr Leu Tyr Ala Asp Phe Ser His Asp Asn Ser Met Ile Ser Ile
        355                 360                 365

Phe Phe Ala Leu Gly Leu Tyr Asn Gly Thr Ala Pro Leu Ser Thr Thr
    370                 375                 380

Ser Val Glu Ser Ile Glu Glu Thr Asp Gly Tyr Ser Ala Ser Trp Thr
385                 390                 395                 400

Val Pro Phe Gly Ala Arg Ala Tyr Val Glu Met Met Gln Cys Gln Ala
                405                 410                 415

Glu Lys Glu Pro Leu Val Arg Val Leu Val Asn Asp Arg Val Pro
            420                 425                 430

Leu His Gly Cys Ala Val Asp Lys Leu Gly Arg Cys Lys Arg Asp Asp
        435                 440                 445

Phe Val Glu Gly Leu Ser Phe Ala Arg Ser Gly Gly Asn Trp Ala Glu
    450                 455                 460

Cys Phe Ala
465

<210> SEQ ID NO 10
<211> LENGTH: 463
<212> TYPE: PRT
```

-continued

<213> ORGANISM: Aspergillus nidulans

<400> SEQUENCE: 10

```
Met Ala Phe Phe Thr Val Ala Leu Ser Leu Tyr Tyr Leu Leu Ser Arg
 1               5                  10                  15

Val Ser Ala Gln Ala Pro Val Gln Asn His Ser Cys Asn Thr Ala
            20                  25                  30

Asp Gly Gly Tyr Gln Cys Phe Pro Asn Val Ser His Val Trp Gly Gln
        35                  40                  45

Tyr Ser Pro Tyr Phe Ser Ile Glu Gln Glu Ser Ala Ile Ser Glu Asp
 50                  55                  60

Val Pro His Gly Cys Glu Val Thr Phe Val Gln Val Leu Ser Arg His
 65                  70                  75                  80

Gly Ala Arg Tyr Pro Thr Glu Ser Lys Ser Lys Ala Tyr Ser Gly Leu
                85                  90                  95

Ile Glu Ala Ile Gln Lys Asn Ala Thr Ser Phe Trp Gly Gln Tyr Ala
            100                 105                 110

Phe Leu Glu Ser Tyr Asn Tyr Thr Leu Gly Ala Asp Asp Leu Thr Ile
        115                 120                 125

Phe Gly Glu Asn Gln Met Val Asp Ser Gly Ala Lys Phe Tyr Arg Arg
    130                 135                 140

Tyr Lys Asn Leu Ala Arg Lys Asn Thr Pro Phe Ile Arg Ala Ser Gly
145                 150                 155                 160

Ser Asp Arg Val Val Ala Ser Ala Glu Lys Phe Ile Asn Gly Phe Arg
                165                 170                 175

Lys Ala Gln Leu His Asp His Gly Ser Lys Arg Ala Thr Pro Val Val
            180                 185                 190

Asn Val Ile Ile Pro Glu Ile Asp Gly Phe Asn Asn Thr Leu Asp His
        195                 200                 205

Ser Thr Cys Val Ser Phe Glu Asn Asp Glu Arg Ala Asp Glu Ile Glu
    210                 215                 220

Ala Asn Phe Thr Ala Ile Met Gly Pro Pro Ile Arg Lys Arg Leu Glu
225                 230                 235                 240

Asn Asp Leu Pro Gly Ile Lys Leu Thr Asn Glu Asn Val Ile Tyr Leu
                245                 250                 255

Met Asp Met Cys Ser Phe Asp Thr Met Ala Arg Thr Ala His Gly Thr
            260                 265                 270

Glu Leu Ser Pro Phe Cys Ala Ile Phe Thr Glu Lys Glu Trp Leu Gln
        275                 280                 285

Tyr Asp Tyr Leu Gln Ser Leu Ser Lys Tyr Tyr Gly Tyr Gly Ala Gly
    290                 295                 300

Ser Pro Leu Gly Pro Ala Gln Gly Ile Gly Phe Thr Asn Glu Leu Ile
305                 310                 315                 320

Ala Arg Leu Thr Gln Ser Pro Val Gln Asp Asn Thr Ser Thr Asn His
                325                 330                 335

Thr Leu Asp Ser Asn Pro Ala Thr Phe Pro Leu Asp Arg Lys Leu Tyr
            340                 345                 350

Ala Asp Phe Ser His Asp Asn Ser Met Ile Ser Ile Phe Phe Ala Met
        355                 360                 365

Gly Leu Tyr Asn Gly Thr Gln Pro Leu Ser Met Asp Ser Val Glu Ser
    370                 375                 380

Ile Gln Glu Met Asp Gly Tyr Ala Ala Ser Trp Thr Val Pro Phe Gly
385                 390                 395                 400
```

```
Ala Arg Ala Tyr Phe Glu Leu Met Gln Cys Glu Lys Glu Pro Leu
            405                 410                 415

Val Arg Val Leu Val Asn Asp Arg Val Val Pro Leu His Gly Cys Ala
        420                 425                 430

Val Asp Lys Phe Gly Arg Cys Thr Leu Asp Asp Trp Val Glu Gly Leu
            435                 440                 445

Asn Phe Ala Arg Ser Gly Gly Asn Trp Lys Thr Cys Phe Thr Leu
        450                 455                 460

<210> SEQ ID NO 11
<211> LENGTH: 467
<212> TYPE: PRT
<213> ORGANISM: Aspergillus ficuum

<400> SEQUENCE: 11

Met Gly Val Ser Ala Val Leu Leu Pro Leu Tyr Leu Leu Ser Gly Val
  1               5                  10                  15

Thr Ser Gly Leu Ala Val Pro Ala Ser Arg Asn Gln Ser Ser Cys Asp
             20                  25                  30

Thr Val Asp Gln Gly Tyr Gln Cys Phe Ser Glu Thr Ser His Leu Trp
         35                  40                  45

Gly Gln Tyr Ala Pro Phe Phe Ser Leu Ala Asn Glu Ser Val Ile Ser
     50                  55                  60

Pro Glu Val Pro Ala Gly Cys Arg Val Thr Phe Ala Gln Val Leu Ser
 65                  70                  75                  80

Arg His Gly Ala Arg Tyr Pro Thr Asp Ser Lys Gly Lys Lys Tyr Ser
                 85                  90                  95

Ala Leu Ile Glu Glu Ile Gln Gln Asn Ala Thr Thr Phe Asp Gly Lys
            100                 105                 110

Tyr Ala Phe Leu Lys Thr Tyr Asn Tyr Ser Leu Gly Ala Asp Asp Leu
        115                 120                 125

Thr Pro Phe Gly Glu Gln Glu Leu Val Asn Ser Gly Ile Lys Phe Tyr
    130                 135                 140

Gln Arg Tyr Glu Ser Leu Thr Arg Asn Ile Val Pro Phe Ile Arg Ser
145                 150                 155                 160

Ser Gly Ser Ser Arg Val Ile Ala Ser Gly Lys Lys Phe Ile Glu Gly
                165                 170                 175

Phe Gln Ser Thr Lys Leu Lys Asp Pro Arg Ala Gln Pro Gly Gln Ser
            180                 185                 190

Ser Pro Lys Ile Asp Val Val Ile Ser Glu Ala Ser Ser Ser Asn Asn
        195                 200                 205

Thr Leu Asp Pro Gly Thr Cys Thr Val Phe Glu Asp Ser Glu Leu Ala
    210                 215                 220

Asp Thr Val Glu Ala Asn Phe Thr Ala Thr Phe Val Pro Ser Ile Arg
225                 230                 235                 240

Gln Arg Leu Glu Asn Asp Leu Ser Gly Val Thr Leu Thr Asp Thr Glu
                245                 250                 255

Val Thr Tyr Leu Met Asp Met Cys Ser Phe Asp Thr Ile Ser Thr Ser
            260                 265                 270

Thr Val Asp Thr Lys Leu Ser Pro Phe Cys Asp Leu Phe Thr His Asp
        275                 280                 285

Glu Trp Ile Asn Tyr Asp Tyr Leu Gln Ser Leu Lys Lys Tyr Tyr Gly
    290                 295                 300

His Gly Ala Gly Asn Pro Leu Gly Pro Thr Gln Gly Val Gly Tyr Ala
305                 310                 315                 320
```

```
Asn Glu Leu Ile Ala Arg Leu Thr His Ser Pro Val His Asp Asp Thr
                325                 330                 335
Ser Ser Asn His Thr Leu Asp Ser Ser Pro Ala Thr Phe Pro Leu Lys
            340                 345                 350
Ser Thr Leu Tyr Ala Asp Phe Ser His Asp Asn Gly Ile Ile Ser Ile
            355                 360                 365
Leu Phe Ala Leu Gly Leu Tyr Asn Gly Thr Lys Pro Leu Ser Thr Thr
370                 375                 380
Thr Val Glu Asn Ile Thr Gln Thr Asp Gly Phe Ser Ser Ala Trp Thr
385                 390                 395                 400
Val Pro Phe Ala Ser Arg Leu Tyr Val Glu Met Met Gln Cys Gln Ala
                405                 410                 415
Glu Gln Ala Pro Leu Val Arg Val Leu Val Asn Asp Arg Val Val Pro
                420                 425                 430
Leu His Gly Cys Pro Val Asp Ala Leu Gly Arg Cys Thr Arg Asp Ser
            435                 440                 445
Phe Val Arg Gly Leu Ser Phe Ala Arg Ser Gly Gly Asp Trp Ala Glu
450                 455                 460
Cys Phe Ala
465

<210> SEQ ID NO 12
<211> LENGTH: 466
<212> TYPE: PRT
<213> ORGANISM: Aspergillus terreus

<400> SEQUENCE: 12

Met Gly Phe Leu Ala Ile Val Leu Ser Val Ala Leu Leu Phe Arg Ser
1               5                   10                  15
Thr Ser Gly Thr Pro Leu Gly Pro Arg Gly Lys His Ser Asp Cys Asn
            20                  25                  30
Ser Val Asp His Gly Tyr Gln Cys Phe Pro Glu Leu Ser His Lys Trp
        35                  40                  45
Gly Leu Tyr Ala Pro Tyr Phe Ser Leu Gln Asp Glu Ser Pro Phe Pro
50                  55                  60
Leu Asp Val Pro Glu Asp Cys His Ile Thr Phe Val Gln Val Leu Ala
65                  70                  75                  80
Arg His Gly Ala Arg Ser Pro Thr His Ser Lys Thr Lys Ala Tyr Ala
                85                  90                  95
Ala Thr Ile Ala Ala Ile Gln Lys Ser Ala Thr Ala Phe Pro Gly Lys
            100                 105                 110
Tyr Ala Phe Leu Gln Ser Tyr Asn Tyr Ser Leu Asp Ser Glu Glu Leu
            115                 120                 125
Thr Pro Phe Gly Arg Asn Gln Leu Arg Asp Leu Gly Ala Gln Phe Tyr
        130                 135                 140
Glu Arg Tyr Asn Ala Leu Thr Arg His Ile Asn Pro Phe Val Arg Ala
145                 150                 155                 160
Thr Asp Ala Ser Arg Val His Glu Ser Ala Glu Lys Phe Val Glu Gly
                165                 170                 175
Phe Gln Thr Ala Arg Gln Asp Asp His His Ala Asn Pro His Gln Pro
            180                 185                 190
Ser Pro Arg Val Asp Val Ala Ile Pro Glu Gly Ser Ala Tyr Asn Asn
            195                 200                 205
Thr Leu Glu His Ser Leu Cys Thr Ala Phe Glu Ser Ser Thr Val Gly
```

```
            210                 215                 220
Asp Asp Ala Val Ala Asn Phe Thr Ala Val Phe Ala Pro Ala Ile Ala
225                 230                 235                 240

Gln Arg Leu Glu Ala Asp Leu Pro Gly Val Gln Leu Ser Thr Asp Asp
                245                 250                 255

Val Val Asn Leu Met Ala Met Cys Pro Phe Glu Thr Val Ser Leu Thr
            260                 265                 270

Asp Asp Ala His Thr Leu Ser Pro Phe Cys Asp Leu Phe Thr Ala Thr
                275                 280                 285

Glu Trp Thr Gln Tyr Asn Tyr Leu Leu Ser Leu Asp Lys Tyr Tyr Gly
            290                 295                 300

Tyr Gly Gly Asn Pro Leu Gly Pro Val Gln Gly Val Gly Trp Ala
305                 310                 315                 320

Asn Glu Leu Met Ala Arg Leu Thr Arg Ala Pro Val His Asp His Thr
                325                 330                 335

Cys Val Asn Asn Thr Leu Asp Ala Ser Pro Ala Thr Phe Pro Leu Asn
            340                 345                 350

Ala Thr Leu Tyr Ala Asp Phe Ser His Asp Ser Asn Leu Val Ser Ile
                355                 360                 365

Phe Trp Ala Leu Gly Leu Tyr Asn Gly Thr Ala Pro Leu Ser Gln Thr
            370                 375                 380

Ser Val Glu Ser Val Ser Gln Thr Asp Gly Tyr Ala Ala Ala Trp Thr
385                 390                 395                 400

Val Pro Phe Ala Ala Arg Ala Tyr Val Glu Met Met Gln Cys Arg Ala
                405                 410                 415

Glu Lys Glu Pro Leu Val Arg Val Leu Val Asn Asp Arg Val Met Pro
            420                 425                 430

Leu His Gly Cys Pro Thr Asp Lys Leu Gly Arg Cys Lys Arg Asp Ala
                435                 440                 445

Phe Val Ala Gly Leu Ser Phe Ala Gln Ala Gly Gly Asn Trp Ala Asp
            450                 455                 460

Cys Phe
465

<210> SEQ ID NO 13
<211> LENGTH: 466
<212> TYPE: PRT
<213> ORGANISM: Talaromyces thermophilus

<400> SEQUENCE: 13

Met Ser Leu Leu Leu Val Leu Ser Gly Gly Leu Val Ala Leu Tyr
1               5                   10                  15

Val Ser Arg Asn Pro His Val Asp Ser His Ser Cys Asn Thr Val Glu
                20                  25                  30

Gly Gly Tyr Gln Cys Arg Pro Glu Ile Ser His Ser Trp Gly Gln Tyr
            35                  40                  45

Ser Pro Phe Phe Ser Leu Ala Asp Gln Ser Glu Ile Ser Pro Asp Val
    50                  55                  60

Pro Gln Asn Cys Lys Ile Thr Phe Val Gln Leu Leu Ser Arg His Gly
65                  70                  75                  80

Ala Arg Tyr Pro Thr Ser Ser Lys Thr Glu Leu Tyr Ser Gln Leu Ile
                85                  90                  95

Ser Arg Ile Gln Lys Thr Ala Thr Ala Tyr Lys Gly Tyr Tyr Ala Phe
            100                 105                 110
```

```
Leu Lys Asp Tyr Arg Tyr Gln Leu Gly Ala Asn Asp Leu Thr Pro Phe
        115                 120                 125

Gly Glu Asn Gln Met Ile Gln Leu Gly Ile Lys Phe Tyr Asn His Tyr
    130                 135                 140

Lys Ser Leu Ala Arg Asn Ala Val Pro Phe Val Arg Cys Ser Gly Ser
145                 150                 155                 160

Asp Arg Val Ile Ala Ser Gly Arg Leu Phe Ile Glu Gly Phe Gln Ser
                165                 170                 175

Ala Lys Val Leu Asp Pro His Ser Asp Lys His Asp Ala Pro Pro Thr
            180                 185                 190

Ile Asn Val Ile Ile Glu Gly Pro Ser Tyr Asn Asn Thr Leu Asp
        195                 200                 205

Thr Gly Ser Cys Pro Val Phe Glu Asp Ser Ser Gly His Asp Ala
    210                 215                 220

Gln Glu Lys Phe Ala Lys Gln Phe Ala Pro Ala Ile Leu Glu Lys Ile
225                 230                 235                 240

Lys Asp His Leu Pro Gly Val Asp Leu Ala Val Ser Asp Val Pro Tyr
                245                 250                 255

Leu Met Asp Leu Cys Pro Phe Glu Thr Leu Ala Arg Asn His Thr Asp
            260                 265                 270

Thr Leu Ser Pro Phe Cys Ala Leu Ser Thr Gln Glu Glu Trp Gln Ala
        275                 280                 285

Tyr Asp Tyr Tyr Gln Ser Leu Gly Lys Tyr Tyr Gly Asn Gly Gly Gly
    290                 295                 300

Asn Pro Leu Gly Pro Ala Gln Gly Val Gly Phe Val Asn Glu Leu Ile
305                 310                 315                 320

Ala Arg Met Thr His Ser Pro Val Gln Asp Tyr Thr Thr Val Asn His
                325                 330                 335

Thr Leu Asp Ser Asn Pro Ala Thr Phe Pro Leu Asn Ala Thr Leu Tyr
            340                 345                 350

Ala Asp Phe Ser His Asp Asn Thr Met Thr Ser Ile Phe Ala Ala Leu
        355                 360                 365

Gly Leu Tyr Asn Gly Thr Ala Lys Leu Ser Thr Thr Glu Ile Lys Ser
    370                 375                 380

Ile Glu Glu Thr Asp Gly Tyr Ser Ala Ala Trp Thr Val Pro Phe Gly
385                 390                 395                 400

Gly Arg Ala Tyr Ile Glu Met Met Gln Cys Asp Asp Ser Asp Glu Pro
                405                 410                 415

Val Val Arg Val Leu Val Asn Asp Arg Val Pro Leu His Gly Cys
            420                 425                 430

Glu Val Asp Ser Leu Gly Arg Cys Lys Arg Asp Asp Phe Val Arg Gly
        435                 440                 445

Leu Ser Phe Ala Arg Gln Gly Gly Asn Trp Glu Gly Cys Tyr Ala Ala
    450                 455                 460

Ser Glu
465

<210> SEQ ID NO 14
<211> LENGTH: 475
<212> TYPE: PRT
<213> ORGANISM: Thermomyces lanuginosa

<400> SEQUENCE: 14

Met Ala Gly Ile Gly Leu Gly Ser Phe Leu Val Leu Leu Leu Gln Phe
1               5                   10                  15
```

-continued

Ser Ala Leu Leu Thr Ala Ser Pro Ala Ile Pro Pro Phe Trp Arg Lys
            20                  25                  30

Lys His Pro Asn Val Asp Ile Ala Arg His Trp Gly Gln Tyr Ser Pro
        35                  40                  45

Phe Phe Ser Leu Ala Glu Val Ser Glu Ile Ser Pro Ala Val Pro Lys
    50                  55                  60

Gly Cys Arg Val Glu Phe Val Gln Val Leu Ser Arg His Gly Ala Arg
65                  70                  75                  80

Tyr Pro Thr Ala His Lys Ser Glu Val Tyr Ala Glu Leu Leu Gln Arg
                85                  90                  95

Ile Gln Asp Thr Ala Thr Glu Phe Lys Gly Asp Phe Ala Phe Leu Arg
            100                 105                 110

Asp Tyr Ala Tyr His Leu Gly Ala Asp Asn Leu Thr Arg Phe Gly Glu
        115                 120                 125

Glu Gln Met Met Glu Ser Gly Arg Gln Phe Tyr His Arg Tyr Arg Glu
    130                 135                 140

Gln Ala Arg Glu Ile Val Pro Phe Val Arg Ala Ala Gly Ser Ala Arg
145                 150                 155                 160

Val Ile Ala Ser Ala Glu Phe Phe Asn Arg Gly Phe Gln Asp Ala Lys
                165                 170                 175

Asp Arg Asp Pro Arg Ser Asn Lys Asp Gln Ala Glu Pro Val Ile Asn
            180                 185                 190

Val Ile Ile Ser Glu Glu Thr Gly Ser Asn Asn Thr Leu Asp Gly Leu
        195                 200                 205

Thr Cys Pro Ala Ala Glu Glu Ala Pro Asp Pro Thr Gln Pro Ala Glu
    210                 215                 220

Phe Leu Gln Val Phe Gly Pro Arg Val Leu Lys Lys Ile Thr Lys His
225                 230                 235                 240

Met Pro Gly Val Asn Leu Thr Leu Glu Asp Val Pro Leu Phe Met Asp
                245                 250                 255

Leu Cys Pro Phe Asp Thr Val Gly Ser Asp Pro Val Leu Phe Pro Arg
            260                 265                 270

Gln Leu Ser Pro Phe Cys His Leu Phe Thr Ala Asp Asp Trp Met Ala
        275                 280                 285

Tyr Asp Tyr Tyr Tyr Thr Leu Asp Lys Tyr Tyr Ser His Gly Gly Gly
    290                 295                 300

Ser Ala Phe Gly Pro Ser Arg Gly Val Gly Phe Val Asn Glu Leu Ile
305                 310                 315                 320

Ala Arg Met Thr Gly Asn Leu Pro Val Lys Asp His Thr Thr Val Asn
                325                 330                 335

His Thr Leu Asp Asp Asn Pro Glu Thr Phe Pro Leu Asp Ala Val Leu
            340                 345                 350

Tyr Ala Asp Phe Ser His Asp Asn Thr Met Thr Gly Ile Phe Ser Ala
        355                 360                 365

Met Gly Leu Tyr Asn Gly Thr Lys Pro Leu Ser Thr Ser Lys Ile Gln
    370                 375                 380

Pro Pro Thr Gly Ala Ala Ala Asp Gly Tyr Ala Ala Ser Trp Thr Val
385                 390                 395                 400

Pro Phe Ala Ala Arg Ala Tyr Val Glu Leu Leu Arg Cys Glu Thr Glu
                405                 410                 415

```
Thr Ser Ser Glu Glu Glu Glu Gly Glu Asp Glu Pro Phe Val Arg
            420                 425                 430

Val Leu Val Asn Asp Arg Val Pro Leu His Gly Cys Arg Val Asp
            435                 440                 445

Arg Trp Gly Arg Cys Arg Arg Asp Glu Trp Ile Lys Gly Leu Thr Phe
    450                 455                 460

Ala Arg Gln Gly Gly His Trp Asp Arg Cys Phe
465             470                 475

<210> SEQ ID NO 15
<211> LENGTH: 487
<212> TYPE: PRT
<213> ORGANISM: Myceliophthora thermophila

<400> SEQUENCE: 15

Met Thr Gly Leu Gly Val Met Val Val Met Val Gly Phe Leu Ala Ile
1               5                   10                  15

Ala Ser Leu Gln Ser Glu Ser Arg Pro Cys Asp Thr Pro Asp Leu Gly
                20                  25                  30

Phe Gln Cys Gly Thr Ala Ile Ser His Phe Trp Gly Gln Tyr Ser Pro
            35                  40                  45

Tyr Phe Ser Val Pro Ser Glu Leu Asp Ala Ser Ile Pro Asp Asp Cys
    50                  55                  60

Glu Val Thr Phe Ala Gln Val Leu Ser Arg His Gly Ala Arg Ala Pro
65                  70                  75                  80

Thr Leu Lys Arg Ala Ala Ser Tyr Val Asp Leu Ile Asp Arg Ile His
                85                  90                  95

His Gly Ala Ile Ser Tyr Gly Pro Gly Tyr Glu Phe Leu Arg Thr Tyr
                100                 105                 110

Asp Tyr Thr Leu Gly Ala Asp Glu Leu Thr Arg Thr Gly Gln Gln Gln
            115                 120                 125

Met Val Asn Ser Gly Ile Lys Phe Tyr Arg Arg Tyr Arg Ala Leu Ala
    130                 135                 140

Arg Lys Ser Ile Pro Phe Val Arg Thr Ala Gly Gln Asp Arg Val Val
145                 150                 155                 160

His Ser Ala Glu Asn Phe Thr Gln Gly Phe His Ser Ala Leu Leu Ala
                165                 170                 175

Asp Arg Gly Ser Thr Val Arg Pro Thr Leu Pro Tyr Asp Met Val Val
            180                 185                 190

Ile Pro Glu Thr Ala Gly Ala Asn Asn Thr Leu His Asn Asp Leu Cys
    195                 200                 205

Thr Ala Phe Glu Glu Gly Pro Tyr Ser Thr Ile Gly Asp Asp Ala Gln
    210                 215                 220

Asp Thr Tyr Leu Ser Thr Phe Ala Gly Pro Ile Thr Ala Arg Val Asn
225                 230                 235                 240

Ala Asn Leu Pro Gly Ala Asn Leu Thr Asp Ala Asp Thr Val Ala Leu
                245                 250                 255

Met Asp Leu Cys Pro Phe Glu Thr Val Ala Ser Ser Ser Asp Pro
            260                 265                 270

Ala Thr Ala Asp Ala Gly Gly Asn Gly Arg Pro Leu Ser Pro Phe
            275                 280                 285
```

```
Cys Arg Leu Phe Ser Glu Ser Glu Trp Arg Ala Tyr Asp Tyr Leu Gln
    290             295             300

Ser Val Gly Lys Trp Tyr Gly Tyr Gly Pro Gly Asn Pro Leu Gly Pro
305             310             315                     320

Thr Gln Gly Val Gly Phe Val Asn Glu Leu Leu Ala Arg Leu Ala Gly
                325             330                 335

Val Pro Val Arg Asp Gly Thr Ser Thr Asn Arg Thr Leu Asp Gly Asp
            340             345                 350

Pro Arg Thr Phe Pro Leu Gly Arg Pro Leu Tyr Ala Asp Phe Ser His
        355             360             365

Asp Asn Asp Met Met Gly Val Leu Gly Ala Leu Gly Ala Tyr Asp Gly
    370             375             380

Val Pro Pro Leu Asp Lys Thr Ala Arg Arg Asp Pro Glu Glu Leu Gly
385             390             395                     400

Gly Tyr Ala Ala Ser Trp Ala Val Pro Phe Ala Ala Arg Ile Tyr Val
            405             410             415

Glu Lys Met Arg Cys Ser Gly Gly Gly Gly Gly Gly Gly Gly Gly Glu
            420             425             430

Gly Arg Gln Glu Lys Asp Glu Glu Met Val Arg Val Leu Val Asn Asp
        435             440             445

Arg Val Met Thr Leu Lys Gly Cys Gly Ala Asp Glu Arg Gly Met Cys
    450             455             460

Thr Leu Glu Arg Phe Ile Glu Ser Met Ala Phe Ala Arg Gly Asn Gly
465             470             475             480

Lys Trp Asp Leu Cys Phe Ala
            485
```

US 7,326,554 B2

PHYTASE VARIANTS

CROSS-REFERENCE TO RELATED APPLICATIONS

This application is a divisional of U.S. application Ser. No. 10/083,452 filed Feb. 26, 2002, now U.S. Pat. No. 6,689,358, which is a continuation of U.S. application Ser. No. 09/273,871 filed Mar. 22, 1999, now U.S. Pat. 6,514, 495, which claims priority or the benefit of Danish application nos. PA 1998 00407, PA 1998 00806, PA 1998 01176, PA 1999 00091 filed Mar. 23, 1998, Jun. 19, 1998, Sep. 18, 1998 and Jan. 22, 1999, respectively, and U.S. Provisional Application Nos. 60/080,129, 60/090,675, 60/101,642 and 60/117,677 filed Mar. 31, 1998, Jun. 25, 1998, Sep. 24, 1998 and Jan. 28, 1999, respectively, the contents of which are fully incorporated herein by reference.

BACKGROUND OF THE INVENTION

1. Field of the Invention

This invention relates to variants of phytases, in particular variants of ascomycete phytases and variants of basidiomycete phytases, the corresponding cloned DNA sequences, a method of producing such phytase variants, and the use thereof for a number of industrial applications.

2. Description of Related Art

Phytic acid or myo-inositol 1,2,3,4,5,6-hexakis dihydrogen phosphate (or for short myo-inositol hexakisphosphate) is the primary source of inositol and the primary storage form of phosphate in plant seeds. Phytin is a mixed potassium, magnesium and calcium salt of inositol.

The phosphate moieties of phytic acid chelates divalent and trivalent cations such as metal ions, i.a. the nutritionally essential ions of calcium, iron, zinc and magnesium as well as the trace minerals manganese, copper and molybdenum.

Phytic acid and its salts, phytates, are often not metabolized, i.e. neither the phosphorous thereof, nor the chelated metal ions are nutritionally available.

Accordingly, food and feed preparations need to be supplemented with inorganic phosphate and often also the nutritionally essential ions such as iron and calcium, must be supplemented.

Still further, the phytate phosphorus passes through the gastrointestinal tract of such animals and is excreted with the manure, resulting in an undesirable phosphate pollution of the environment resulting e.g. in eutrophication of the water environment and extensive growth of algae.

Phytic acid or phytates, said terms being, unless otherwise indicated, in the present context used synonymously or at random, are degradable by phytases.

The production of phytases by plants as well as by microorganisms has been reported. Amongst the microorganisms, phytase producing bacteria as well as phytase producing fungi are known.

There are several descriptions of phytase producing filamentous fungi belonging to the fungal phylum of Ascomycota (ascomycetes). In particular, there are several references to phytase producing ascomycetes of the *Aspergillus* genus such as *Aspergillus terreus* (Yamada et al., 1986, Agric. Biol. Chem. 322:1275-1282). Also, the cloning and expression of the phytase gene from *Aspergillus niger* var. *awamori* has been described (Piddington et al., 1993, Gene 133:55-62). EP 0420358 describes the cloning and expression of a phytase of *Aspergillus ficuum* (*niger*). EP 0684313 describes the cloning and expression of phytases of the ascomycetes *Aspergillus niger, Myceliophthora thermophila, Aspergillus terreus*. Still further, some partial sequences of phytases of *Aspergillus nidulans, Talaromyces thermophilus, Aspergillus fumigatus* and another strain of *Aspergillus terreus* are given.

The cloning and expression of a phytase of *Thermomyces lanuginosus* is described in WO 97/35017.

There is a current need for phytases of amended properties or characteristics, e.g. phytases of increased thermostability, altered pH optimum (a high pH optimum being desirable for in-vitro processing, a low for in-vivo processing in the gastro-intestinal tract), and/or of a higher specific activity.

SUMMARY OF THE INVENTION

In a first aspect, the invention provides phytase variants, the characteristics of which are amended—as compared to a so-called model phytase.

Any model phytase, which is of a certain similarity to thirteen herein specifically disclosed model phytases, can be made the model of such variants.

In another aspect, the invention relates to a novel phytase derived from *Cladorrhinum foecundissimum*.

In still another aspect, the invention provides DNA sequences encoding these phytase variants and this phytase, and methods of their production.

Finally, the invention also relates generally to the use of the phytase and the phytase variants for liberating phosphorous from any phytase substrate, in particular inorganic phosphate from phytate or phytic acid.

BRIEF DESCRIPTION OF THE DRAWINGS

In the detailed description of the invention below, reference is made to the drawings, of which FIGS. 1A, 1B, 1C, and 1D show an alignment of thirteen specific phytase sequences (a multiple sequence alignment according to the program PileUp; GapWeight: 3.000; GapLengthWeight: 0.100) (SEQ ID NOS: 3-15);

FIG. 2 shows the amino acid and DNA sequence of a phytase ("C_foecundissimum") derived from strain CBS 427.97 of *Cladorrhinum foecundissimum* (SEQ ID NOS: 1 and 2) which was deposited on 23 Jan. 1997; the expression plasmid pYES 2.0 comprising the full length cDNA sequence was transformed into *E. coli* strain DSM 12742 which was deposited on 17 March 1999;

FIG. 3 shows an alignment of the phytase C_foecundissimum (SEQ ID NO: 2) with the model phytase M_thermophila (SEQ ID NO: 15), using the program GAP gcg (Gap Weight 3.000; Length Weight 0.100); and FIGS. 4A, 4B, 4C and 4D show how the C_foecundissimum phytase can be pasted onto the alignment of FIG. 1 (SEQ ID NOS: 2-15).

DETAILED DISCLOSURE OF THE INVENTION

Phytase

In the present context a phytase is an enzyme which catalyzes the hydrolysis of phytate (myo-inositol hexakisphosphate) to (1) myo-inositol and/or (2) mono-, di-, tri-, tetra- and/or penta-phosphates thereof and (3) inorganic phosphate. In the following, for short, the above compounds are sometimes referred to as IP6, I, IP1, IP2, IP3, IP4, IP5 and P, respectively. This means that by action of a phytase, IP6 is degraded into P+one or more of the components IP5, IP4, IP3, IP2, IP1 and I. Alternatively, myo-inositol carrying in total n phosphate groups attached to positions p, q, r, . . . is denoted Ins (p,q,r, . . . )Pn. For convenience Ins(1,2,3,4,5,6)P6 (phytic acid) is abbreviated PA.

According to the Enzyme nomenclature database ExPASy (a repository of information relative to the nomenclature of enzymes primarily based on the recommendations of the Nomenclature Committee of the International Union of Biochemistry and Molecular Biology (IUBMB) describing each type of characterized enzyme for which an EC (Enzyme Commission) number has been provided), two different types of phytases are known: A so-called 3-phytase (myo-inositol hexaphosphate 3-phosphohydrolase, EC 3.1.3.8) and a so-called 6-phytase (myo-inositol hexaphosphate 6-phosphohydrolase, EC 3.1.3.26). The 3-phytase hydrolyses first the ester bond at the D-3-position, whereas the 6-phytase hydrolyzes first the ester bond at the D-6- or L-6-position.

The expression "phytase" or "polypeptide or enzyme exhibiting phytase activity" is intended to cover any enzyme capable of effecting the liberation of inorganic phosphate or phosphorous from various myo-inositol phosphates. Examples of such myo-inositol phosphates (phytase substrates) are phytic acid and any salt thereof, e.g. sodium phytate or potassium phytate or mixed salts. Also any stereoisomer of the mono-, di-, tri-, tetra- or penta-phosphates of myo-inositol might serve as a phytase substrate. A preferred phytase substrate is phytic acid and salts thereof.

In accordance with the above definition, the phytase activity can be determined using any assay in which one of these substrates is used. In the present context (unless otherwise specified) the phytase activity is determined in the unit of FYT, one FYT being the amount of enzyme that liberates 1 µmol inorganic ortho-phosphate per min. under the following conditions: pH 5.5; temperature 37° C.; substrate: sodium phytate ($C_6H_6O_{24}P_6Na_{12}$) in a concentration of 0.0050 mol/l. A suitable phytase assay is described in the experimental part.

The present invention provides a genetically engineered phytase as described in the appending claims.

A genetically engineered phytase is a non-naturally occurring phytase which is different from a model phytase, e.g. a wild-type phytase. Genetically engineered phytases include, but are not limited to, phytases prepared by site-directed mutagenesis, gene shuffling, random mutagenesis etc.

The invention also provides DNA constructs, vectors, host cells, and methods of producing these genetically engineered phytases and phytase variants, as well as uses thereof.

A phytase variant is a polypeptide or enzyme or a fragment thereof which exhibits phytase activity and which is amended as compared to a model phytase.

Amended means altered by way of one or more amino acid or peptide substitutions, deletions, insertions and/or additions—in each case by, or of, one or more amino acids. Such substitutions, deletions, insertions, additions can be achieved by any method known in the art, e.g. gene shuffling, random mutagenesis, site-directed mutagenesis etc.

The model or parent phytase, from which the phytase variant is derived, can be any phytase, e.g. a wild-type phytase or a derivative, mutant or variant thereof, including allelic and species variants, as well as genetically engineered variants thereof, which e.g. can be prepared by site-directed mutagenesis, random mutagenesis, shuffling etc.

Included in the concept of model phytase is also any hybrid or chimeric phytase, i.e. a phytase which comprises a combination of partial amino acid sequences derived from at least two phytases.

The hybrid phytase may comprise a combination of partial amino acid sequences deriving from at least two ascomycete phytases, at least two basidiomycete phytases or from at least one ascomycete and at least one basidiomycete phytase. These ascomycete and basidiomycete phytases from which a partial amino acid sequence derives may, e.g., be any of those specific phytases referred to herein.

In the present context, a hybrid, shuffled, random mutagenized, site-directed mutagenized or otherwise genetically engineered phytase derived from ascomycete phytases only is also an ascomycete phytase; and a hybrid, shuffled, random mutagenized, site-directed mutagenized or otherwise genetically engineered phytase derived from model basidiomycete phytases only is also a basidiomycete phytase. Any hybrid derived from at least one ascomycete phytase as well as at least one basidiomycete phytase is called a mixed ascomycete/basidiomycete phytase and such phytase is also a model phytase in the present context.

Analogously, a hybrid, shuffled, random mutagenized, site-directed mutagenized or otherwise genetically engineered phytase derived from one or more *Aspergillus* phytases is also an *Aspergillus* derived phytase; and a hybrid, shuffled, random mutagenized, site-directed mutagenized or otherwise genetically engineered phytase derived from any other taxonomic sub-grouping mentioned herein is also to be designated a phytase derived from this taxonomic sub-grouping.

Still further, in the present context, "derived from" is intended to indicate a phytase produced or producible by a strain of the organism in question, but also a phytase encoded by a DNA sequence isolated from such strain and produced in a host organism transformed with said DNA sequence. Finally, the term is intended to indicate a phytase which is encoded by a DNA sequence of synthetic and/or cDNA origin and which has the identifying characteristics of the phytase in question.

Preferably the model phytase is a phytase which can be aligned as described below to either of the thirteen phytases of FIG. 1 (which are particularly preferred model phytases).

Preferred wild-type model phytases (i.e. neither recombinant, or shuffled or otherwise genetically engineered phytases) have a degree of similarity or homology, preferably identity, to amino acid residues 38-403 (Peniophora numbers) of either of these thirteen phytases or at least 40%, more preferably at least 50%, still more preferably at least 60%, in particular at least 70%, especially at least 80%, and in a most preferred embodiment a degree of similarity of at least 90%.

Preferred recombinant or shuffled or otherwise genetically engineered model phytases have a degree of similarity or homology, preferably identity, to amino acid residues 38-49, 63-77, 274-291, 281-300 and 389-403 (Peniophora numbers) of either of these thirteen phytases or at least 60%, more preferably at least 70%, still more preferably at least 80%, in particular at least 90%.

In a preferred embodiment the degree of similarity is based on a comparison with the complete amino acid sequence of either of the thirteen phytases.

The degree of similarity or homology, alternatively identity, can be determined using any alignment programme known in the art. A preferred alignment programme is GAP provided in the GCG version 8 program package (Program Manual for the Wisconsin Package, Version 8, August 1994, Genetics Computer Group, 575 Science Drive, Madison, Wis., USA 53711) (see also Needleman, S. B. and Wunsch, C. D., (1970), Journal of Molecular Biology, 48, 443-453).

Using GAP with the following settings for polypeptide sequence comparison: GAP weight of 3.000 and GAP length weight of 0.100.

Also preferred is a wild-type model phytase which comprises an amino acid sequence encoded by a DNA sequence which hybridizes to a DNA sequence encoding amino acid sequence 38-403 (Peniophora numbers) of any of the DNA sequences encoding the thirteen specific phytase sequences of FIG. 1.

A further preferred model phytase is a genetically engineered phytase, which comprises an amino acid sequence encoded by a DNA sequence which hybridizes to a DNA sequence encoding amino acid sequence 38-49, and to a DNA sequence encoding amino acid sequence 63-77, and to a DNA sequence encoding amino acid sequence 274-291, and to a DNA sequence encoding amino acid sequence 281-300, and to a DNA sequence encoding amino acid sequence 389-403 (Peniophora numbers) of any of the DNA sequences encoding the thirteen specific phytase sequences of FIG. 1.

In a preferred embodiment the hybridization is to the complete phytase encoding part of any of the thirteen phytases.

Suitable experimental conditions for determining whether a given DNA or RNA sequence "hybridizes" to a specified nucleotide or oligonucleotide probe involves presoaking of the filter containing the DNA fragments or RNA to examine for hybridization in 5×SSC (Sodium chloride/Sodium citrate), (J. Sambrook, E. F. Fritsch, and T. Maniatis, 1989, Molecular Cloning, A Laboratory Manual, 2d edition, Cold Spring Harbor, N.Y.) for 10 min, and prehybridization of the filter in a solution of 5×SSC, 5× Denhardt's solution (Sambrook et al. 1989), 0.5% SDS and 100 micrograms/ml of denatured sonicated salmon sperm DNA (Sambrook et al. 1989), followed by hybridization in the same solution containing a concentration of 10 ng/ml of a random-primed (Feinberg, A. P. and Vogelstein, B. (1983) Anal. Biochem. 132:6-13), $^{32}$P-dCTP-labeled (specific activity >1×109 cpm/microgram) probe for 12 hours at approximately 45° C.

The filter is then washed twice for 30 minutes in 2×SSC, 0.5% SDS at at least 55° C. (low stringency), at at least 60° C. (medium stringency), at at least 65° C. (medium/high stringency), at at least 70° C. (high stringency), or at at least 75° C. (very high stringency).

Molecules to which the oligonucleotide probe hybridizes under these conditions are detected using an x-ray film.

It should be noted that a certain specific phytase variant need not actually have been prepared from a specific model phytase, for this model phytase to qualify as a "model phytase" in the present context. It is sufficient that the variant exhibits at least one of the herein indicated amendments when it is afterwards compared with the model phytase.

The alignment of FIG. 1 is made using the program PileUp (Program Manual for the Wisconsin Package, Version 8, August 1994, Genetics Computer Group, 575 Science Drive, Madison, Wis., USA 53711), with a GapWeight of 3.000 and a GapLengthWeight of 0.100. When aligning a new model phytase or a new phytase variant all thirteen sequences can be included together with the new phytase (variant) in a multiple alignment, or, alternatively, at least one of the thirteen sequences of FIG. 1 is included together with the new phytase (variant) in an alignment.

A preferred procedure for aligning according to FIG. 1 a new model phytase (or a phytase variant) is as follows: The new model phytase is aligned with that specific sequence of the thirteen sequences of FIG. 1 to which the new model phytase has the highest degree of homology. For calculating the degree of homology, and for making the "alignment according to FIG. 1" of the two sequences, the program GAP referred to below is preferably used. Having aligned the two sequences, the new model phytase (or phytase variant) is added (pasted) to the alignment at FIG. 1 using the result of the first alignment (placing identical and homologous amino acid residues above each other as prescribed by the alignment), following which corresponding positions are now easily identifiable.

Example 7 shows an example of how to add a new model phytase to the alignment of FIG. 1 and deduce corresponding phytase variants thereof.

Other model phytases can be aligned and variants deduced in analogy with Example 7. This is so in particular for the following model phytases: The phytase of *Aspergillus niger* var. *awamori* (U.S. Pat. No. 5,830,733); the *Bacillus* phytase of WO 98/06858; the soy bean phytase of WO 98/20139; the maize phytase of WO 98/05785; the *Aspergillus* phytase of WO 97/38096; the phytases of *Monascus anka* of WO 98/13480; the phytase from *Schwanniomyces occidentalis* of EP 0699762 etc.

When comparing a model phytase and a proposed phytase variant using the alignment as described herein, corresponding amino acid positions can be identified, viz. a model position of the model phytase and a variant position of the variant—the corresponding model position and variant position are simply placed one above the other in the alignment. An amendment is said to have occurred in a given position if the model amino acid of the model position and the variant amino acid of the variant position are different. Preferred amendments of these positions manifest themselves as amino acid substitutions, deletions or additions.

Amended in at least one position means amended in one or more positions, i.e. in one, two, three, four, five, six, seven, eight, nine, ten, eleven, twelve etc. up to all N positions listed. This definition includes any possible subcombinations thereof, e.g. any set of two substitutions, any set of three, any set of four, etc.—to any set of (N−1) positions.

In the present context all sequences, whatever the model phytase, and including the thirteen sequences of FIG. 1, are numbered using the numbering corresponding to the phytase P_lycii. These "Peniophora numbers" are indicated at FIG. 1, together with the "alignment numbers." The numbering of P_lycii starts at M1 and ends at E439.

As explained above, the alignment reveals which positions in various phytase sequences other than P_lycii are equivalent or corresponding to the given P. lycii position.

A substitution of amino acids is indicated herein as for instance "3S," which indicates, that at position 3 amino acid S should be substituted for the "original" or model position 3 amino acid, whichever it is. Thus, the substitution should result in an S in the corresponding variant position. Considering now the alignment at FIG. 1, a substitution like e.g. "3S" is to be interpreted as follows, for the respective phytases shown (the amino acid first indicated is the "original" or model amino acid in "Peniophora position" 3):

| | |
|---|---|
| P_involtus_A1: | F3S (number 3 F substituted by S) |
| P_involtus_A2: | L3S |
| T_pubescens: | M1S |
| A_pediades: | M1S |
| P_lycii: | redundant (already an S) |
| A_fumigatus: | T5S |
| consphyA: | V5S |

-continued

| | |
|---|---|
| A_nidulans: | T5S |
| A_ficuum_NRRL3135: | A5S |
| A_terreus: | A5S |
| T_thermo: | L5S |
| T_lanuginosa: | V11S |
| M_thermophila: | G5S |

However, in what follows the above specific substitutions will be designated as follows (always using the Peniophora numbering):

| | |
|---|---|
| P_involtus_A1: | F3S |
| P_involtus_A2: | L3S |
| T_pubescens: | M3S |
| A_pediades: | M3S |
| P_lycii: | redundant (already an S) |
| A_fumigatus: | T3S |
| consphyA: | V3S |
| A_nidulans: | T3S |
| A_ficuum_NRRL3135: | A3S |
| A_terreus: | A3S |
| T_thermo: | L3S |
| T_lanuginosa: | V3S |
| M_thermophila: | G3S |

Still further, denotations like e.g. "3S,F,G" means that the amino acid in position 3 (Peniophora numbers) of the model phytase in question is substituted with either of S, F or G, i.e. e.g. the designation "3S,F,G" is considered fully equivalent to the designation "3S, 3F, 3G".

A denotation like ( )3S means that amino acid S is added to the sequence in question (at a gap in the actual sequence), in a position corresponding to Peniophora number 3—and vice versa for deletions (S3( )).

In case of regions in which the Peniophora phytase sequence has larger deletions than some of the other phytases in FIG. 1, for instance in the region between position 201 and 202 (Peniophora numbers), intermediate positions (amino acid residues in other sequences) are numbered by adding a,b,c,d, etc, in lower-case letters, to the last Peniophora position number, e.g. for the phytase M_thermophila: E201; G201a; P201b; Y201c; S201d; T201e; I201f; G202; D203 etc.

In one of the priority applications of the present application there are two minor position numbering errors: According to the above definitions, the positions referred to in the first priority application as 204 and 205 (Peniophora numbers) are wrongly designated; they should have been numbered 203a and 204, respectively. Therefore, 204 has been substituted by 203a and 205 by 204 throughout the present application.

A preferred phytase variant of the invention comprises an amino acid sequence which comprises, preferably contains, one or more of the following amino acid substitutions: 24C; 27P; 31Y; 33C; 39H,S,Q; 40L,N; 42S,G; 43A,C,D,E,F,G, H,I,K,L,M,N,P,Q,R,S,T,V,W,Y; 44N; 45D,S; 47Y,F; 49P; 51E,A,R; 56P; 58D,K,A; 59G; 61R; 62V,I; 69Q; 75W,F; 78D,S; 79G; 80K,A; 81A,G,Q,E; 82T; 83A,I,K,R,Q; 84I,Y, Q,V; 88I; 90R,A; 102Y; 115N; 116S; 118V,L; 119E; 120L; 122A; 123N,Q,T; 125M,S; 126H,S,V; 127Q,E,N; 128A,S,T; 132F,I,L; 143N; 148V,I; 151A,S; 152G; 153D,Y; 154D,Q, S,G; 157V; 158D,A; 159T; 160A,S; 161T,N; 162N; 163W; 170fH; 170gA; 171N; 172P; 173Q,S; 184Q,S,P; 185S; 186A,E,P; 187A; 187aS; 190A,P; 193S; 194S,T; 195T,V,L; 198A,N,V; 200G,V; 201D,E; a deletion of at least one of 201a, 201b, 201c, 201d, 201e, 201f, preferably all; 201eT; 202S,A; 203R,K,S; 203aV,T; 204Q,E,S,A,V; 205E; 211L,V; 215A,P; 220L,N; 223H,D; 228N; 232T; 233E; 235Y,L,T; 236Y,N; 237F; 238L,M; 242P,S; 244D; 246V; 251eE,Q; 253P; 256D; 260A,H; 264R,I; 265A,Q; 267D; 270Y,A,L,G; 271D,N; 273D,K; 275F,Y; 278T,H; 280A,P; 283P; 287A,T; 288L,I,F; 292F,Y; 293A,V; 302R,H; 304P,A; 332F; 336S; 337T,G,Q,S; 338I; 339V,I; 340P,A; 343A,S,F,I,L; 348Y; 349P; 352K; 360R; 362P; 364W,F; 365V,L,A,S; 366D,S,V; 367A,K; 368K; 369I,L; 370V; 373A,S; 374S,A; 375H; 376M; 383kQ,E; 387P; 393V; 396R; 404A,G; 409R; 411K, T; 412R; 417E,R; 421F,Y; 431E.

In a preferred embodiment this is with the proviso that the model phytase does not already comprise the above suggested amino acid substitution or addition or deletion at the position indicated. Or, with the proviso that, for each position, the model amino acid is not already the variant amino acid hereby proposed. But these provisos can be said to be in fact already inherent in the above wording, because of the expression "amended."

The various preferred phytase variants of claims 16-34 comprises, preferably contains or have, amino acid sequences which comprise or contain one or more of the amino acid substitutions, additions, or deletions listed in the respective claims.

In a preferred embodiment the various phytase variants comprise 1, 2, 3, 4, 5, 6, 7, 8, 9 or even 10 of these substitutions; or a number of substitutions of 10-15, 15-20, 20-30 or even 30-50; eventually up to 60, 70, 80 or 90 substitutions.

In another preferred embodiment, the amino acid sequence of the various phytase variants comprise one or more substitutions of the substitution sub-groupings listed hereinbelow; or combinations of substitutions classified in two or more sub-groupings.

Generally, instead of "comprise," "contain" or "have," the amino acid sequences of preferred variants "consist essentially of" or "consist of" the specific model phytases of FIG. 1, as modified by one or more of the substitutions described herein.

In the present context a basidiomycete means a microorganism of the phylum Basidiomycota. This phylum of Basidiomycota is comprised in the fungal kingdom together with e.g. the phylum Ascomycota ("ascomycetes").

Taxonomical questions can be clarified by consulting the references listed below or by consulting a fungal taxonomy database (NIH Data Base (Entrez)) which is available via the Internet on World Wide Web.

For a definition of basidiomycetes, reference is made to either Jülich, 1981, Higher Taxa of Basidiomycetes; Ainsworth & Bisby's (eds.) Dictionary of the Fungi, 1995, Hawksworth, D. L., P. M. Kirk, B. C. Sutton & D. N. Pegler; or Hansen & Knudsen (Eds.), Nordic Macromycetes, vol. 2 (1992) and 3 (1997). A preferred reference is Hansen & Knudsen.

For a definition of ascomycetes, reference is made to either of Ainsworth & Brisby cited above or Systema Ascomycetum by Eriksson, O. E. & D. L. Hawksworth, Vol. 16, 1998. A preferred reference is Eriksson et al.

Generally, a microorganism which is classified as a basidiomycete/ascomycete in either of the references listed above, including the database, is a basidiomycete/ascomycete in the present context.

Some Aspergillus strains are difficult to classify because they are anamorphous, and therefore they might be classified in Fungi Imperfecti. However, once the teleomorphous counterpart is found, it is re-classified taxonomically. For instance, the teleomorph of *A. nidulans* is *Emericella nidulans* (of the family Trichocomaceae, the order Eurotiales, the class Plectomycetes of the phylum Ascomycota). These subgroupings of Ascomycota are preferred, together with the family Lasiosphaeriaceae, the order Sordariales, the class Pyrenomycetes of the phylum Ascomycota.

The wording "ascomycetes" and analogues as used herein includes any strains of *Aspergillus, Thermomyces, Myceliophthora*, and *Talaromyces*, which are anamorphous and thus would be classified in Fungi Imperfecti.

Preferred basidiomycete phytases are those listed in WO 98/28409, in the very beginning of the section headed "Detailed description of the invention".

DNA sequences encoding the thirteen specifically listed model phytases and other model phytases can be prepared according to the teachings of each of the documents listed under the brief description of the drawings.

A DNA sequence encoding a model phytase may be isolated from any cell or microorganism producing the phytase in question, using various methods well known in the art. First, a genomic DNA and/or cDNA library should be constructed using chromosomal DNA or messenger RNA from the organism that produces the phytase. Then, if the amino acid sequence of the phytase is known, homologous, labelled oligonucleotide probes may be synthesized and used to identify phytase-encoding clones from a genomic library prepared from the organism in question. Alternatively, a labelled oligonucleotide probe containing sequences homologous to a known phytase gene could be used as a probe to identify phytase-encoding clones, using hybridization and washing conditions of lower stringency.

Yet another method for identifying phytase-encoding clones would involve inserting fragments of genomic DNA into an expression vector, such as a plasmid, transforming phytase-negative bacteria with the resulting genomic DNA library, and then plating the transformed bacteria onto agar containing a substrate for phytase thereby allowing clones expressing the phytase to be identified.

Alternatively, the DNA sequence encoding the enzyme may be prepared synthetically by established standard methods, e.g. the phosphoroamidite method described by S. L. Beaucage and M. H. Caruthers (1981) or the method described by Matthes et al. (1984). In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al. (1988).

DNA encoding the phytase variants of the present invention can be prepared by methods known in the art, such as site-directed mutagenesis. Once a DNA sequence encoding a model phytase of interest has been isolated, and desirable sites for mutation identified, mutations may be introduced using synthetic oligonucleotides. These oligonucleotides contain nucleotide sequences flanking the desired mutation sites; mutant nucleotides are inserted during oligonucleotide synthesis. In a specific method, a single-stranded gap of DNA, bridging the phytase-encoding sequence, is created in a vector carrying the phytase-encoding gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al. (1984). U.S. Pat. No. 4,760,025 discloses the introduction of oligonucleotides encoding multiple mutations by performing minor alterations of the cassette. However, an even greater variety of mutations can be introduced at any one time by the Morinaga method because a multitude of oligonucleotides, of various lengths, can be introduced.

Another method of introducing mutations into DNA sequences encoding a desired model phytase is described in Nelson and Long (1989). It involves a 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Yet another method of mutating DNA sequences encoding a model phytase is random mutagenesis. Random mutagenesis is suitably performed either as localized or region-specific random mutagenesis in at least three parts of the gene translating to the amino acid sequence shown in question, or within the whole gene.

The random mutagenesis of a DNA sequence encoding a model phytase may be conveniently performed by use of any method known in the art.

In relation to the above, further aspects of the present invention relates to a method for generating a variant of a model phytase, wherein the variant preferably exhibits amended characteristics as described below, the method comprising:

(a) subjecting a DNA sequence encoding the model phytase to Site-directed Mutagenesis, or the Nelson and Long PCR mutagenesis method or to random mutagenesis, (b) expressing the mutated DNA sequence obtained in step (a) in a host cell, and (c) screening for host cells expressing a phytase variant which has an altered property relative to the model phytase.

When using random mutagenesis, step (a) of the above method of the invention is preferably performed using doped primers.

For instance, the random mutagenesis may be performed by use of a suitable physical or chemical mutagenizing agent, by use of a suitable oligonucleotide, or by subjecting the DNA sequence to PCR generated mutagenesis. Furthermore, the random mutagenesis may be performed by use of any combination of these mutagenizing agents. The mutagenizing agent may, e.g., be one which induces transitions, transversions, inversions, scrambling, deletions, and/or insertions.

Examples of a physical or chemical mutagenizing agent suitable for the present purpose include ultraviolet (UV) irradiation, hydroxylamine, N-methyl-N'-nitro-N-nitrosoguanidine (MNNG), O-methyl hydroxylamine, nitrous acid, ethyl methane sulphonate (EMS), sodium bisulphite, formic acid, and nucleotide analogues. When such agents are used, the mutagenesis is typically performed by incubating the DNA sequence encoding the parent enzyme to be mutagenized in the presence of the mutagenizing agent of choice under suitable conditions for the mutagenesis to take place, and selecting for mutated DNA having the desired properties.

When the mutagenesis is performed by the use of an oligonucleotide, the oligonucleotide may be doped or spiked with the three non-parent nucleotides during the synthesis of the oligonucleotide at the positions which are to be changed. The doping or spiking may be done so that codons for unwanted amino acids are avoided. The doped or spiked oligonucleotide can be incorporated into the DNA encoding the phytase enzyme by any published technique, using e.g. PCR, LCR or any DNA polymerase and ligase as deemed appropriate.

Preferably, the doping is carried out using "constant random doping", in which the percentage of wild-type and mutation in each position is predefined. Furthermore, the doping may be directed toward a preference for the introduction of certain nucleotides, and thereby a preference for the introduction of one or more specific amino acid residues. The doping may be made, e.g., so as to allow for the introduction of 90% wild type and 10% mutations in each position. An additional consideration in the choice of a doping scheme is based on genetic as well as protein-structural constraints. The doping scheme may be made by using the DOPE program which, inter alia, ensures that introduction of stop codons is avoided.

When PCR-generated mutagenesis is used, either a chemically treated or non-treated gene encoding a model phytase is subjected to PCR under conditions that increase the mis-incorporation of nucleotides (Deshler 1992; Leung et al., Technique, Vol.1, 1989, pp. 11-15).

A mutator strain of *E. coli* (Fowler et al., Molec. Gen. Genet., 133, 1974, pp. 179-191), *S. cereviseae* or any other microbial organism may be used for the random mutagenesis of the DNA encoding the model phytase by, e.g., transforming a plasmid containing the parent glycosylase into the mutator strain, growing the mutator strain with the plasmid and isolating the mutated plasmid from the mutator strain. The mutated plasmid may be subsequently transformed into the expression organism.

The DNA sequence to be mutagenized may be conveniently present in a genomic or cDNA library prepared from an organism expressing the model phytase. Alternatively, the DNA sequence may be present on a suitable vector such as a plasmid or a bacteriophage, which as such may be incubated with or otherwise exposed to the mutagenizing agent. The DNA to be mutagenized may also be present in a host cell either by being integrated in the genome of said cell or by being present on a vector harboured in the cell. Finally, the DNA to be mutagenized may be in isolated form. It will be understood that the DNA sequence to be subjected to random mutagenesis is preferably a cDNA or a genomic DNA sequence.

In some cases it may be convenient to amplify the mutated DNA sequence prior to performing the expression step b) or the screening step c). Such amplification may be performed in accordance with methods known in the art, the presently preferred method being PCR-generated amplification using oligonucleotide primers prepared on the basis of the DNA or amino acid sequence of the parent enzyme.

Subsequent to the incubation with or exposure to the mutagenizing agent, the mutated DNA is expressed by culturing a suitable host cell carrying the DNA sequence under conditions allowing expression to take place. The host cell used for this purpose may be one which has been transformed with the mutated DNA sequence, optionally present on a vector, or one which was carried the DNA sequence encoding the parent enzyme during the mutagenesis treatment. Examples of suitable host cells are the following: gram positive bacteria such as *Bacillus subtilis*, *Bacillus licheniformis*, *Bacillus lentus*, *Bacillus brevis*, *Bacillus stearothermophilus*, *Bacillus alkalophilus*, *Bacillus amyloliquefaciens*, *Bacillus coagulans*, *Bacillus circulans*, *Bacillus lautus*, *Bacillus megaterium*, *Bacillus thuringiensis*, *Streptomyces lividans* or *Streptomyces murinus*; and gram-negative bacteria such as *E. coli*.

The mutated DNA sequence may further comprise a DNA sequence encoding functions permitting expression of the mutated DNA sequence.

The random mutagenesis may be advantageously localized to a part of the model phytase in question using Localized random mutagenesis. This may, e.g., be advantageous when certain regions of the enzyme have been identified to be of particular importance for a given property of the enzyme, and when modified are expected to result in a variant having improved properties. Such regions may normally be identified when the tertiary structure of the parent enzyme has been elucidated and related to the function of the enzyme.

The localized or region-specific random mutagenesis is conveniently performed by use of PCR generated mutagenesis techniques as described above or any other suitable technique known in the art. Alternatively, the DNA sequence encoding the part of the DNA sequence to be modified may be isolated, e.g., by insertion into a suitable vector, and said part may be subsequently subjected to mutagenesis by use of any of the mutagenesis methods discussed above.

For region-specific random mutagenesis with a view to amending e.g. the specific activity of a model phytase, codon positions corresponding to the following amino acid residues from the amino acid sequences set forth in FIG. 1 may appropriately be targeted:

Residues: 41-47, 68-80, 83-84, 115-118, 120-126, 128, 149-163, 184-185, 191-193, 198-201e, 202-203, 205, 235-236, 238-239, 242-243, 270-279, 285, 288, 332-343, 364-367, 369-375, 394.

Regions: 41-47, 68-80, 120-128, 149-163, 270-279, 332-343, 364-375.

The random mutagenesis may be carried out by the following steps:

1. Select regions of interest for modification in the parent enzyme
2. Decide on mutation sites and non-mutated sites in the selected region
3. Decide on which kind of mutations should be carried out, e.g. with respect to the desired stability and/or performance of the variant to be constructed
4. Select structurally reasonable mutations
5. Adjust the residues selected by step 3 with regard to step 4.
6. Analyse by use of a suitable dope algorithm the nucleotide distribution.
7. If necessary, adjust the wanted residues to genetic code realism, e.g. taking into account constraints resulting from the genetic code, e.g. in order to avoid introduction of stop codons; the skilled person will be aware that some codon combinations cannot be used in practice and will need to be adapted
8. Make primers
9. Perform random mutagenesis by use of the primers
10. Select resulting phytase variants by screening for the desired improved properties.

Suitable dope algorithms for use in step 6 are well known in the art. One such algorithm is described by Tomandl, D. et al., 1997, Journal of Computer-Aided Molecular Design 11:29-38. Another algorithm is DOPE (Jensen, L J, Andersen, K V, Svendsen, A, and Kretzschmar, T (1998) Nucleic Acids Research 26:697-702).

A DNA sequence encoding a model phytase or a phytase variant of the invention can be expressed using an expression vector, a recombinant expression vector, which typically includes control sequences encoding a promoter, operator, ribosome binding site, translation initiation signal, and, optionally, a repressor gene or various activator genes.

The recombinant expression vector may be any vector which may conveniently be subjected to recombinant DNA procedures, and the choice of vector will often depend on the host cell into which it is to be introduced. Thus, the vector may be an autonomously replicating vector, e.g. a plasmid, a bacteriophage or an extra-chromosomal element. Alternatively, the vector may be one which, when introduced into a host cell, is integrated into the host cell genome and replicated together with the chromosome(s) into which it has been integrated.

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell. An example of a suitable promoter for directing the transcription of the DNA sequence encoding a phytase variant of the invention, especially in a bacterial host, is the promoter of the lac operon of *E. coli*. For transcription in a fungal host, examples of useful promoters are those derived from the gene encoding *A. oryzae* TAKA amylase.

The expression vector of the invention may also comprise a suitable transcription terminator and, in eukaryotes, polyadenylation sequences operably connected to the DNA sequence encoding the phytase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin resistance. Furthermore, the vector may comprise *Aspergillus* selection markers such as amdS, argB, niaD and sC, or the selection may be accomplished by co-transformation, e.g. as described in WO 91/17243.

The procedures used to ligate the DNA construct of the invention encoding a phytase variant, the promoter, terminator and other elements, respectively, and to insert them into suitable vectors containing the information necessary for replication, are well known to persons skilled in the art (cf., for instance, Sambrook et al. (1989)).

The cell of the invention, either comprising a DNA construct or an expression vector of the invention as defined above, is advantageously used as a host cell in the recombinant production of a phytase variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

An isolated DNA molecule or, alternatively, a "cloned DNA sequence" "a DNA construct," "a DNA segment" or "an isolated DNA sequence" refers to a DNA molecule or sequence which can be cloned in accordance with standard cloning procedures used in genetic engineering to relocate the DNA segment from its natural location to a different site where it will be replicated. The term refers generally to a nucleic acid sequence which is essentially free of other nucleic acid sequences, e.g., at least about 20% pure, preferably at least about 40% pure, more preferably about 60% pure, even more preferably about 80% pure, most preferably about 90% pure, and even most preferably about 95% pure, as determined by agarose gel electrophoresis. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

The term "vector" is intended to include such terms/objects as "nucleic acid constructs," "DNA constructs," expression vectors" or "recombinant vectors."

The nucleic acid construct comprises a nucleic acid sequence of the present invention operably linked to one or more control sequences capable of directing the expression of the coding sequence in a suitable host cell under conditions compatible with the control sequences.

"Nucleic acid construct" is defined herein as a nucleic acid molecule, either single or double-stranded, which is isolated from a naturally occurring gene or which has been modified to contain segments of nucleic acid which are combined and juxtaposed in a manner which would not otherwise exist in nature.

The term nucleic acid construct may be synonymous with the term expression cassette when the nucleic acid construct contains all the control sequences required for expression of a coding sequence of the present invention.

The term "coding sequence" as defined herein primarily comprises a sequence which is transcribed into mRNA and translated into a polypeptide of the present invention when placed under the control of the above mentioned control sequences. The boundaries of the coding sequence are generally determined by a translation start codon ATG at the 5'-terminus and a translation stop codon at the 3'-terminus. A coding sequence can include, but is not limited to, DNA, cDNA, and recombinant nucleic acid sequences.

The term "control sequences" is defined herein to include all components which are necessary or advantageous for expression of the coding sequence of the nucleic acid sequence. Each control sequence may be native or foreign to the nucleic acid sequence encoding the polypeptide. Such control sequences include, but are not limited to, a leader, a polyadenylation sequence, a propeptide sequence, a promoter, a signal sequence, and a transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide.

A "host cell" or "recombinant host cell" encompasses any progeny of a parent cell which is not identical to the parent cell due to mutations that occur during replication.

The cell is preferably transformed with a vector comprising a nucleic acid sequence of the invention followed by integration of the vector into the host chromosome.

"Transformation" means introducing a vector comprising a nucleic acid sequence of the present invention into a host cell so that the vector is maintained as a chromosomal integrant or as a self-replicating extra-chromosomal vector. Integration is generally considered to be an advantage as the nucleic acid sequence is more likely to be stably maintained in the cell. Integration of the vector into the host chromosome may occur by homologous or non-homologous recombination as described above.

The host cell may be a unicellular microorganism, e.g., a prokaryote, or a non-unicellular microorganism, e.g., a eukaryote. Examples of eukaryote cells are a mammalian cell, an insect cell, a plant cell or a fungal cell. Useful mammalian cells include Chinese hamster ovary (CHO) cells, HeLa cells, baby hamster kidney (BHK) cells, COS cells, or any number of other immortalized cell lines available, e.g., from the American Type Culture Collection.

In a preferred embodiment, the host cell is a fungal cell.

Fungal cells may be transformed by a process involving protoplast formation, transformation of the protoplasts, and regeneration of the cell wall in a manner known per se.

The present invention also relates to a transgenic plant, plant part, such as a plant seed, or plant cell, which has been transformed with a DNA sequence encoding the phytase of the invention so as to express or produce this enzyme. Also compositions and uses of such plant or plant part are within the scope of the invention, especially its use as feed and food or additives therefore, along the lines of the present use and food/feed claims.

The transgenic plant can be dicotyledonous or monocotyledonous, for short a dicot or a monocot. Of primary interest are such plants which are potential food or feed components and which comprise phytic acid. A normal phytic acid level of feed components is 0.1-100 g/kg, or more usually 0.5-50 g/kg, most usually 0.5-20 g/kg. Examples of monocot plants are grasses, such as meadow grass (blue grass, Poa), forage grass such as festuca, lolium, temperate grass, such as Agrostis, and cereals, e.g. wheat, oats, rye, barley, rice, sorghum and maize (corn).

Examples of dicot plants are legumes, such as lupins, pea, bean and soybean, and cruciferous (family Brassicaceae), such as cauliflower, oil seed rape and the closely related model organism *Arabidopsis thaliana*.

Such transgenic plant etc. is capable of degrading its own phytic acid, and accordingly the need for adding such enzymes to food or feed comprising such plants is alleviated. Preferably, the plant or plant part, e.g. the seeds, are ground or milled, and possibly also soaked before being added to the food or feed or before the use, e.g. intake, thereof, with a view to adapting the speed of the enzymatic degradation to the actual use.

If desired, the plant produced enzyme can also be recovered from the plant. In certain cases the recovery from the plant is to be preferred with a view to securing a heat stable formulation in a potential subsequent pelleting process.

Examples of plant parts are stem, callus, leaves, root, fruits, seeds, tubers etc. But also any plant tissue is included in this definition.

Any plant cell, whatever the tissue origin, is included in the definition of plant cells above.

Also included within the scope of the invention are the progeny of such plants, plant parts and plant cells.

The skilled man will know how to construct a DNA expression construct for insertion into the plant in question, paying regard i.a. to whether the enzyme should be excreted in a tissue specific way. Of relevance for this evaluation is the stability (pH-stability, degradability by endogenous proteases etc.) of the phytase in the expression compartments of the plant. He will also be able to select appropriate regulatory sequences such as promoter and terminator sequences, and signal or transit sequences if required (Tague et al, Plant, Phys., 86, 506, 1988).

The plant, plant part etc. can be transformed with this DNA construct using any known method. An example of such method is the transformation by a viral or bacterial vector such as bacterial species of the genus *Agrobacterium* genetically engineered to comprise the gene encoding the phytase of the invention. Also methods of directly introducing the phytase DNA into the plant cell or plant tissue are known in the art, e.g. micro injection and electroporation (Gasser et al, Science, 244, 1293; Potrykus, Bio/Techn. 8, 535, 1990; Shimamoto et al, Nature, 338, 274, 1989).

Following the transformation, the transformants are screened using any method known to the skilled man, following which they are regenerated into whole plants.

These plants etc. as well as their progeny then carry the phytase encoding DNA as a part of their genetic equipment.

In general, reference is made to WO 91/14782 and WO 91/14772.

*Agrobacterium tumefaciens* mediated gene transfer is the method of choice for generating transgenic dicots (for review Hooykas & Schilperoort, 1992. Plant Mol. Biol. 19: 15-38), however it can also be used for transforming monocots. Due to host range limitations it is generally not possible to transform monocots with the help of *A. tumefaciens*. Here, other methods have to be employed. The method of choice for generating transgenic monocots is particle bombardment (microscopic gold or tungsten particles coated with the transforming DNA) of embryonic calli or developing embryos (Christou, 1992. Plant J. 2: 275-281; Shimamoto, 1994. Curr. Opin. Biotechnol. 5: 158-162; Vasil et al., 1992. Bio/Technology 10: 667-674).

Also other systems for the delivery of free DNA into these plants, including viral vectors (Joshi & Joshi, 1991. FEBS Lett. 281: 1-8), protoplast transformation via polyethylene glycol or electroporation (for review see Potyrkus, 1991. Annu. Rev. Plant Physiol. Plant Mol. Biol. 42: 205-225), microinjection of DNA into mesophyll protoplasts (Crossway et al., 1986. Mol. Gen. Genet. 202: 79-85), and macroinjection of DNA into young floral tillers of cereal plants (de la Pena et al., 1987. Nature 325: 274-276) are preferred methods.

In general, the cDNA or gene encoding the phytase variant of the invention is placed in an expression cassette (e.g. Pietrzak et al., 1986. Nucleic Acids Res. 14: 5857-5868) consisting of a suitable promoter active in the target plant and a suitable terminator (termination of transcription). This cassette (of course including a suitable selection marker, see below) will be transformed into the plant as such in case of monocots via particle bombardment. In case of dicots the expression cassette is placed first into a suitable vector providing the T-DNA borders and a suitable selection marker which in turn are transformed into *Agrobacterium tumefaciens*. Dicots will be transformed via the *Agrobacterium* harboring the expression cassette and selection marker flanked by T-DNA following standard protocols (e.g. Akama et al., 1992. Plant Cell Reports 12: 7-11). The transfer of T-DNA from Agrobacterium to the Plant cell has been recently reviewed (Zupan & Zambryski, 1995. Plant Physiol. 107: 1041-1047). Vectors for plant transformation via *Agrobacterium* are commercially available or can be obtained from many labs that construct such vectors (e.g. Deblaere et al., 1985. Nucleic Acids Res. 13: 4777-4788; for review see Klee et al., 1987. Annu. Rev. Plant Physiol. 38: 467-486).

Available plant promoters: Depending on the process under manipulation, organ- and/or cell-specific expression as well as appropriate developmental and environmental control may be required. For instance, it is desirable to express a phytase cDNA in maize endosperm etc. The most commonly used promoter has been the constitutive 35S-CaMV promoter Franck et al., 1980. Cell 21: 285-294). Expression will be more or less equal throughout the whole plant. This promoter has been used successfully to engineer herbicide- and pathogen-resistant plants (for review see Stitt & Sonnewald, 1995. Annu. Rev. Plant Physiol. Plant Mol. Biol. 46: 341-368). Organ-specific promoters have been reported for storage sink tissues such as seeds, potato tubers, and fruits (Edwards & Coruzzi, 1990. Annu. Rev. Genet. 24: 275-303), and for metabolic sink tissues such as meristems (Ito et al., 1994. Plant Mol. Biol. 24: 863-878).

The medium used to culture the transformed host cells may be any conventional medium suitable for growing the host cells in question. The expressed phytase may conveniently be secreted into the culture medium and may be recovered therefrom by well-known procedures including separating the cells from the medium by centrifugation or filtration, precipitating proteinaceous com-ponents of the medium by means of a salt such as ammonium sulphate, followed by chromatographic procedures such as ion exchange chromatography, affinity chromatography, or the like.

Preferred host cells are a strain of *Fusarium, Hansenula, Trichoderma* or *Aspergillus*, in particular a strain of *Fusarium graminearum, Fusarium venenatum, Fusarium cerealis, Fusarium* sp. having the identifying characteristic of Fusarium ATCC 20334, as further described in PCT/US/95/07743, *Hansenula* polymorpha, *Trichoderma harzianum* or *Trichoderma reesei, Aspergillus niger* or *Aspergillus oryzae*.

References for expression in *Hansenula polymorpha*: Gellissen, G., Piontek, M., Dahlems, U., Jenzelewski, V., Gavagan, J. E., DiCosimo, R., Anton, D. I. & Janowicz, Z. A. (1996) Recombinant *Hansenula polymorpha* as a biocatalyst: coexpression of the spinach glycolate oxidase (GO) and the *S. cerevisiae* catalase T (CTT1) gene. Appl. Microbiol. Biotechnol. 46, 46-54.

Some more specific uses of the phytase variants according to the invention appear from PCT/DK97/00568, the last pages of the detailed description of the invention section.

In a preferred embodiment, the phytase variant of the invention is essentially free of other non-phytase polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE. Sometimes such polypeptide is alternatively referred to as a "purified" and/or "isolated" phytase.

A phytase polypeptide which comprises a phytase variant of the invention includes fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) encoding a phytase variant of the present invention. Techniques for producing fusion polypeptides are known in the art, and include, ligating the coding sequences encoding the polypeptides so that they are in frame and that expression of the fused polypeptide is under control of the same promoter(s) and terminator.

A "feed" and a "food," respectively, means any natural or artificial diet, meal or the like or components of such meals intended or suitable for being eaten, taken in, digested, by an animal and a human being, respectively.

The phytase variant of the invention may exert its effect in vitro or in vivo, i.e. before intake or in the stomach of the individual, respectively. Also a combined action is possible.

A phytase composition according to the invention always comprises at least one phytase of the invention.

Generally, phytase compositions are liquid or dry.

Liquid compositions need not contain anything more than the phytase enzyme, preferably in a highly purified form. Usually, however, a stabilizer such as glycerol, sorbitol or mono propylen glycol is also added. The liquid composition may also comprise other additives, such as salts, sugars, preservatives, pH-adjusting agents, proteins, phytate (a phytase substrate). Typical liquid compositions are aqueous or oil-based slurries. The liquid compositions can be added to a food or feed after an optional pelleting thereof.

Dry compositions may be spray-dried compositions, in which case the composition need not contain anything more than the enzyme in a dry form. Usually, however, dry compositions are so-called granulates which may readily be mixed with e.g. food or feed components, or more preferably, form a component of a pre-mix. The particle size of the enzyme granulates preferably is compatible with that of the other components of the mixture. This provides a safe and convenient means of incorporating enzymes into e.g. animal feed.

Agglomeration granulates are prepared using agglomeration technique in a high shear mixer (e.g. Lödige) during which a filler material and the enzyme are co-agglomerated to form granules. Absorption granulates are prepared by having cores of a carrier material to absorb/be coated by the enzyme.

Typical filler materials are salts such as disodium sulphate. Other fillers are kaolin, talc, magnesium aluminium silicate and cellulose fibers. Optionally, binders such as dextrins are also included in agglomeration granulates.

Typical carrier materials are starch, e.g. in the form of cassava, corn, potato, rice and wheat. Salts may also be used.

Optionally, the granulates are coated with a coating mixture. Such mixture comprises coating agents, preferably hydrophobic coating agents, such as hydrogenated palm oil and beef tallow, and if desired other additives, such as calcium carbonate or kaolin.

Additionally, phytase compositions may contain other substituents such as colouring agents, aroma compounds, stabilizers, vitamins, minerals, other feed or food enhancing enzymes, i.e. enzymes that enhance the nutritional properties of feed/food, etc. This is so in particular for the so-called pre-mixes.

A "food or feed additive" is an essentially pure compound or a multi component composition intended for or suitable for being added to food or feed. In particular it is a substance which by its intended use is becoming a component of a food or feed product or affects any characteristics of a food or feed product. It is composed as indicated for phytase compositions above. A typical additive usually comprises one or more compounds such as vitamins, minerals or feed enhancing enzymes and suitable carriers and/or excipients.

In a preferred embodiment, the phytase compositions of the invention additionally comprises an effective amount of one or more feed enhancing enzymes, in particular feed enhancing enzymes selected from the group consisting of alpha-galactosidases, beta-galactosidases, in particular lactases, other phytases, beta-glucanases, in particular beta-1,4-endoglucanases and beta-1,3(4)-endoglucanases, cellulases, xylosidases, galactanases, in particular arabinogalactan beta-1,4-endogalactosidases and arabinogalactan beta-1,3-endogalactosidases, endoglucanases, in particular beta-1,2-endoglucanase, alpha-1,3-endoglucanase, and beta-1,3-endoglucanase, pectin degrading enzymes, in particular pectinases, pectinesterases, pectin lyases, polygalacturonases, arabinanases, rhamnogalacturonases, rhamnogalacturonan acetyl esterases, rhamnogalacturonan-alpha-rhamnosidase, pectate lyases, and alpha-galacturonisidases, mannanases, beta-mannosidases, mannan acetyl esterases, xylan acetyl esterases, proteases, xylanases, arabinoxylanases and lipolytic enzymes such as lipases, phospholipases and cutinases.

The animal feed additive of the invention is supplemented to the mono-gastric animal before or simultaneously with the diet. Preferably, the animal feed additive of the invention is supplemented to the mono-gastric animal simultaneously with the diet. In a more preferred embodiment, the animal feed additive is added to the diet in the form of a granulate or a stabilized liquid.

An effective amount of phytase in food or feed is from about 10-20.000; preferably from about 10 to 15.000, more preferably from about 10 to 10.000, in particular from about 100 to 5.000, especially from about 100 to about 2.000 FYT/kg feed or food.

Examples of other specific uses of the phytase of the invention are in soy processing and in the manufacture of inositol or derivatives thereof.

The invention also relates to a method for reducing phytate levels in animal manure, wherein the animal is fed a feed comprising an effective amount of the phytase of the invention.

Also comprised in this invention is the use of a phytase of the invention during the preparation of food or feed preparations or additives, i.e. the phytase exerts its phytase activity during the manufacture only and is not active in the final food or feed product. This aspect is relevant for instance in dough making and baking.

The invention relates to a phytase variant which, when aligned according to FIG. 1, is amended as compared to a model phytase in at least one of the following positions, using the position numbering corresponding to P_lycii: 24; 27; 31; 33; 39; 40; 41; 42; 43; 44; 45; 46; 47; 49; 51; 56; 58; 59; 61; 62; 68; 69; 70; 71; 72; 73; 74; 75; 76; 77; 78; 79; 80; 81; 82; 83; 84; 88; 90; 102; 115; 116; 117; 118; 119; 120; 121; 122; 123; 124; 125; 126; 127; 128; 132; 143; 148; 149; 150; 151; 152; 153; 154; 155; 156; 157; 158; 159; 160; 161; 162; 163; 170f; 170g; 171; 172; 173; 184; 185; 186; 187; 187a; 190; 191; 192; 193; 194; 195; 198; 199; 200; 201; 201a; 201b; 201c; 201d; 201e; 201f; 202; 203; 203a; 204; 205; 211; 215; 220; 223; 228; 232; 233; 234; 235; 236; 237; 238; 239; 242; 243; 244; 246; 251e; 253; 256; 260; 264; 265; 267; 270; 271; 272; 273; 274; 275; 276; 277; 278; 279; 280; 283; 285; 287; 288; 292; 293; 302; 304; 332; 333; 334; 335; 336; 337; 338; 339; 340; 341; 342; 343; 348; 349; 352; 360; 362; 364; 365; 366; 367; 368; 369; 370; 371; 372; 373; 374; 375; 376; 383k; 387; 393; 394; 396; 404; 409; 411; 412; 413; 417; 421; 431.

From these variants we expect amended characteristics, preferably amended activity characteristics. In fact, for several variants such amended characteristics have already been shown (see the experimental part). Like above, "amended" means as compared to the model phytase. "Amended activity characteristics" means amended in at least one phytase activity related respect, such as (non-exclusive list): pH stability, temperature stability, pH profile, temperature profile, specific activity (in particular in relation to pH and temperature), substrate specificity, substrate cleavage pattern, substrate binding, position specificity, the velocity and level of release of phosphate from corn, reaction rate, phytate degradation rate), end level of released phosphate reached.

Preferred amended activity characteristics are amended specific activity, preferably increased, and preferably increased at a pH of 3, 4, 5, or 6; amended pH or temperature profile; and/or amended, preferably increased, thermostability, e.g. of an increased melting temperature as measured using DSC.

Preferred phytase variants are: Phytase variants which, when aligned according to FIG. 1, are amended as compared to a model phytase in at least one of the following positions, using the position numbering corresponding to P_lycii: 43; 44; 47; 51; 58; 62; 78; 80; 83; 88; 90; 102; 143; 148; 153; 154; 186; 187a; 195; 198; 201e; 204; 205; 211; 215; 220; 242; 244; 251e; 260; 264; 265; 267; 270; 273; 278; 302; 336; 337; 339; 352; 365; 373; 383k; 404; 417.

The following variants of A_fumigatus constitute a subgroup: Q43L; Q270L; G273D,K; N336S; A205E; Y278H; Q43L+Q270L; Q43L+Q270L+G273D; Q43L+Q270L+G273D+N336S; G273K+A205E; G273K+A205E+Y278H (see EP 0897010).

Generally, variants of the invention can be deduced or identified as follows: Looking at the alignment according to FIG. 1, comparing two sequences, one of which is a model phytase with improved properties, identifying amino acid differences in relevant positions/areas, and transferring (substituting with) from the model to the other phytase sequence the amino acid in a relevant position.

The invention also relates to a process for preparing a phytase variant which includes the above method, and further includes the deducement and synthesis of the corresponding DNA sequence, the transformation of a host cell, the cultivation of the host cell and the recovery of the phytase variant.

Relevant positions/areas include those mentioned below in relation to important phytase activity characteristics such as specific activity, thermostability, pH activity/stability.

The present invention also relates to phytase variants (varied according to a model phytase as defined herein) which are obtainable, preferably obtained, by the process outlined above and which are expected to exhibit an amended characteristic/property, preferably does exhibit such amended characteristic, e.g. an improved specific activity.

At least the basidiomycete model phytases P_lycii and T_pubescens exhibit a high specific activity (as determined using the method of Example 2 herein).

This is an example of a desired property which can be transferred to other phytases, e.g. the other phytases listed in FIG. 1, in particular to the A_pediades and the ascomycete phytases such as A_fumigatus, A-ficuum, consphyA, by a deducement process such as the one mentioned above.

Thus, amended specific activity, in particular an improved specific activity, in particular at low pH and/or high temperature, is expected from variants, which have been amended in relevant areas, viz. (i) in the amino acid residues which point into the active site cleft; or (ii) in the amino acid residues in the close neighbourhood of these active site residues. Preferably, close neighbourhood means within 10 Angstroms from the active site residues.

From the pdb file 1IHP (Brookhaven Database entry of 18.03.98 re 1IHP, Structure of Phosphomonoesterase, D. Kostrewa; or as published in Nature Structural Biology, 4, 1997, p. 185-190), active site regions can be identified, using the program INSIGHTII from Molecular Simulations MSI, San Diego, Calif., and using the subset command, an "active site shell" can be defined comprising those amino acid residues which lie close to the catalytic residues, defined as H59, D339 and R58 in *A. ficuum* phytase (corresponding to Peniophora numbers H71, D335 and R70, respectively). An "active site shell (10 Angstroms)" comprises those residues which lie within 10 Angstroms from the above catalytic residues.

The residues within 10 Angstroms from H71 and D335 are the following (using Peniophora numbers) : 41-47, 68-77, 115-118, 120-126, 128, 149-163, 185, 191-193, 199, 243, 270-271, 273-275, 277-279, 288, 332-343, 364-367, 369-375, 394 ("the active site shell (10 Angstroms)").

Preferably, a "substrate binding shell" can also be defined which comprises those residues which are in close proximity to the substrate binding site and which can therefore be expected to be in contact with the substrate.

This information can be deduced as described above, by docking a sugar analogue to phytin into the active site cleft (the residues making up the surface of the active site). If a sugar without any phosphate groups is docked into the active site cleft, e.g. alpha-D-glucose (chair conformation, structure provided by the INSIGHTII program), using a fixed distance as shown below, the residues pointing towards the active site cleft can be extracted using the subset command and using a distance of 10 Angstroms from the substrate analogue. Alternatively, the compound inositol-1,4,5-triphosphate (Brookhaven database file 1djx. Inositol-1,4,5-triphosphate) can be docked into the active site cleft. This compound and glucose, however, are more or less superimposable.

The distances in Angstroms are: From oxygen atom in position 6 of the alpha-D-glucose to

| atom ND1 of H59: | 5.84 |
| atom NH2 of R58: | 6.77 |
| atom NH2 of R142: | 5.09 |
| atom ND2 of N340: | 3.00 |
| atom ND1 of H59: | 7.76 |
| atom NH2 of R58: | 8.58 |

(the Peniophora numbers of the above residues are: H71, R70, R155, N336, H71 and R70, respectively).

In this way, the residues in contact with the substrate are identified as follows (Peniophora numbers) : 43-44; 70-80; 83-84; 115; 153; 155-156; 184; 191-192; 198-202; 205; 235; 238; 242; 270; 272-273; 275-277; 332-336; 338; 369; 371 ("the substrate binding shell (10 Angstroms)").

Variants being amended in one or more of (1) the active site shell or (2) the substrate binding shell are strongly expected to have an amended specific activity. This leads to the following joint grouping of positions (still Peniophora numbers and 10 Angstrom shells) : 41-47, 68-80, 83-84, 115-118, 120-126, 128, 149-163, 184-185, 191-193, 198-201e, 202-203, 205, 235-236, 238-239, 242-243, 270-279, 285, 288, 332-343, 364-367, 369-375, 394.

Preferably, the active site shell and the substrate binding shell are defined as described above using the basidiomycete model phytases of FIG. 1, the Peniophora phytase being a preferred model. A deducement of corresponding variants of other model phytases is possible using the alignment of FIG. 1.

In a preferred embodiment, a distance of 5 Angstroms is used in the subset command, thus defining active site and substrate binding shells of a more limited size, e.g. an active site shell comprising the residues 43-44, 69-74, 117, 125, 155-156, 159, 274, 332-340, 370-374 (5 Angstroms from H71 and D335), "active site shell (5 Angstroms)".

Generally the active site shell and substrate binding shell regions form the basis for selecting random mutagenesis regions. Examples of preferred random mutagenesis regions are regions 69-74, 332-340, 370-374, doping to be added (a 5 Angstrom approach); and regions 57-62, 142-146, 337-343, doping to be added (a 10 Angstrom approach).

It is presently contemplated that any amendment in either of these positions will lead to a phytase of amended characteristics, e.g. of an amended specific activity.

The above expression "any amendment in either of the positions" is considered fully equivalent to listing each position and each substitution, e.g. as follows for the above sub-group 41-47: 41A,C,D,E,F,G,H,I,K,L,M,N,P,Q,R,S,T,V,W,Y; 42A,C,D,E,F,G,H,I,K,L,M,N,P,Q,R,S,T,V,W,Y; 43A,C,D,E,F,G,H,I,K,L,M,N,P,Q,R,S,T,V,W,Y; 44A,C,D,E,F,G,H,I,K,L,M,N,P,Q,R,S,T,V,W,Y; 45A,C,D,E,F,G,H,I,K,L,M,N,P,Q,R,S,T,V,W,Y; 46A,C,D,E,F,G,H,I,K,L,M,N,P,Q,R,S,T,V,W,Y; 47A,C,D,E,F,G,H,I,K,L,M,N,P,Q,R,S,T,V,W,Y.

In a preferred embodiment, amended specific activity is expected from the following variants:

42S,G; 43A,C,D,E,F,G,H,I,K,L,M,N,P,Q,R,S,T,V,W,Y; 45D,S; 47Y,F; 51E,A; 75W,F; 78S,D; 79G; 80K,A; 83I,Q; 84Q,V; 116S; 118V,L; 119E; 120L; 122A; 123N,T; 125S; 126H,S; 127Q,E; 128A,T; 151A,S; 152G; 153D,Y; 154Q,D,G; 157V; 158D,A; 159T; 160A,S; 161T,N; 162N; 163W; 184Q,S; 186A,E; 198A,N; 200G,V; 201D; deletions of one or more of 201a, 201b, 201c, 201d, 201e, 201f—preferably all; 202S; 205Q,E; 235Y,L; 238L,M; 242P; 270Y,A,L; 271D; 273D,K; 275F,Y; 278T,H; 332F; 336S; 337T,Q; 339V; 340P,A; 343A,S; 364W,F; 365V,L; 366D,V; 367K; 368K; 369I,L; 370V; 373S; 374A; 375H; 376M; 393V.

Particularly preferred variants are the following: 78S; 79G; 80A; 83I,Q; 84Q,V; 198A,N; 200G,V; 201D; deletions in one or more of 201a, 201b, 201c, 201d, 201e, 201f—preferably all deletions; 202S; 205Q,E; 235Y,L; 238L,M; 242P, 273D; 275F,Y.

Other particularly preferred variants are the following: 43A,C,D,E,F,G,H,I,K,L,M,N,P,Q,R,S,T,V,W,Y; in particular 43M,P; 75W,F; 80K; 153D; 184Q,S; 270Y,A; 332F; 369I,L.

The following variants are especially preferred: 43L,G, N,V,A,I,T; 78D; 153Y; 154G; 270L; 273D,K. Double and triple variants (43L/270L); (43L/270L/273D); (43L/78D) and (43L/153Y/154G) are also especially preferred. Other preferred variants are 205E; 278H; 336S.

These especially preferred single, double and triple variants are preferably variants of model phytases which can be aligned to FIG. 1, in particular variants of the specific model phytases listed in FIG. 1.

At least consphyA is known to have a high thermostability. Still further, the thermostability of *P_lycii* is rather high.

This is an example of a desired property which can be transferred to other phytases, e.g. the other phytases listed in FIG. 1, in particular to the basidiomycete phytases such as P_lycii and A_pediades, by a deducement process such as the one mentioned above.

Amended thermostability, in particular improved thermostability, is expected on this background from the following variants:

39H,S; 40L,N; 43P; 47Y,F; 49P; 51E,A; 56P; 58D; 61R; 62V; 80K; 83A; 84Y; 172P; 184P; 195T; 198A; 204V; 211L; 223D; 236Y; 242P; 246V; 253P; 264R; 265Q; 280A,P; 283P; 287A; 292F,Y; 293A; 302R; 304P; 337S; 348Y; 387P; 396R; 409R; 411K; 412R; 417E; 421F,Y.

The following variants of amended thermostability are particularly preferred: 39S; 40N; 47Y,F; 51A; 83A; 195T; 204V; 211L; 242P; 265A.

Further variants of amended thermostability are the following: 42G; 43T,L,G; 44N; 58K,A; 59G; 62I; 69Q; 75F; 78D; 79G; 80A; 81A,G; 82T; 83K,R; 84I; 88I; 90R,A; 102Y; 115N; 118V; 122A; 123Q,N; 125M,S; 126V,S; 127N,Q; 128S,A; 143N,K; 148V,I; 154S; 158D; 170fH; 170gA; 171T,N; 172N; 173W, 184S; 186A; 187A; 187aS; 193S; 195V,L; 198V; 201E; 201eT; 202A, 203aT; 204A; 211V, 215P,A; 220L,N; 223H; 228N; 232T; 322E; 235T; 236N; 242S; 244D; 251eQ,E; 256D; 264I; 260A,H; 265A; 267D; 270G; 271D; 273K,D; 278T,H; 287T; 293V; 302H; 337T,G; 338I; 339V,I; 340A; 352K; 365A,S; 366S; 367A; 369L; 373S,A; 374S; 376M; 383kE,Q; 404G,A; 411T; 417R; 431E.

Other concepts of the invention, which can be expected to impart an improved thermostability to a phytase, are as follows—considering the 1IHP structure previously referred to and transferring via an alignment according to FIG. 1 as outlined herein:

(A) Introduction of proline residues in spatial positions where the prolin special dihedral angles are satisfied and the hydrogen bonding network are not hampered and no steric clashes are observed.
(B) Filling up holes: By substitution for bigger residues in internal cavities an improvement in stability can often be obtained.
(C) Cystin bridge: Cystin bridges will often make the proteins more rigid and increase the energy of unfolding.

Further variants from which amended thermostability is expected according to these concepts of (A) to (C) are: 27P, 31Y, 132F, 132I, 132L, 184P, 186P, 190P, 280P, 343F, 343I, 343L, 349P, 362P and (33C and 24C).

Concept (A): 27P, 184P, 186P, 190P, 349P, 362P.
Concept (B): 343F,I,L; 31Y; 132F,I,L; 273F.
Concept (C): 33C/24C.

Amended pH activity or stability, preferably stability, in particular at low pH, in particular improved, is another desired property which can be transferred by aligning according to FIG. 1 and transferring from models of improved pH profiles to other phytases—as outlined above.

Other concepts of the invention, which can be expected to impart an improved stability at low pH to a phytase, are as follows—considering the lIHP structure previously referred to and transferring via an alignment according to FIG. 1 as outlined herein:

(D) Surface charges: Better distribution at low pH, to avoid cluster of negative or positive, and to avoid too close same charged residues.
(E) Prevent deamidation: Surface exposed Q or N in close contact to negative charged residues.

Phytase variants having improved pH stability/activity at low pH are expected to be: 39H; 39Q; 80A; 203R; 271N; 51R; 154S; 185S; 194S; 194T; 288L; 288I; 288F; 360R; 173Q,S; 204Q,S; 303K,S; 81Q,E.

Concept (D): 203R, 271N; 51R; 185S; 360R; 173Q,S; 204Q,S; 303K,S; 81Q,E.

Concept (E): 154S; 194S,T; 288L,I,F.

A preferred model phytase for these concepts of (D) and (E) is P_lycii.

Experimentally proven to have a lowered pH optimum is: Variant 80A of ascomycete phytases, in particular of A_fumigatus and consphyA.

Especially preferred single, double and triple variants are 43L; (43L/270L) and (43L/270L/273D). These variants have a changed pH profile. They are preferably variants of the specific model phytases listed in FIG. 1.

For all preferred variants listed above:
the stability is preferably amended at high temperature, viz. in the temperature range of 50-100° C., in particular 60-90° C., more preferably in the range of 70-90° C.;
the activity is preferably amended in a temperature range relevant for the use in the gastro-intestinal system of animals, e.g. 30-40° C., more preferably 32-38° C., most preferably in the range of 35-38° C.;
the stability is preferably amended at low pH, viz. in the pH range of pH 1.5-7, preferably 2-6, more preferably 3-5;
the activity is preferably amended in the pH range of pH 1.5-5.5, more preferably at pH 2.5-4.5, still more preferably 3-5.

Tests for amended phytase characteristics, such as those mentioned above, are well known in the art and any such test can be used to compare the performance of the phytase variants with the phytase models.

A preferred test for specific activity is given in Example 2. Preferred tests for pH and temperature activity and stability are given in Example 3. An even more preferred test for thermal stability is the DSC method of Example 4.

WO 98/28409 discloses tests for various other parameters, too, such as position specificity. All the tests of WO 98/28409 are preferred tests.

Generally, of course all these tests can be conducted at desired pH values and temperatures.

In the dependent claims, some preferred phytase variants based on five of the thirteen herein specifically disclosed model phytases are specified.

In an analogous way other preferred variants based on the remaining eight specifically disclosed model phytases can easily be deduced by combining the suggested amendments with each of the corresponding sequences of FIG. 1. These preferred variants are specifically included in the present invention, and they are easily deduced, viz. the following:

Variants of a model phytase derived from Paxillus, preferably Paxillus involutus, preferably derived from strain CBS 100231, preferably variants of P_involtus-A1, the sequence of which is shown at FIG. 2, said variants comprising at least one of the following amendments:
( )24C; T27P; F31Y; I33C; R39H,S,Q; N40L; S42G; P43A,C,D,E,F,G,H,I,K,L,M,N,Q,R,S,T,V,W,Y; Y44N; S45D; Y47F; A51E,R; A58D;K; Q61R; I62V; F75W; S78D; A80K; T81Q,E,G,A; R83A,I,Q,K; I84Y,Q,V; L88I; K90R,A; F102Y; S115N; D116S; V118L; P119E; F120L; A123N,T,Q; S125M; F126H,S,V; D127Q,E,N; A128T,S; A132F,I,L; I148V; D151A,S; S153D,Y; D154Q,S,G; D158A; S159T; A160S; T161N; ( )170fH; ( )170gA; S171N; H172P; N173Q,S; P184Q,S; Q185S; T186A,E,P; G187A; ( )187aS; T190P,A; D193S; N194S,T; M195T,V,L; A198N,V; G200V; D201E; ( )201eT; S202A; D203R,K,S; P203aV,T; Q204E,S,A,V; V205E; V211L; S215A,I; L220N; A223D,H; D233E; F235Y,L,T; N236Y; L237F;

V238L,M; A242P,S; M244D; ( )251eE,Q; D253P; T256D; P260A,H; E264R,I; A265Q; A267D; G270Y,A, L; D271N; D273K; F275Y; T278H; Y280A,P; E283P; V287A,T; Q288L,I,F; Y292F; V293A; N302R,H; A304P; N336S; L337T,Q,S,G; M 338I; V339I; A340P; S343A,F, I,L; F348Y; R349P; A352K; P360R; R362P; W364F; R365V,L,A,S; T366D,V,S; S367K,A; S368K; L369I; S373A; G374A,S; R375H; ( )383kQ,E; T387P; Q396R; G404A; L409R; T411K; L412R; E417R; F421Y.

Variants of a model phytase derived from a species of the genus *Paxillus*, preferably the species *Paxillus involutus*, preferably derived from strain CBS 100231, preferably variants of *P_involtus*-A2, the sequence of which is shown at FIG. 3, said variants comprising at least one of the following amendments:

P24C; I27P; F31Y; I33C; R39H,S,Q; N40L; S42G; P43A, C,D,E,F,G,H,I,K,L,M,N,Q,R,S,T,V,W,Y; Y44N; S45D; Y47F; A51E,R; A58D,K; E61R; I62V; F75W; S78D; A80K; A81Q,E,G; R83A,I,Q,R,K; I84Y,Q,V; L88I; K90R,A; F102Y; S115N; D116S; V118L; P119E; F120L; A123N,T,Q; S125M; F126H,S,V; D127Q,E,N; A128T,S; V132F,I,L; D143N; I148V; D151A,S; S153D,Y; D154Q, S,G; D158A; A160S; T161N; ( )170fH; ( )170gA; S171N; R172P; N173Q,S; P184Q,S; Q185S; T186A,E,P; G187A; ( )187aS; T190P,A; D193S; N194S,T; M195T,V,L; A198N,V; G200V; E201D; ( )201eT; S202A; D203R,K, S; P203aV,T; Q204E,S,A,V; V205E; S211L,V; S215A,P; L220N; A223D,H; A232T; F235Y,L,T; N236Y; L237F; V238L,M; P242S; M244D; ( )251eE,Q; D253P; T256D; P260A,H; E264R,I; A265Q; A267D; G270Y,A,L; D271N; D273K; F275Y; T278H; Y280A,P; A283P; V287A,T; Q288L,I,F; Y292F; I293A,V; N302R,H; A304P; N336S; L337T,Q,S,G; M338I; V339I; 340P,A; A343S,F,I,L; F348Y; R349P; A352K; P360R; R362P; W364F; L365V,A,S; T366D,V,S; S367K,A; S368K; V369I,L; S373A; R375H; ( )383kQ,E; T387P; Q396R; G404A; L409R; A411K,T; L412R; E417R; Y421F.

Variants of a model phytase derived from a species of the genus *Trametes*, preferably the species *Trametes pubescens*, preferably derived from strain CBS 100232, preferably variants of *T_pubescens*, the sequence of which is shown at FIG. 4, said variants comprising at least one of the following amendments:

R24C; T27P; L31Y; V33C; Q39H,S; S40L,N; S42G; M43A, C,D,E,F,G,H,I,K,L,N,P,Q,R,S,T,V,W,Y; Y44N; S45D; Y47F; A51E,R; A58D,K; S59G; Q61R; I62V; F75W; S78D; A80K; A81Q,E,G; R83A,I,Q,K; I84Y,Q,V; V88I; K90R,A; L102Y; D115N; V118L; T123N,Q; S125M; S126H,V; E127Q,N; A128T,S; A132F,I,L; D143N; V148I; S151A; S153D,Y; D154Q,S,G; A158D; A160S; N161T; ( )170fH; ( )170gA; S171N; S172P; N173Q,S; S184Q,P; E185S; A186E,P; G187A; ( )187aS; T190P,A; N194S,T; M195T,V,L; A198N,V; G200V; ( )201eT; S202A; D203R,K,S; P203aV,T; Q204E,S,A,V; V20SE; Q211L,V; P215A; L220N; G223D,H; D233E; Y235L,T; N236Y; L237F; L238M; P242S; E244D; ( )251eE,Q; E253P; Q260A,H; D264R,I; A265Q; A267D; A270Y,L, G; D271N; D273K; F275Y; T278H; Y280A,P; V287A,T; Q288L,I,F; Y292F; I293A,V; A302R,H; N304P,A; N336S; Q337T,S,G; M338I; V339I; A340P; S343A,F,I,L; F348Y; N349P; A352K; P360R; R362P; F364W; L365V, A,S; V366D,S; K367A; I369L; A373S; A374S; R375H; ( )383kQ,E; Q387P; A396R; G404A; V409R; T411K; L412R; E417R; Y421F.

Variants of a model phytase derived from a species of the genus *Aspergillus*, preferably the species *Aspergillus nidulans*, preferably derived from strain DSM 9743, preferably variants of *A_nidulans*, the sequence of which is shown at FIG. 10, said variants comprising at least one of the following amendments:

V24C; A27P; H39S,Q; V40L,N; G42S Q43A,C,D,E,F,G,H, I,K,L,M,N,P,R,S,T,V,W,Y; Y44N; S45D; Y47F; S49P; E51A,R; V56P; H58D,K,A; E61R; V62I; S69Q; Y75W,F; E78D,S; S79G; K80A; S81Q,E,A,G; K82T; A83I,Q,K,R; Y84Q,V,I; A90R; D115N; D116S; T118V,L; I119E; F120L; E122A; N123T,Q; M125S; V126H,S; D127Q,E, N; S128A,T; F132I,L; K143N; I148V; S151A; S153D,Y; D154Q,S,G; A158D; S159T; A160S; E161T,N; K162N; F163W; G170fH; S170gA; ( )171N; ( )172P; K173Q,S; P184Q,S; E185S; I186A,E,P; D187A; G187aS; T190P,A; H193S; S194T; S198A,N,V; E200G,V; N201D,E; D201e( ); E201e( ),T; R201f( ) (a deletion of at least one of 201d, 201e, 201f, preferably all); A202S; D203R,K,S; E203aV,T; I204Q,E,S,A,V; I211L,V; P215A; L220N; D223H; K228N; E232T; N233E; I235Y,L,T; Y236N; L237F; M238L; S242P; M246V; E251eQ; A256D; E260A,H; L264R,I; Q270Y,A,L,G; S271D,N; S273D,K; Y275F; G278T,H; A280P; A287T; Q288L,I,F; F292Y; T293A,V; Q302R,H; P304A; N336S; S337T,Q,G; M338I; I339V; S340P,A; F343A,S,I,L; N349P; Q352K; S360R; Q362P; Y364W,F; A365V,L,S; A366D,V,S; S367K,A; W368K; T369I,L; G373S,A; A374S; R375H; A376M; E383kQ; A404G; T411K; L412R; E417R; F421Y; K431E.

Variants of a model phytase derived from a species of *Aspergillus*, preferably *Aspergillus terreus*, preferably derived from strain CBS 220.95, preferably variants of *A_terreus*, the sequence of which is shown at FIG. 12, said variants comprising at least one of the following amendments:

G24C; V27P; H39S,Q; K40L,N; G42S; L43A,C,D,E,F,G, H,I,K,M,N,P,Q,R,S,T,V,W,Y; Y44N; A45D,S; Y47F; S49P; Q51E,A,R; V56P; P58D,K,A; D59G; H61R; I62V; A69Q; S75W,F; H78D,S; S79G; K80A; T81Q,E,A,G; A83I,Q,K,R; Y84Q,V,I; A90R; E115N; E116S; T118V,L; P119E; F120L; R122A; N123T,Q; L125S,H; R126H,S,V; D127Q,E,N; L128A,T,S; F132I,L; H143N; V148I; T151A,S; D152G; A153D,Y; S154D,Q,G; H157V; E158D,A; S159T; A160S; E161T,N; K162N; F163W; H173Q,S; P184Q,S; E185S; G186A,E,P; S187A; A187aS; T190P,A; H193S; S194T; L195T,V; A198N,V; E200G,V; S201D,E; S201d( ); T201e( ); V201f( ); G202S,A; D203R,K,S; D203aV,T; A204Q,E,S,V; V205E; V211L; A215P; L220N; D223H; Q228N; D232T; D233E; V235Y,L,T; N236Y; L237F; M238L; P242S; E244E; T251eE,Q; A260H; T264R,I; Q265A; N267D; L270Y,A, G; S271D,N; K273D; Y275F; H278T; G280A,P; V287A, T; Q288L,I,F; W292F,Y; A293V; Q302H; P304A; N337T, Q,S,G; L338I; V339I; S340P,A; W343A,S,F,I,L; N349P; A352K; S360R; S362P; Y364W,F; A365V,L,S; A366D, V,S; A367K; W368K; T369I,L; A373S; A374S; R375H; A376M; R383kQ,E; P404A,G; K411T; A417E,R; F421Y; A431E.

Variants of a model phytase derived from a species of *Talaromyces*, preferably the species *Talaromyces thermophilus*, preferably derived from strain ATCC 20186 or ATCC 74338, preferably variants of T_thermo, the sequence of which is shown at FIG. 13, said variants comprising at least one of the following amendments:

H24C; V27P; H39S,Q; S40L,N; G42S; Q43A,C,D,E,F,G,H, I,K,L,M,N,P,R,S,T,V,W,Y; Y44N; S45D; F47Y; S49P; A51E,R; V56P; Q58D,K,A; N59G; K61R; I62V; Y75W, F; S78D; S79G; K80A; T81Q,E,A,G; E82T; L83A,I,Q, R,K; Y84Q,V,I; R90A; D116S; T118V,L; P119E; F120L;

E122A; N123T,Q; M125S; I126H,S,V; Q127E,N; L128A,T,S; F132I,L; V148I; S151A; S153D,Y; D154Q, S,G; I157V; A158D; S159T; G160A,S; R161T,N; L162N; F163W; S170gA; D171N; K172P; H173Q,S; E184Q,S,P; E185S; G186A,E,P; D187A; T190P,A; T193S; G194S,T; S195T,V,L; V198A,N; E200G,V; D201E; S201d( ); S201e( ),T; S201f( ); G202S,A; H203R,K,S; D203aV,T; A204Q,E,S,V; Q205E; Q211L,V; A215P; I220N,L; H223D; D228N; S232T; D233E; P235Y,L,T; Y236N; M237F; D238L,M; P242S; E244D; L246V; ( )251eE,Q; A256D; Q260A,H; Q264R,I; A265Q; Q270Y,A,L,G; S271D,N; G273D,K; Y275F; N278T,H; G280A,P; A287T; Q288L,I,F; F292Y; V293A; H302R; P304A; N336S; T337Q,S,G; M338I; T339V,I; S340P,A; A343S, F,I,L; N349P; A352K; S360R; E362P; Y364W,F; S365V, L,A; A366D,V,S; A367K; W368K; T369I,L; G373S,A; G374A,S; R375H; A376M; D383kQ,E; E404A; K411T; R417E; F421Y.

Variants of a model phytase derived from a species of *Thermomyces*, preferably the species *Thermomyces lanuginosus*, preferably derived from strain DBS 586.94, preferably variants of *T_lanuginosa*, the sequence of which is shown at FIG. 14, said variants comprising at least one of the following amendments:
K24C; ( )27P; ( )31Y; ( )33C; R39H,S,Q; H40L,N; G42S; Q43A,C,D,E,F,G,H,I,K,L,M,N,P,R,S,T,V,W,Y; Y44N; S45D; F47Y; S49P; A51E,R; V56P; K58D,A; V62I; S69Q; Y75W,F; A78D,S; H79G; K80A; S81Q,E,A,G; E82T; V83A,I,Q,K,R; Y84Q,V,I; L88I; R90A; F102Y; D115N; N116S; T118V,L; R119E; F120L; E122A; E123N,T,Q; M125S; M126H,S,V; E127Q,N; S128A,T; F132I,L; E143N; V148I; A151S; S153D,Y; A154D,Q,S, G; I157V; A158D; S159T; A160S; E161T,N; F162N; F163W; R170fH; S170gA; K172P; D173Q,S; S184Q,P; E185S; E186A,P; T187A; G187aS; T190P,A; G193S; L194S,T; T195V,L; A198N,V; E200G,V; E201D; A201d( ); P201e( ),T; D202S,A; P203R,K,S; T203aV; Q204E,S,A,V; P205E; V211L; R215A,P; I220L,N; H223D; E232T; D233E; P235Y,L,T; L236Y,N; M238L; P242S; Q251eE; H256D; Q260H; M264R,I; A265Q; Y270A,L,G; T271D,N; D273K; Y275F; H278T; G280A, P; A283P; S287A; R288L,I,F; F292Y; V293A; G302R,H; P304A; N336S; T337Q,S,G; M338I; T339V,I; G340P,A; S343A,F,I,L; N349P; P360R; T362P; Y364W,F; A365V, L,S; A366D,V,S; S367K,A; W368K; T369I,L; A373S; A374S; R375H; A376M; E383kQ; R404A,G; R411K,T; K417E,R; F421Y; D431E.

Variants of a model phytase derived from a species of *Myceliophthora*, preferably the species *Myceliophthora thermophila*, preferably derived from strain ATCC 48102 or ATCC 74340, preferably variants of *M_thermophila*, the sequence of which is shown at FIG. 7, said variants comprising at least one of the following amendments:
S24C; F31Y; H39S,Q; F40L,N; G42S; Q43A,C,D,E,F,G,H, I,K,L,M,N,P,R,S,T,V,W,Y; Y44N; S45D; Y47F; S49P; P51E,A,R; I56P; D58K,A; D59G; E61R; V62I; S69Q; A75W,F; L78D,S; K79G; R80K,A; A81Q,E,G; A82T; S83A,I,Q,K,R; Y84Q,V,I; R90A; D115N; E116S; T118V, L; R119E; T120L; Q122A; Q123N,T; M125S; V126H,S; N127Q,E; S128A,T; F132I,L; K143N; V148I; A151S; Q153D,Y; D154Q,S,G; H158D,A; S159T; A160S; E161T,N; G170fH; S170gA; T171N; F163W; V172P; R173Q,S; P184Q,S; E185S; T186A,E,P; G187aS; T190P, A; N193S; D194S,T; L195T,V; A198N,V; E200G,V; E201D; G201a( ); P201b( ); Y201c( ); S201d( ); T201e( ); I201f( ); G202S,A; D203R,K,S; D203aV,T; A204Q,E,S,V; Q205E; T211L,V; P21SA; V220N,L; N223D,H; A232T; D233E; V235Y,L,T; A236Y,N; L237F; M238L; P242S; E244D; A251eE,Q; R256D; E260A,H; R264I; A265Q; Q270Y,A,L,G; S271D,N; K273D; Y275F; Y278T,H; P280A; T287A; Q288L,I,F; F292Y; V293A; ( )302R,H; P304A; N336S; D337T,Q,S,G; M338I; M339V,I; G340P,A; G343A,S,F,I,L; D349P; P352K; D360R; E362P; Y364W,F; A365V,L,S; A366D, V,S; S367K,A; W368K; A369I,L; A373S; A374S; R375H; I376M; E383kQ; E387P; G404A; M409R; T411K; L412R; E417R; F421Y; D431E.

This invention also provides a new phytase which has been derived from a strain of *Cladorrhinum*, viz. *C. foecundissimum*. Accordingly, the invention also relates to a polypeptide having phytase acitivity and which comprises SEQ ID NO: 2 or the mature part (amino acids nos 16-495) thereof; or a polypeptide being at least 70, more preferably 75, 80, 85, 90, 95% homologous thereto; homology meaning similarity, preferably identity, and being determined using the program GAP and the settings as defined hereinabove. And the invention relates to a DNA construct which encodes a polypeptide having phytase activity, said DNA construct comprising a DNA molecule which comprises SEQ ID NO: 1 or nucleotides nos. 20-70 and 207-1560 thereof; or nucleotides nos. 20-70 and 207-1563 thereof; or nucleotides nos. 65-70 and 207-1560 thereof; or nucleotides nos. 65-70 and 207-1563 thereof; or a DNA construct or molecule which is at least 70, 75, 80, 85, 90, 95% homologous to either of these nucleotide sequences; homology meaning similarity, preferably identity, and being determined using computer programs known in the art such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453). Using GAP with the following settings for DNA sequence comparison: GAP creation penalty of 5.0 and GAP extension penalty of 0.3. The invention also relates to a DNA construct which hybridizes with any of the above DNA sequences under the conditions mentioned hereinabove.

EXAMPLES

Example 1

Phytase Activity Assay (FYT)

Phytase activity can be measured using the following assay: 10 microliter diluted enzyme samples (diluted in 0.1 M sodium acetate, 0.01% Tween20, pH 5.5) are added into 250 microliters 5 mM sodium phytate (Sigma) in 0.1 M sodium acetate, 0.01% Tween20, pH 5.5 (pH adjusted after dissolving the sodium phytate; the substrate is preheated) and incubated for 30 minutes at 37° C. The reaction is stopped by adding 250 microliters 10% TCA and free phosphate is measured by adding 500 microliters 7.3 g $FeSO_4$ in 100 ml molybdate reagent (2.5 g $(NH_4)_6Mo_7O_{24} \cdot 4H_2O$ in 8 ml $H_2SO_4$ diluted to 250 ml). The absorbance at 750 nm is measured on 200 microliter samples in 96 well microtiter plates. Substrate and enzyme blanks are included. A phosphate standard curve is also included (0-2 mM phosphate). 1 FYT equals the amount of enzyme that releases 1 micromol phosphate/min at the given conditions.

Example 2

Test for Specific Activity

The specific activity can be determined as follows:

A highly purified sample of the phytase is used (the purity is checked beforehand on an SDS poly acryl amide gel showing the presence of only one component).

The protein concentration in the phytase sample is determined by amino acid analysis as follows: An aliquot of the phytase sample is hydrolyzed in 6 N HCl, 0.1% phenol for 16 h at 110° C. in an evacuated glass tube. The resulting amino acids are quantified using an Applied Biosystems 420A amino acid analysis system operated according to the manufacturer's instructions. From the amounts of the amino acids the total mass—and thus also the concentration—of protein in the hydrolyzed aliquot can be calculated.

The activity is determined in the units of FYT. One FYT equals the amount of enzyme that liberates 1 micromol inorganic phosphate from phytate (5 mM phytate) per minute at pH 5.5, 37° C.; assay described e.g. in example 1.

The specific activity is the value of FYT/mg enzyme protein.

Example 3

Test for Temperature and pH Activity and Stability

Temperature and pH activity and stability can be determined as follows:

Temperature profiles (i.e. temperature activity relationship) by running the FYT assay of Example 1 at various temperatures (preheating the substrate).

Temperature stability by pre-incubating the phytase in 0.1 M sodium phosphate, pH 5.5 at various temperatures before measuring the residual activity.

The pH-stability by incubating the enzyme at pH 3 (25 mM glycine-HCl), pH 4-5 (25 mM sodium acetate), pH 6 (25 mM MES), pH 7-9 (25 mM Tris-HCl) for 1 hour at 40° C., before measuring the residual activity.

The pH-profiles (i.e. pH activity relationship) by running the assay at the various pH using the same buffer-systems (50 mM, pH re-adjusted when dissolving the substrate).

Example 4

DSC as a Preferred Test for Thermostability

The thermostability or melting temperature, Tm, can be determined as follows:

In DSC the heat consumed to keep a constant temperature increase in the sample-cell is measured relative to a reference cell. A constant heating rate is kept (e.g. 90° C./hour). An endo-thermal process (heat consuming process—e.g. the unfolding of an enzyme/protein) is observed as an increase in the heat transferred to the cell in order to keep the constant temperature increase.

DSC can be performed using the MC2-apparatus from MicroCal. Cells are equilibrated 20 minutes at 20° C. before scanning to 90° C. at a scan rate of 90°/h. Samples of e.g. around 2.5 mg/ml phytase in 0.1 M sodium acetate, pH 5.5 are loaded.

Example 5

Phytase Variants of Amended Activity Characteristics

Variants of an *Aspergillus fumigatus* model phytase (a wild type phytase derived from strain ATCC 13073) were prepared as described in EP 98104858.0 (EP-A-0897010), examples 2-3 and 5, and the phytase activity was determined as described in example 7 thereof. pH and temperature optima and melting point were determined as described in examples 9 and 10 of EP 98113176.6 (EP-A-0897985).

In Table 1, variants of improved specific activity at pH 5.0 are listed. Table 2 lists variants of improved relative activity at pH 3.0, and Table 3 lists variants of improved thermostability (temperature optimum, e.g. determined by DSC).

TABLE 1

| Amended in position no. | Substitution into | Specific activity at pH 5.0 (U/mg) |
|---|---|---|
| 43 | 43L | 83.4 |
|  | 43N | 45.5 |
|  | 43T | 106.9 |
|  | 43I | 91.2 |
|  | 43V | 35.0 |
|  | 43A | 27.3 |
|  | 43G | 59.6 |
| 43 and 270 | 43L, 270L | 88.7 |
| 43 and 270 and 273 | 43L, 270L, 273D | 92.3 |
| 43 and 78 | 43L, 78D | 118.5 |
| 43 and 153 and 154 | 43L, 153Y, 154G | 193.0 |
| *A. fumigatus* wild-type phytase | — | 26.5 |

TABLE 2

| Amended in position no. | Substitution into | Relative phytase activity at pH 3.0 |
|---|---|---|
| 205 | 205E | 41% |
| 273 | 273K | 61% |
| 278 | 278H | 75% |
| 273 and 205 | 273K, 205E | 65% |
| 273 and 278 | 273K, 278H | 100% |
| 273 and 205 and 278 | 273K, 205E, 278H | 96% |
| *A. fumigatus* wild-type phytase | — | 32% |

TABLE 3

| Amended in position no. | Substitution into | Temperature optimum (° C.) | Tm (° C.) (DSC) |
|---|---|---|---|
| 43 and 47 and 88 and 102 and 220 and 242 and 267 | 43T, 47Y, 88I, 102Y, 220L, 242P, 267D | 60 | 67 |
| as above plus 51 and 302 and 337 and 373 and 115 | as above plus 51A, 302H, 337T, 373A, 115N | 63 | — |
| *A. fumigatus* wild-type phytase | — | 55 | 62.5 |

Example 6

Further Phytase Variants of Amended Activity Characteristics

Variants of the ascomycete consensus sequence "conphys" of FIG. 9 were prepared as described in EP 98113176.6 (EP-A-0897985), examples 4-8. Phytase activity, including pH- and temperature optimum, and melting point was determined as described in examples 9 and 10, respectively, thereof.

The tables below list variants of amended activity characteristics, viz.

Table 4 variants of improved specific activity at pH 6.0;

Table 5 variants of amended pH optimum (the pH-optimum indicated is an approximate value, determined as that pH-value (selected from the group consisting of pH 4.0; 4.5; 5.0; 5.5; 6.0; 6.5; and 7;0) at which the maximum phytase activity was obtained);

Table 6 a variant of improved thermostability (expressed by way of the melting point as determined by differential scanning calorimetry (DSC)); and Table 7 variants of amended thermostability (temperature optimum); a "+" or "–" indicates a positive or a negative, respectively, effect on temperature optimum of up to 1° C.; and a "++" and "– –" means a positive or a negative, respectively, effect on temperature optimum of between 1 and 3° C.

TABLE 4

| Amended in position no. | Substitution into | Specific activity at pH 6.0 (U/mg) |
|---|---|---|
| 43 | 43T | 130 |
|  | 43L | 205 |
| Conphys | — | 62 |

TABLE 5

| Amended in position no. | Substitution into | pH optimum around |
|---|---|---|
| 43 | 43T | 6.0 |
|  | 43L | 5.5 |
|  | 43G | 6.5 |
| 43 and 44 | 43L, 44N | 6.0 |
|  | 43T, 44N | 5.5 |
| Conphys | — | 6.0 |

TABLE 6

| Amended in position no. | Substitution into | Tm (° C.) |
|---|---|---|
| 43 | 43T | 78.9 |
| Conphys | — | 78.1 |

TABLE 7

| Amended in position no. | Substitution into | Temperature optimum amendment |
|---|---|---|
| 51 | A | + |
| 58 | K | + |
| 220 | N | + |
| 195 | L | ++ |
| 201e | T | ++ |
| 244 | D | + |
| 264 | I | + |
| 302 | H | + |
| 337 | T | ++ |
| 352 | K | + |
| 373 | A | ++ |
| 47 | F | – |
| 62 | I | – |
| 83 | K | – |
| 90 | R | – |
| 143 | N | – |
| 148 | V | – – |
| 186 | A | – – |
| 187a | S | – |
| 198 | V | – |
| 204 | A | – – |
| 211 | V | – |
| 215 | P | – – |
| 251e | Q | – |
| 260 | A | – |

TABLE 7-continued

| Amended in position no. | Substitution into | Temperature optimum amendment |
|---|---|---|
| 265 | A | – |
| 339 | V | – |
| 365 | A | – – |
| 383k | E | – |
| 404 | G | – – |
| 417 | R | – – |
| Conphys | — | 0 |

TABLE 8

| Amended in position no. | Substitution into | Tm (° C.) (DSC) | Specific activity at pH 5.0 (U/mg) |
|---|---|---|---|
| 43 and 51 and 220 and 244 and 264 and 302 and 337 and 352 and 373 | 51A, 220N, 244D, 264I, 302H, 337T, 352K, 373A, 43T | 84.7 | 105 |
| as above plus 80 | as above plus 80A | 85.7 | 180 |
| Conphys | — | 78.1 | 30 |

Example 7

Cloning of a Phytase of *Cladorrhinum Foecundissimum*

DNA encoding a phytase from *Cladorrhinum foecundissimum* CBS 427.97 has been cloned, and the enzyme isolated and purified, essentially as described in WO 98/28409.

FIG. 2 shows the DNA sequence of the HindIII/XbaI cloned PCR product in pA2phy8. The cloned PCR product is amplified from the genomic region encoding *Cladorrhinum foecundissimum* CBS 427.97 phyA gene. The putative intron is indicated by double underline of the excision-ligation points in accordance with the GT-AG rule (R. Breathnach et al. Proc. Natl. Acad. Sci. USA 75 (1978) pp4853-4857). The restrictions sites used for cloning are underlined.

According to the SignalP V1.1 prediction (Henrik Nielsen, Jacob Engelbrecht, Stren Brunak and Gunnar von Heijne: "Identification of prokaryotic and eukaryotic signal peptides and prediction of their cleavage sites," Protein Engineering 10, 1-6 (1997)), the signal peptide part of the enzyme corresponds to amino acids nos. 1-15, accordingly the mature enzyme is amino acids nos. 16-495.

The enzyme exhibits a pH optimum around pH 6 with no activity at the low pH (pH 3), but significant activity up until pH 7.5; thus it is a more alkaline phytase as compared to the *Aspergillus ficuum* phytase.

A temperature optimum around 60° C. was found at pH 5.5. Thus, this phytase is more thermostable than the *A. ficuum* phytase.

Example 8

Alignment of a New Model Phytase According to FIG. 1

The phytase sequence of *Cladorrhinum foecundissimum* as disclosed in Example 7 is compared with the 13 model phytases of FIG. 1 using GAP version 8 referred to above with a GAP weight of 3.000 and a GAP lengthweight of 0.100. Complete amino acid sequences are compared. The M_thermophila phytase sequence turns up to be the most homologous sequence, showing a degree of similarity to the *C. foecundissimum* sequence of 70.86%.

Still using the GAP program and the,parameters mentioned above, the phytase sequence "*C_foecundissimum*" is now aligned to the "*M-thermophila*" phytase—see FIG. 3. The average match is 0.540; the average mismatch —0.396; quality 445.2; length 505; ratio 0.914; gaps 9; percent similarity 70.860; percent identity 53.878.

In a next step, see FIGS. 4A-4D, the *C_foecundissimum* is pasted (or it could simply be written) onto the alignment of FIG. 1 as the bottom row, ensuring that those amino acid residues which according to the alignment at FIG. 3 are identical (indicated by a vertical line) or similar (indicated by one or two dots) are placed above each other. At 5 places along the sequence, the *C_foecundissimum* sequence comprises "excess" amino acid residues, which the alignment of FIG. 1 does not make room for. At FIGS. 4A-4D, these excess residues are transferred onto a next row (but they can be included in the multiple alignment and numbered as described previously in the position numbering related paragraphs (using the denotations a, b, c etc.).

Corresponding variants of the phytase of *C_foecundissimum* are then easily deduced on the basis of FIGS. 4A-4D. Some examples: The variants generally designated "80K,A" and "43T" in *C_foecundissimum* correspond to "K80A" and "Q43T," respectively.

The invention claimed is:

1. A method of producing a modified phytase, comprising introducing a mutation in an amino acid sequence of a phytase, wherein the modified phytase has phytase activity and the mutation is at one or more positions selected from the group consisting of:
71; 72; 73; 74; 75; 76; 77; 78; 81; 82; 84; 116; 117; 119; and 120;
wherein each position corresponds to the position of the amino acid sequence of the mature *P. lycii* phytase (SEQ ID NO: 7).

2. The method of claim 1, comprising introducing a mutation at position 71.

3. The method of claim 1, comprising introducing a mutation at position 72.

4. The method of claim 1, comprising introducing a mutation at position 73.

5. The method of claim 1, comprising introducing a mutation at position 74.

6. The method of claim 1, comprising introducing a mutation at position 75.

7. The method of claim 1, comprising introducing a mutation at position 76.

8. The method of claim 1, comprising introducing a mutation at position 77.

9. The method of claim 1, comprising introducing a mutation at position 78.

10. The method of claim 1, comprising introducing a mutation at position 81.

11. The method of claim 1, comprising introducing a mutation at position 82.

12. The method of claim 1, comprising introducing a mutation at position 84.

13. The method of claim 1, comprising introducing a mutation at position 116.

14. The method of claim 1, comprising introducing a mutation at position 117.

15. The method of claim 1, comprising introducing a mutation at position 119.

16. The method of claim 1, comprising introducing a mutation at position 120.

17. The method of claim 1, wherein the mutation comprises a substitution selected from the group consisting of:
75W,F; 78D,S; 81A,G,Q,E; 82T; 84I,Y,Q,V; 116S; 119E; and 120L.

18. The method of claim 1, wherein the phytase is an ascomycete phytase.

19. The method of claim 18, wherein the phytase is an *Aspergillus* phytase.

20. The method of claim 19, wherein the phytase is an *Aspergillus ficuum*, *Aspergillus fumigatus*, *Aspergillus nidulans*, *Aspergillus niger*, or *Aspergillus terreus* phytase.

21. The modified phytase of claim 19, wherein the phytase is an *Aspergillus terreus*, CBS 116.48 phytase.

22. The method of claim 1, wherein the phytase is a *Myceliophthora thermophila*, *Talaromyces thermophilus*, or *Thermomyces lanuginosus* phytase.

23. The method of claim 22, wherein the phytase is a *Myceliophora thermophila*, ATCC 34625 or ATCC 74340 phytase.

24. The method of claim 22, wherein the phytase is a *Talaromyces thermophilus*, ATCC 20186 or ATCC 74338 phytase.

25. The method of claim 22, wherein the phytase is a *Thermomyces lanuginosus*, NRRL B-21527 phytase.

26. The method of claim 1, wherein the phytase is an ascomycete consensus phytase sequence.

27. The method of claim 1, wherein the phytase is a basidiomycete phytase.

28. The method of claim 27, wherein the phytase is an *Agrocybe pediades, Paxillus involutus, Peniophora lycil*, or *Trametes pubescens* phytase.

29. The method of claim 28, wherein the phytase is a *Paxillus involutus*, CBS 100231 phytase.

30. The method of claim 28, wherein the phytase is a *Paxillus involutus*, CBS 100231 Phy-A2 phytase.

31. The method of claim 28, wherein the phytase is a *Trametes pubescens*, CBS 100232 phytase.

* * * * *